US008362049B2

(12) United States Patent
Murray et al.

(10) Patent No.: US 8,362,049 B2
(45) Date of Patent: Jan. 29, 2013

(54) UREA GLUCOKINASE ACTIVATORS

(75) Inventors: Anthony Murray, Charlottenlund (DK); Jesper Lau, Farum (DK); Per Vedsoe, Vaerloese (DK); Lise Brown Christiansen, Lyngby (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 13/415,000

(22) Filed: Mar. 8, 2012

(65) Prior Publication Data

US 2012/0165375 A1 Jun. 28, 2012

Related U.S. Application Data

(63) Continuation of application No. 12/522,469, filed as application No. PCT/EP2008/050140 on Jan. 8, 2008.

(60) Provisional application No. 60/879,961, filed on Jan. 11, 2007.

(30) Foreign Application Priority Data

Jan. 11, 2007 (EP) .................................... 07100406

(51) Int. Cl.
*A61K 31/426* (2006.01)
*A61P 3/10* (2006.01)
*C07D 277/54* (2006.01)

(52) U.S. Cl. ........................................ 514/369; 548/185
(58) Field of Classification Search ........................ None
See application file for complete search history.

(56) References Cited

U.S. PATENT DOCUMENTS

| | | | |
|---|---|---|---|
| 3,067,250 A | 12/1962 | Oja | |
| 3,152,136 A | 10/1964 | Harris et al. | |
| 3,317,534 A | 5/1967 | Nitta et al. | |
| 3,424,762 A | 1/1969 | Helsley | |
| 3,551,442 A | 12/1970 | Guillot et al. | |
| 3,734,923 A | 5/1973 | Dowding et al. | |
| 3,862,163 A | 1/1975 | Boroschewski et al. | |
| 3,874,873 A | 4/1975 | Volpp et al. | |
| 3,887,709 A | 6/1975 | Brzozowski et al. | |
| 3,967,950 A | 7/1976 | Kano et al. | |
| 4,153,710 A | 5/1979 | Brzozowski et al. | |
| 4,160,833 A | 7/1979 | Diel | |
| 4,174,398 A | 11/1979 | Regel et al. | |
| 4,175,081 A | 11/1979 | Driscoll | |
| 4,183,856 A | 1/1980 | Makisumi et al. | |
| 4,241,072 A | 12/1980 | Bolhofer | |
| 4,243,404 A | 1/1981 | Kruger et al. | |
| 4,405,644 A | 9/1983 | Kabbe et al. | |
| 4,694,004 A | 9/1987 | Nakaguti et al. | |
| 4,808,722 A | 2/1989 | Henrie | |
| 5,262,415 A | 11/1993 | Takemoto et al. | |
| 5,371,086 A | 12/1994 | Takemoto et al. | |
| 5,556,969 A | 9/1996 | Chambers et al. | |
| 5,846,985 A | 12/1998 | Murugesan | |
| 5,846,990 A | 12/1998 | Murugesan et al. | |
| 5,849,732 A | 12/1998 | Suzuki et al. | |
| 5,849,769 A | 12/1998 | Lind et al. | |
| 5,891,917 A | 4/1999 | Tang et al. | |
| 5,935,993 A | 8/1999 | Tang et al. | |
| 6,001,860 A | 12/1999 | Hamanaka | |
| 6,140,343 A | 10/2000 | DeNinno et al. | |
| 6,180,635 B1 | 1/2001 | Cheshire et al. | |
| 6,225,346 B1 | 5/2001 | Tang et al. | |
| 6,268,384 B1 | 7/2001 | Novak et al. | |
| 6,271,248 B1 | 8/2001 | Murugesan et al. | |
| 6,337,338 B1 | 1/2002 | Kozlowski et al. | |
| 6,384,220 B2 | 5/2002 | Corbett et al. | |
| 6,448,290 B1 | 9/2002 | Ohuchuida et al. | |
| 6,486,184 B2 | 11/2002 | Kester et al. | |
| 6,489,478 B1 | 12/2002 | DeNinno et al. | |
| 6,500,817 B1 | 12/2002 | Fischer et al. | |
| 6,559,168 B2 | 5/2003 | Marfat et al. | |
| 6,608,218 B2 | 8/2003 | Kester et al. | |
| 6,720,347 B2 | 4/2004 | Rawlins et al. | |
| 6,720,427 B2 | 4/2004 | Sanner et al. | |
| 6,784,198 B1 | 8/2004 | Pevarello et al. | |
| 6,863,647 B2 | 3/2005 | Pevarello et al. | |
| 6,875,760 B2 | 4/2005 | Lau et al. | |
| 6,903,125 B2 | 6/2005 | Kontani et al. | |
| 6,916,814 B2 | 7/2005 | Moss et al. | |
| 6,936,629 B2 | 8/2005 | Chan Chun Kong et al. | |
| 7,056,942 B2 | 6/2006 | Hildesheim et al. | |
| 7,196,104 B2 | 3/2007 | Askew et al. | |
| 7,384,967 B2 | 6/2008 | Polisetti et al. | |
| 7,582,769 B2 | 9/2009 | Murray et al. | |
| 7,884,210 B2 * | 2/2011 | Lau et al. ..................... 548/185 |
| 2002/0002190 A1 | 1/2002 | Corbett et al. | |
| 2002/0198200 A1 | 12/2002 | Kester et al. | |
| 2003/0171411 A1 | 9/2003 | Kodra et al. | |
| 2003/0220350 A1 | 11/2003 | Lau et al. | |
| 2004/0014789 A1 | 1/2004 | Lau et al. | |
| 2004/0014968 A1 | 1/2004 | Bizarro et al. | |
| 2007/0054897 A1 | 3/2007 | Murray et al. | |
| 2009/0216013 A1 | 8/2009 | Murray et al. | |

FOREIGN PATENT DOCUMENTS

| | | |
|---|---|---|
| AU | 29937 | 12/1972 |
| CA | 2416229 | 9/2007 |

(Continued)

OTHER PUBLICATIONS

Chipkin, S.R. et al., "Hormone-Fuel Interrelationships: Fed State, Starvation, and Diabetes Mellitus", Joslin's Diabetes, 1994, pp. 97-115. Colowick, S.P., The Enzymes, 1973, vol. 9, pp. 1-48.
Glaser, B. et al., "Familial Hyperinsulinism Caused by an Activating Glucokinase Mutation", The New England Journal of Medicine, 1998, vol. 338, pp. 226-230.
Grupe, A. et al., "Transgenic Knockouts Reveal a Critical Requirement for Pancreatic β Cell Glucokinase in Maintaining Glucose Homeostasis", Cell, 1995, vol. 83, pp. 69-78.
Liang, Y. et al., "Variable Effects of Maturity-Onset-Diabetes-of-Youth (MODY)-associated Glucokinase Mutations on Substrate Interactions and Stability of the Enzyme", Biochemistry Journal, 1995, vol. 309, pp. 167-173.

(Continued)

*Primary Examiner* — Sun Jae Loewe
(74) *Attorney, Agent, or Firm* — Rosemarie R. Wilk-Orescan

(57) ABSTRACT

This application relates to novel urea glucokinase activators and use of the compounds of the invention for preparation of a medicament for the treatment of various diseases, e.g. for the treatment of type 2 diabetes. Further encompassed is a pharmaceutical composition comprising a compound according to the invention and a process for preparing such.

4 Claims, No Drawings

FOREIGN PATENT DOCUMENTS

| | | |
|---|---|---|
| CN | 100506807 C | 7/2009 |
| DE | 1901501 | 8/1969 |
| DE | 2040580 | 4/1971 |
| DE | 2117807 | 10/1971 |
| DE | 2129418 | 12/1971 |
| DE | 2129418 A1 | 12/1971 |
| DE | 2228890 | 12/1972 |
| DE | 2151766 | 4/1973 |
| DE | 2431801 | 1/1975 |
| DE | 2264983 | 10/1975 |
| DE | 2712630 | 9/1978 |
| EP | 0129408 | 12/1984 |
| EP | 0432040 | 6/1991 |
| EP | 0885890 | 12/1998 |
| EP | 0979823 | 2/2000 |
| EP | 1211246 | 6/2002 |
| EP | 1169312 | 10/2004 |
| FR | 7428 E | 7/1907 |
| FR | 7.428 M | 5/1968 |
| FR | 2001083 | 9/1969 |
| FR | 2001083 A1 | 9/1969 |
| FR | 2215967 | 8/1974 |
| GB | 771147 | 3/1957 |
| GB | 771147 A | 3/1957 |
| GB | 1185540 | 3/1970 |
| GB | 1195672 | 6/1970 |
| GB | 1282308 | 7/1972 |
| GB | 1282308 A | 7/1972 |
| GB | 1318291 | 5/1973 |
| HU | 0200396 | 7/2002 |
| JP | 01056660 | 3/1989 |
| JP | 64056660 | 3/1989 |
| JP | 4334374 | 11/1992 |
| JP | 6016621 | 1/1994 |
| JP | 6102611 | 4/1994 |
| JP | 2002-536056 | 10/2002 |
| RU | 2021258 | 10/1994 |
| WO | WO 91/04027 | 4/1991 |
| WO | WO 93/24458 | 12/1993 |
| WO | WO 94/14801 | 7/1994 |
| WO | WO 94/18170 | 8/1994 |
| WO | WO 97/24328 | 7/1997 |
| WO | WO 99/24035 | 5/1999 |
| WO | WO 99/24416 | 5/1999 |
| WO | WO 99/32106 | 7/1999 |
| WO | WO 99/32111 | 7/1999 |
| WO | WO 99/62890 | 12/1999 |
| WO | WO 00/17165 | 3/2000 |
| WO | 00/26203 A1 | 5/2000 |
| WO | WO 00/26186 | 5/2000 |
| WO | WO 00/26203 | 5/2000 |
| WO | WO 00/45742 | 8/2000 |
| WO | 00/53591 A1 | 9/2000 |
| WO | WO 00/53591 | 9/2000 |
| WO | WO 00/58293 | 10/2000 |
| WO | WO 01/00206 | 4/2001 |
| WO | 01/44217 A1 | 6/2001 |
| WO | WO 01/44216 | 6/2001 |
| WO | WO 01/44217 | 6/2001 |
| WO | WO 01/57008 | 8/2001 |
| WO | WO 01/83465 | 11/2001 |
| WO | WO 01/83478 | 11/2001 |
| WO | WO 01/85706 | 11/2001 |
| WO | WO 01/85707 | 11/2001 |
| WO | WO 02/08209 | 1/2002 |
| WO | WO 02/14311 | 2/2002 |
| WO | WO 02/46173 | 6/2002 |
| WO | WO 02/070494 | 9/2002 |
| WO | WO 03/055482 | 7/2003 |
| WO | WO 03/070727 | 8/2003 |
| WO | WO 2004/002481 | 1/2004 |
| WO | 2004/085388 A2 | 10/2004 |
| WO | WO 2004/085388 | 10/2004 |
| WO | WO 2005/066145 | 7/2005 |
| WO | 2005/103050 A2 | 11/2005 |
| WO | WO 2005/103050 | 11/2005 |
| WO | WO 2007/006814 | 1/2007 |
| WO | WO 2008/084043 | 7/2008 |
| WO | WO 2008/084044 | 7/2008 |

OTHER PUBLICATIONS

Mann, G.V., "The Influence of Obesity on Health", The New England Journal of Medicine, 1974, vol. 291, pp. 226-232.

Meglasson, M. D. et al., "New Perspectives on Pancreatic Islet Glucokinase", American Journal of Physiology, 1984, vol. 246, pp. E1-E13.

National Institute of Health Consensus Development Conference Statement, "Health Complications of Obesity", Annals of Internal Medicine, 1985, Vol, 103, pp. 147-151.

Printz, R.L. et al., "Mammalian Glucokinase", Annual Review of Nutrition, 1993, vol. 13, pp. 463-496.

Diabetes 1, http://diabetesplanner.com/articles_non_mem/diabetes_what_is_the_treatment_for.htm (2011).

Diabetes 2, http://www.osip.com/PSN010.

Lau et al. 2, caphis an 2007:61408.

Diabetes 2, 2011, http://www.mayoclinic.om/health/type-2-diabetes/DS00585.

Diabetes2-2, 2011, http://www.mayoclinic.com/health/type-2-diabetes/DS00585/DSECTION=prevention.

Examination Report for EP App. No. 08707837.4, dated Jul. 11, 2011.

Patani et al., Chem Rev, 1996, 96, 3147-3176.

Castelhano et al., 2005, "Glucokinase-Activating Ureas," Bioorganic & Medicinal Chemistry Letters 15:1501-1504.

Chipkin et al., 1994, "Hormone-Fuel Interralationships . . ." Joslin's Diabetes 97-115.

Decombe, 1932, "Acylacetic Esters," Annali Di Chimica Applicata 18:81-187.

English Translation of Decombe, 1932, "Acylacetic Esters," Annali Di Chimica Applicata 18:81-187.

Evans, et al., 1986, "Design of potent, orally effective, nonpeptidal antagonists of the peptide hormone cholecystokinin," Proceedings of the National Academy of Sciences of the United States of America, vol. 83, No. 13, Juillet 1986, USA pp. 4918-4922 (corresponds to EP0432040 in the foreign patents section).

Ferre et al., 1996, "Evidence From Transgenic Mice That . . ." The FASEB Journal 10:1213-4218.

Gardner, 1948, "The Polyoxyphenol Series III Syntheses of . . ." Canadian Journal of Research 26b:681-693.

Girard et al., 1997, Annual Review of Nutrition 17:325-352.

Grassie et al., 1950, "Preliminary Test on Possible New Stabilizers . . ." Canadian Journal of Research 28b:468-484.

Goerdeler et al., 1980, "Acylcarbodiimides. IV. Preparation and Some Reactions of Carbamoylcarboiimides," Hcaplus, Accession No. 585914.

Heitmeier et al., 1964, "Hydroxyphenethylamino Derivatives of Various Nitrogen Heterocycles," Journal of Medicinal Chemistry 7(3):288-293.

Mylari et al., 2003, "Design and Synthesis of a Novel Family of Triazine-Based Inhibitors of Sorbitol Dehydrogenase with Oral Activity: 1-{4-[3R,5S-Dimethyl-4-(4-methyl-[1,3,5]triazin-2-yl)-piperazin-1-yl]-[1,3,5]triazin-2-yl}-(R) Ethanol," Bioorganic & Medicinal Chemistry 11:4179-4188.

Purchase et al., 1996, "Tetrazole-Substituted Ureas As Inhibitors of Acyl-COA:Cholesterol O-Acyltransferase (ACAT) A Novel Preparation of Ureas From Weakly Nucleophilic Amines," Bioorganic & Medicinal Chemistry Letters 6(15):1753-1758.

Scheler, 1969, "Heat Developable Diazotype Material," HCAPLUS, Accession No. 444446, Nov. 5, 1968.

Sovetskaya Enthiklopedia, 1983, "Encyclopedic Dictionary," Sovetskaya Enthiklopedia pp. 130-131.

English Translation of Sovetskaya, Enthiklopedia, pp. 130-131 (1983).

Wawer, 1999, Magnetic Resonance in Chemistry 37(3):189-194.

White et al., 1996, "Heterocyclic Ureas: Inhibitors of Acyl-COA:Cholesterol O-Acyltransferase as Hypocholesterolemic Agents," Journal of Medicinal Chemistry 39(22):4382-4395.

Wolff, 1995, "Burger's Medicinal Chemistry and Drug Discovery," Burger's Medicinal Chemistry and Drug Discovery 172-178.

Machine Translation of DE2264983, 2012.
Machine Translation of DE2228890, 2012.
Machine Translation of DE2151766, 2012.
Machine Translation of DE2040580, 2012.
English Abstract of DE1901501, 2012.
English Abstract of EP432040 (correlates to Evans et al.), 2012.
Machine Translation of FR7.428M, 2012.
English Abstract of HU200396, 2012.
Machine Translation of JP4334374, 2012.
Machine Translation of JP6102611, 2012.
English Abstract of JP6016621, 2012.

Regel, et al., 1977, "Acylierung and C-2 Von Imidazolen Und Benzimidazolen," Liebigs Annalen Der Chemie 1:145-158.
Castelhano, A. L. et al., "Glucokinase-activating Ureas", Bioorganic & Medicinal Chemistry Letters, 2005, vol. 15, pp. 1501-1504.
Ferre, T. et al., "Evidence from Transgenic Mice that Glucokinase is Rate Limiting for Glucose Utilization in the Liver", The Faseb Journal, 1996, vol. 10, pp. 1213-1218.
Preliminary Amendment submitted Jan. 4, 2012 in U.S. Appl. No. 12/961,867, filed Dec. 7, 2010, by Lau et al.

* cited by examiner

UREA GLUCOKINASE ACTIVATORS

CROSS-REFERENCE TO RELATED APPLICATIONS

This application is a continuation of U.S. application Ser. No. 12/522,469, filed Jul. 8, 2009, which is a 371 National Stage filing of PCT/EP2008/050140, filed Jan. 8, 2008, which claims priority from European Application No. 07100406.3, filed Jan. 11, 2007 and from U.S. Provisional Application No. 60/879,961, filed Jan. 11, 2007.

FIELD OF THE INVENTION

This application relates to novel urea glucokinase activators and their use in treatment of assorted diseases.

BACKGROUND OF THE INVENTION

Glucokinase (GK) is one of four hexokinases that are found in mammals [Colowick, S. P., in The Enzymes, Vol. 9 (P. Boyer, ed.) Academic Press, New York, N.Y., pages 1-48, 1973]. The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a ratecontrolling enzyme for glucose metabolism in these two cell types that are known to play critical roles in whole-body glucose homeostasis [Chipkin, S. R., Kelly, K. L., and Ruderman, N. B. in Joslin's Diabetes (C. R. Khan and G. C. Wier, eds.), Lea and Febiger, Philadelphia, Pa., pages 97-115, 1994]. The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal [Printz, R. G., Magnuson, M. A., and Granner, D. K. in Ann. Rev. Nutrition Vol. 13 (R. E. Olson, D. M. Bier, and D. B. McCormick, eds.), Annual Review, Inc., Palo Alto, Calif., pages 463-496, 1993]. These findings contributed over a decade ago to the hypothesis that GK functions as a glucose sensor in β-cells and hepatocytes (Meglasson, M. D. and Matschinsky, F. M. Amer. J. Physiol. 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., Cell 83, 69-78, 1995; Ferrie, T., Riu, E., Bosch, F. et al., FASEB J., 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., Biochem. J. 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., New England J. Med. 338, 226-230, 1998). While mutations of the GK gene are not found in the majority of patients with type 2 diabetes, compounds that activate GK and, thereby, increase the sensitivity of the GK sensor system will still be useful in the treatment of the hyperglycemia characteristic of all type 2 diabetes. Glucokinase activators will increase the flux of glucose metabolism in β-cells and hepatocytes, which will be coupled to increased insulin secretion. Such agents would be useful for treating type II diabetes. Several GK activators are known, see, for example, US 2004/0014968 (Hofmann-La Roche Inc.), WO 2003/055482 (Novo Nordisk A/S) and WO 2004/002481 (Novo Nordisk A/S).

Diabetes is characterised by an impaired glucose metabolism manifesting itself among other things by an elevated blood glucose level in the diabetic patients. Underlying defects lead to a classification of diabetes into two major groups: Type 1 diabetes, or insulin demanding diabetes mellitus (IDDM), which arises when patients lack β-cells producing insulin in their pancreatic glands, and type 2 diabetes, or non-insulin dependent diabetes mellitus (NIDDM), which occurs in patients with an impaired β-cell function besides a range of other abnormalities.

Type 1 diabetic patients are currently treated with insulin, while the majority of type 2 diabetic patients are treated either with sulphonylureas that stimulate β-cell function or with agents that enhance the tissue sensitivity of the patients towards insulin or with insulin. Among the agents applied to enhance tissue sensitivity towards insulin metformin is a representative ex-ample.

Even though sulphonylureas are widely used in the treatment of NIDDM this therapy is, in most instances, not satisfactory: In a large number of NIDDM patients sulphonylureas do not suffice to normalise blood sugar levels and the patients are, therefore, at high risk for acquiring diabetic complications. Also, many patients gradually lose the ability to respond to treatment with sulphonylureas and are thus gradually forced into insulin treatment. This shift of patients from oral hypoglycaemic agents to insulin therapy is usually ascribed to exhaustion of the β-cells in NIDDM patients.

In normal subjects as well as in diabetic subjects, the liver produces glucose in order to avoid hypoglycaemia. This glucose production is derived either from the release of glucose from glycogen stores or from gluconeogenesis, which is a de novo intracellular synthesis of glucose. In type 2 diabetes, however, the regulation of hepatic glucose output is poorly controlled and is increased, and may be doubled after an overnight fast. Moreover, in these patients there exists a strong correlation between the increased fasting plasma glucose levels and the rate of hepatic glucose production. Similarly, hepatic glucose production will be increased in type 1 diabetes, if the disease is not properly controlled by insulin treatment.

Since existing forms of therapy of diabetes does not lead to sufficient glycaemic control and therefore are unsatisfactory, there is a great demand for novel therapeutic approaches.

Atherosclerosis, a disease of the arteries, is recognized to be the leading cause of death in the United States and Western Europe. The pathological sequence leading to atherosclerosis and occlusive heart disease is well known. The earliest stage in this sequence is the formation of "fatty streaks" in the carotid, coronary and cerebral arteries and in the aorta. These lesions are yellow in colour due to the presence of lipid deposits found principally within smooth-muscle cells and in macrophages of the intima layer of the arteries and aorta. Further, it is postulated that most of the cholesterol found within the fatty streaks, in turn, give rise to development of the "fibrous plaque", which consists of accumulated intimal smooth muscle cells laden with lipid and surrounded by extracellular lipid, collagen, elastin and proteoglycans. The cells plus matrix form a fibrous cap that covers a deeper deposit of cell debris and more extracellular lipid. The lipid is primarily free and esterified cholesterol. The fibrous plaque forms slowly, and is likely in time to become calcified and necrotic, advancing to the "complicated lesion" which accounts for the arterial occlusion and tendency toward mural thrombosis and arterial muscle spasm that characterize advanced atherosclerosis.

Epidemiological evidence has firmly established hyperlipidemia as a primary risk factor in causing cardiovascular disease (CVD) due to atherosclerosis. In recent years, leaders of the medical profession have placed renewed emphasis on lowering plasma cholesterol levels, and low density lipoprotein cholesterol in particular, as an essential step in prevention of CVD. The upper limits of "normal" are now known to be significantly lower than heretofore appreciated. As a result, large segments of Western populations are now realized to be at particular high risk. Independent risk factors include glucose intolerance, left ventricular hypertrophy, hypertension, and being of the male sex. Cardiovascular disease is especially prevalent among diabetic subjects, at least in part because of the existence of multiple independent risk factors in this population. Successful treatment of hyperlipidemia in the general population, and in diabetic subjects in particular, is therefore of exceptional medical importance.

Hypertension (or high blood pressure) is a condition, which occurs in the human population as a secondary symptom to various other disorders such as renal artery stenosis, pheochromocytoma, or endocrine disorders. However, hypertension is also evidenced in many patients in whom the causative agent or disorder is unknown. While such "essential" hypertension is often associated with disorders such as obesity, diabetes, and hypertriglyceridemia, the relationship between these disorders has not been elucidated. Additionally, many patients display the symptoms of high blood pressure in the complete absence of any other signs of disease or disorder.

It is known that hypertension can directly lead to heart failure, renal failure, and stroke (brain haemorrhaging). These conditions are capable of causing short-term death in a patient. Hypertension can also contribute to the development of atherosclerosis and coronary disease. These conditions gradually weaken a patient and can lead to long-term death.

The exact cause of essential hypertension is unknown, though a number of factors are believed to contribute to the onset of the disease. Among such factors are stress, uncontrolled emotions, unregulated hormone release (the renin, angiotensin aldosterone system), excessive salt and water due to kidney malfunction, wall thickening and hypertrophy of the vasculature resulting in constricted blood vessels and genetic factors.

The treatment of essential hypertension has been undertaken bearing the foregoing factors in mind. Thus a broad range of beta-blockers, vasoconstrictors, angiotensin converting enzyme inhibitors and the like have been developed and marketed as antihypertensives. The treatment of hypertension utilizing these compounds has proven beneficial in the prevention of short-interval deaths such as heart failure, renal failure, and brain haemorrhaging. How-ever, the development of atherosclerosis or heart disease due to hypertension over a long period of time remains a problem. This implies that although high blood pressure is being reduced, the underlying cause of essential hypertension is not responding to this treatment.

Hypertension has been associated with elevated blood insulin levels, a condition known as hyperinsulinemia. Insulin, a peptide hormone whose primary actions are to pro-mote glucose utilization, protein synthesis and the formation and storage of neutral lipids, also acts to pro-mote vascular cell growth and increase renal sodium retention, among other things. These latter functions can be accomplished without affecting glucose levels and are known causes of hypertension. Peripheral vasculature growth, for example, can cause constriction of peripheral capillaries, while sodium retention increases blood volume. Thus, the lowering of insulin levels in hyperinsulinemics can prevent abnormal vascular growth and renal sodium retention caused by high insulin levels and thereby alleviates hypertension.

Cardiac hypertrophy is a significant risk factor in the development of sudden death, myocardial infarction, and congestive heart failure. Theses cardiac events are due, at least in part, to increased susceptibility to myocardial injury after ischemia and reperfusion, which can occur in out-patient as well as perioperative settings. There is an unmet medical need to prevent or minimize adverse myocardial perioperative outcomes, particularly perioperative myocardial infarction. Both non-cardiac and cardiac surgery are associated with substantial risks for myocardial infarction or death. Some 7 million patients undergoing non-cardiac surgery are considered to be at risk, with incidences of perioperative death and serious cardiac complications as high as 20-25% in some series. In addition, of the 400,000 patients undergoing coronary bypass surgery annually, perioperative myocardial infarction is estimated to occur in 5% and death in 1-2%. There is currently no drug therapy in this area, which reduces damage to cardiac tissue from perioperative myocardial ischemia or enhances cardiac resistance to ischemic episodes. Such a therapy is anticipated to be life-saving and reduce hospitalizations, enhance quality of life and reduce overall health care costs of high risk patients.

Obesity is a well-known risk factor for the development of many very common diseases such as atherosclerosis, hypertension, and diabetes. The incidence of obese people and thereby also these diseases is increasing throughout the entire industrialised world. Except for exercise, diet and food restriction no convincing pharmacological treatment for reducing body weight effectively and acceptably currently exists. However, due to its indirect but important effect as a risk factor in mortal and common diseases it will be important to find treatment for obesity and/or means of appetite regulation.

The term obesity implies an excess of adipose tissue. In this context obesity is best viewed as any degree of excess adiposity that imparts a health risk. The cut off between normal and obese individuals can only be approximated, but the health risk imparted by the obesity is probably a continuum with increasing adiposity. The Framingham study demonstrated that a 20% excess over desirable weight clearly imparted a health risk (Mann GV N. Engl. J. Med 291:226, 1974). In the United States a National Institutes of Health consensus panel on obesity agreed that a 20% increase in relative weight or a body mass index (BMI=body weight in kilograms divided by the square of the height in meters) above the 85th percentile for young adults constitutes a health risk. By the use of these criteria 20 to 30 percent of adult men and 30 to 40 percent of adult women in the United States are obese. (NIH, Ann Intern Med 103:147, 1985).

Even mild obesity increases the risk for premature death, diabetes, hypertension, atherosclerosis, gallbladder disease, and certain types of cancer. In the industrialised western world the prevalence of obesity has increased significantly in the past few decades. Because of the high prevalence of obesity and its health consequences, its prevention and treatment should be a high public health priority.

When energy intake exceeds expenditure, the excess calories are stored in adipose tissue, and if this net positive balance is prolonged, obesity results, i.e. there are two components to weight balance, and an abnormality on either side (intake or expenditure) can lead to obesity.

The regulation of eating behaviour is incompletely understood. To some extent appetite is controlled by discrete areas in the hypothalamus: a feeding centre in the ventrolateral nucleus of the hypothalamus (VLH) and a satiety centre in the ventromedial hypothalamus (VMH). The cerebral cortex receives positive signals from the feeding centre that stimulate eating, and the satiety centre modulates this process by sending inhibitory impulses to the feeding centre. Several regulatory processes may influence these hypothalamic centres. The satiety centre may be activated by the increases in plasma glucose and/or insulin that follow a meal. Meal induced gastric distension is another possible inhibitory factor.

Additionally the hypothalamic centres are sensitive to catecholamines, and beta adrenergic stimulation inhibits eating behaviour. Ultimately, the cerebral cortex controls eating behaviour, and impulses from the feeding centre to the cerebral cortex are only one input. Psychological, social, and genetic factors also influence food intake.

At present a variety of techniques are available to effect initial weight loss. Unfortunately, initial weight loss is not an optimal therapeutic goal. Rather, the problem is that most obese patients eventually regain their weight. An effective means to establish and/or sustain weight loss is the major challenge in the treatment of obesity today.

SUMMARY OF THE INVENTION

The invention provides urea glucokinase activators as described in the embodiments.

The present invention also provides use of the compounds of the invention for preparation of a medicament for the treatment of various diseases, e.g. for the treatment of type 2 diabetes. Further encompassed is a pharmaceutical composition comprising a compound according to the invention and a process for preparing such.

DESCRIPTION OF THE INVENTION

In the structural formulas given herein and throughout the present specification, the following terms have the indicated meaning:

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated.

As used herein, the term "attached" or "-" (e.g. —C(O)R$^{11}$ which indicates the carbonyl attachment point to the scaffold) signifies a stable covalent bond.

As used herein, the terms "contain" or "containing" can refer to in-line substitutions at any position along the above defined alkyl, alkenyl, alkynyl or cycloalkyl substituents with one or more of any of O, S, SO, SO$_2$, N, or N-alkyl, including, for example, —CH$_2$—O—CH$_2$—, —CH$_2$—SO$_2$—CH$_2$—, —CH$_2$—NH—CH$_3$ and so forth.

Certain of the above defined terms may occur more than once in the structural formulae, and upon such occurrence each term shall be defined independently of the other.

As used herein, the term "solvate" is a complex of variable stoichiometry formed by a solute (in this invention, a compound of formula (I)) and a solvent. Such solvents for the purpose of the present invention may not interfere with the biological activity of the solute. Solvents may be, by way of example, water, ethanol, or acetic acid.

As used herein, the term "biohydrolyzable ester" is an ester of a drug substance (in this invention, a compound of formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is trans-formed to (I) in plasma. Many examples of such are known in the art and include by way of example lower alkyl esters (e.g., C$_{1-4}$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to (I) in plasma. Many examples of such are known in the art and include by way of example lower alkyl amides, α-amino acid amides, alkoxyacyl amides, and alkylaminoalkylcarbonyl amides.

As used herein, the term "prodrug" includes biohydrolyzable amides and biohydrolyzable esters and also encompasses a) compounds in which the biohydrolyzable functionality in such a prodrug is encompassed in the compound of formula (I) and b) compounds which may be oxidized or reduced biologically at a given functional group to yield drug substances of formula (I). Examples of these functional groups include, but are not limited to, 1,4-dihydropyridine, N-alkylcarbonyl-1,4-dihydropyridine, 1,4-cyclohexadiene, tert-butyl, and the like.

The term "pharmacologically effective amount" or shall mean that amount of a drug or pharmaceutical agent that will elicit the biological or medical response of a tissue, animal or human that is being sought by a researcher or clinician. This amount can be a therapeutically effective amount. The term "therapeutically effective amount" shall mean that amount of a drug or pharmaceutical agent that will elicit the therapeutic response of an animal or human that is being sought.

The term "treatment" and "treating" as used herein means the management and care of a patient for the purpose of combating a disease, disorder or condition. The term is intended to include the full spectrum of treatments for a given disorder from which the patient is suffering, such as the delaying of the progression of the disease, disorder or condition, the alleviation or relief of symptoms and complications, the prevention of the disease and/or the cure or elimination of the disease, disorder or condition. The patient to be treated is preferably a mammal, in particular a human being.

The term "pharmaceutically acceptable salt" as used herein includes pharmaceutically acceptable acid addition salts, pharmaceutically acceptable base addition salts, pharmaceutically acceptable metal salts, ammonium salts, and alkylated ammonium salts. Acid addition salts include salts of inorganic acids as well as organic acids. Representative examples of suitable inorganic acids include hydrochloric, hydrobromic, hydroiodic, phosphoric, sulfuric, and nitric acids. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, and ketoglutarates. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, and calcium salts. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, and guanidine. Examples of cationic amino acids include lysine, arginine, and histidine.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, and magnesium hydroxide, in solvents such as ether, THF, methanol, t-butanol, dioxane, isopropanol, ethanol etc. Mixture of solvents may be used. Organic bases such as lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, and tartaric acid in solvents such as ethyl acetate, ether, alcohols, acetone, THF, dioxane etc. Mixture of solvents may also be used.

The term "combination therapy", "combined", "in combination with", and the like, as used herein refers to the administration of a single pharmaceutical dosage formulation which comprises the glucokinase activator compound of the present invention and another active agent(s), as well as administration of each active agent(s) in its own separate pharmaceutical dosage formulation. Where separate dosage formulations are used, the compound of the present invention and another active agent(s) can be administered to the patient at essentially the same time, i.e. concurrently, or at separate staggered times, i.e. sequentially. When given by different dosage formulations, the route of administration may be the same or different for each agent. Any route of administration known or contemplated for the individual agents is acceptable for the practice of the present invention.

The present invention provides a novel compound wherein the compound is selected from the following:

3-{2-[3-[2-(2-Chloro-benzyloxy)-ethyl]-3-(trans-4-methyl-cyclohexyl)-ureido]-thiazol-5-ylsulfanyl}-2,2-dimethyl-propionic acid;

3-{2-[3-(2-Benzyloxy-ethyl)-3-(trans-4-methyl-cyclohexyl)-ureido]-thiazol-5-ylsulfanyl}-2,2-dimethyl-propionic acid;

2-{2-[3-(2-Benzyloxy-ethyl)-3-(trans-4-methyl-cyclohexyl)-ureido]-thiazol-5-ylsulfanyl}-2-methyl-propionic acid;

2-{2-[3-[3-(2-Methoxy-phenylsulfanyl)-propyl]-3-(trans-4-methyl-cyclohexyl)-ureido]-thiazol-5-ylsulfanyl}-2-methyl-propionic acid;

2-Methyl-2-{2-[3-(trans-4-methyl-cyclohexyl)-3-(4-phenyl-butyl)-ureido]-thiazol-5-ylsulfanyl}-propionic acid;

2-{2-[3-[2-(4-Methoxy-phenyl)-ethyl]-3-(trans-4-methyl-cyclohexyl)-ureido]-thiazol-5-ylsulfanyl}-2-methyl-propionic acid;

3-{2-[3-[2-(4-Methoxy-phenyl)-ethyl]-3-(trans-4-methyl-cyclohexyl)-ureido]-thiazol-5-ylsulfanyl}-2,2-dimethyl-propionic acid;

{2-[3-(trans-4-Methyl-cyclohexyl)-3-(2-phenylsulfanyl-ethyl)-ureido]-thiazol-5-ylsulfanyl}-acetic acid;

2-Methyl-2-{2-[3-(trans-4-methyl-cyclohexyl)-3-(2-phenylsulfanyl-ethyl)-ureido]-thiazol-5-ylsulfanyl}-propionic acid;

{2-[3-(2-Benzylsulfanyl-ethyl)-3-(trans-4-methyl-cyclohexyl)-ureido]-thiazol-5-ylsulfanyl}-acetic acid;

{2-[3-(trans-4-Methyl-cyclohexyl)-3-(3-phenylsulfanyl-propyl)-ureido]-thiazol-5-ylsulfanyl}-acetic acid;

2-Methyl-2-{2-[3-(trans-4-methyl-cyclohexyl)-3-(3-phenylsulfanyl-propyl)-ureido]-thiazol-5-ylsulfanyl}-propionic acid;

2,2-Dimethyl-3-{2-[3-(trans-4-methyl-cyclohexyl)-3-(3-phenylsulfanyl-propyl)-ureido]-thiazol-5-ylsulfanyl}-propionic acid;

2-Methyl-2-{2-[3-(trans-4-methyl-cyclohexyl)-3-(3-phenoxy-propyl)-ureido]-thiazol-5-ylsulfanyl}-propionic acid;

2,2-Dimethyl-3-{2-[3-(trans-4-methyl-cyclohexyl)-3-(3-phenoxy-propyl)-ureido]-thiazol-5-ylsulfanyl}-propionic acid;

{2-[3-(trans-4-Methyl-cyclohexyl)-3-(4-phenyl-butyl)-ureido]-thiazol-5-ylsulfanyl}-acetic acid;

2-{2-[3-(2-Indan-2-yl-ethyl)-3-(trans-4-methyl-cyclohexyl)-ureido]-thiazol-5-ylsulfanyl}-2-methyl-propionic acid;

{2-[3-(2-Indan-2-yl-ethyl)-3-(trans-4-methyl-cyclohexyl)-ureido]-thiazol-5-ylsulfanyl}-acetic acid;

2,2-Dimethyl-3-{2-[3-(3-methyl-butyl)-3-(4-trans-methyl-cyclohexyl)-ureido]-thiazol-5-ylsulfanyl}-propionic acid;

3-{2-[3-(trans-4-Methyl-cyclohexyl)-3-(3-phenylsulfanyl-propyl)-ureido]-thiazol-5-ylsulfanyl}-propionic acid;

2,2-Dimethyl-3-{2-[3-(trans-4-methyl-cyclohexyl)-3-(t-phenyl-butyl)-ureido]-thiazol-5-ylsulfanyl}-propionic acid;

{2-[3-[2-(4-Methoxy-phenyl)-ethyl]-3-(trans-4-methyl-cyclohexyl)-ureido]-thiazole-5-sulfanyl}-acetic acid;

{2-[3-(2-Benzyloxy-ethyl)-3-(trans-4-methyl-cyclohexyl)-ureido]-thiazole-5-sulfanyl}-acetic acid;

2-{2-[3-[2-(4-Fluoro-2-trifluoromethyl-benzyloxy)-ethyl]-3-(trans-4-methyl-cyclohexyl)-ureido]-thiazol-5-ylsulfanyl}-2-methyl-propionic acid;

2-{2-[3-[2-(2-Chloro-4-fluoro-benzyloxy)-ethyl]-3-(trans-4-methyl-cyclohexyl)-ureido]-thiazol-5-ylsulfanyl}-2-methyl-propionic acid;

2-Methyl-2-(2-{3-(trans-4-methyl-cyclohexyl)-3-[2-(2-trifluoromethyl-benzyloxy)-ethyl]-ureido}thiazol-5-ylsulfanyl)-propionic acid;

2-{2-[3-[2-(2,4-Difluoro-benzyloxy)-ethyl]-3-(trans-4-methyl-cyclohexyl)-ureido]-thiazol-5-ylsulfanyl}-2-methyl-propionic acid;
2-Methyl-2-{2-[3-[2-(2-methyl-benzyloxy)-ethyl]-3-(trans-4-methyl-cyclohexyl)-ureido]-thiazol-5-ylsulfanyl}-propionic acid;
3-{2-[3-[2-(4-Fluoro-2-trifluoromethyl-benzyloxy)-ethyl]-3-(trans-4-methyl-cyclohexyl)-ureido]-thiazol-5-ylsulfanyl}-2,2-dimethyl-propionic acid;
3-{2-[3-[2-(2-Chloro-4-fluoro-benzyloxy)-ethyl]-3-(trans-4-methyl-cyclohexyl)-ureido]-thiazol-5-ylsulfanyl}-2,2-dimethyl-propionic acid;
2-Methyl-2-{2-[3-(trans-4-methyl-cyclohexyl)-3-phenethyl-ureido]-thiazol-5-ylsulfanyl}-propionic acid;
2,2-Dimethyl-3-{2-[3-(trans-4-methyl-cyclohexyl)-3-phenethyl-ureido]-thiazol-5-ylsulfanyl}-propionic acid;
3-{2-[3-[2-(2-Fluoro-benzyloxy)-ethyl]-3-(trans-4-methyl-cyclohexyl)-ureido]-thiazol-5-ylsulfanyl}-2,2-dimethyl-propionic acid;
3-{2-[3-[2-(2,4-Difluoro-benzyloxy)-ethyl]-3-(trans-4-methyl-cyclohexyl)-ureido]-thiazol-5-ylsulfanyl}-2,2-dimethyl-propionic acid;
2,2-Dimethyl-3-{2-[3-[2-(2-methyl-benzyloxy)-ethyl]-3-(trans-4-methyl-cyclohexyl)-ureido]-thiazol-5-ylsulfanyl}-propionic acid;
2-Methyl-2-(2-{3-(trans-4-methyl-cyclohexyl)-3-[2-(4-trifluoromethoxy-phenyl)-ethyl]-ureido}thiazol-5-ylsulfanyl)-propionic acid;
2-{2-[3-[2-(4-Chloro-phenyl)-ethyl]-3-(trans-4-methyl-cyclohexyl)-ureido]-thiazol-5-ylsulfanyl}2-methyl-propionic acid;
2-Methyl-2-{2-[3-(trans-4-methyl-cyclohexyl)-3-(3-phenyl-propyl)-ureido]-thiazol-5-ylsulfanyl}-propionic acid;
2,2-Dimethyl-3-(2-{3-(trans-4-methyl-cyclohexyl)-3-[2-(2-trifluoromethyl-benzyloxy)-ethyl]-ureido}-thiazol-5-ylsulfanyl)-propionic acid;
2-{2-[3-[2-(2-Difluoromethoxy-benzyloxy)-ethyl]-3-(trans-4-methyl-cyclohexyl)-ureido]-thiazol-5-ylsulfanyl}-2-methyl-propionic acid;
2-{2-[3-[2-(3-Fluoro-4-methoxy-phenyl)-ethyl]-3-(trans-4-methyl-cyclohexyl)-ureido]-thiazol-5-ylsulfanyl}-2-methyl-propionic acid;
2-{2-[3-[2-(3-Chloro-5-fluoro-phenyl)-ethyl]-3-(trans-4-methyl-cyclohexyl)-ureido]-thiazol-5-ylsulfanyl}-2-methyl-propionic acid;
2-Methyl-2-(2-{3-(trans-4-methyl-cyclohexyl)-3-[3-(3-trifluoromethyl-phenylsulfanyl)-propyl]-ureido}-thiazol-5-ylsulfanyl)-propionic acid;
2-{2-[3-[3-(2-Chloro-phenylsulfanyl)-propyl]-3-(trans-4-methyl-cyclohexyl)-ureido]-thiazol-5-ylsulfanyl}-2-methyl-propionic acid;
2-{2-[3-[2-(3,5-Difluoro-phenyl)-ethyl]-3-(trans-4-methyl-cyclohexyl)-ureido]-thiazol-5-ylsulfanyl}-2-methyl-propionic acid;
2-Methyl-2-{2-[3-(trans-4-methyl-cyclohexyl)-3-(2-p-tolyl-ethyl)-ureido]-thiazol-5-ylsulfanyl}-propionic acid;
2-{2-[3-[3-(4-Chloro-phenylsulfanyl)-propyl]-3-(trans-4-methyl-cyclohexyl)-ureido]-thiazol-5-ylsulfanyl}-2-methyl-propionic acid;
2-{2-[3-[3-(3-Chloro-phenylsulfanyl)-propyl]-3-(trans-4-methyl-cyclohexyl)-ureido]-thiazol-5-ylsulfanyl}-2-methyl-propionic acid;
2-{2-[3-[3-(4-Methoxy-phenylsulfanyl)-propyl]-3-(trans-4-methyl-cyclohexyl)-ureido]-thiazol-5-ylsulfanyl}-2-methyl-propionic acid;
2-{2-[3-[3-(3-Methoxy-phenylsulfanyl)-propyl]-3-(trans-4-methyl-cyclohexyl)-ureido]-thiazol-5-ylsulfanyl}-2-methyl-propionic acid;
2-{2-[3-[3-(2-Fluoro-phenylsulfanyl)-propyl]-3-(trans-4-methyl-cyclohexyl)-ureido]-thiazol-5-ylsulfanyl}-2-methyl-propionic acid;
2-{2-[3-[3-(4-Fluoro-phenylsulfanyl)-propyl]-3-(trans-4-methyl-cyclohexyl)-ureido]-thiazol-5-ylsulfanyl}-2-methyl-propionic acid;
2-Methyl-2-(2-{3-(trans-4-methyl-cyclohexyl)-3-[3-(2-trifluoromethoxy-phenylsulfanyl)-propyl]-ureido}-thiazol-5-ylsulfanyl)-propionic acid;
2-Methyl-2-(2-{3-(trans-4-methyl-cyclohexyl)-3-[3-(4-trifluoromethoxy-phenylsulfanyl)-propyl]-ureido}-thiazol-5-ylsulfanyl)-propionic acid;
2-{2-[3-[3-(3-Fluoro-phenylsulfanyl)-propyl]-3-(trans-4-methyl-cyclohexyl)-ureido]-thiazol-5-ylsulfanyl}-2-methyl-propionic acid;
{2-[3-(trans-4-Methyl-cyclohexyl)-3-(oxo-3-phenyl-propyl)-ureido]-thiazol-5-ylsulfanyl}-acetic acid;
{2-[-3-[3-(4-Methoxy-phenyl)-propyl]-3-(4-methyl-cyclohexyl)-ureido]-thiazol-5-ylsulfanyl}-acetic acid;
{2-[-3-[3-(3-Methoxy-phenyl)-propyl]-3-(4-methyl-cyclohexyl)-ureido]-thiazol-5-ylsulfanyl}-acetic acid;
{2-[3-Benzyl-3-(trans-4-methyl-cyclohexyl)-ureido]-thiazol-5-ylsulfanyl}-acetic acid;
(2-{3-(trans-4-Methyl-cyclohexyl)-3-[2-(toluene-4-sulfonyl)-ethyl]-ureido}-thiazol-5-ylsulfanyl)-acetic acid;
{2-[-3-(3-Cyclohexyl-propyl)-3-(trans-4-methyl-cyclohexyl)-ureido]-thiazol-5-ylsulfanyl}-acetic acid;
(2-{-3-(trans-4-Methyl-cyclohexyl)-3-[3-(3-trifluoromethyl-phenyl)-propyl]-ureido}-thiazol-5-ylsulfanyl)-acetic acid;
{2-[-3-[3-(4-Chloro-phenyl)-propyl]-3-(trans-4-methyl-cyclohexyl)-ureido]-thiazol-5-ylsulfanyl}-acetic acid;
{2-[-3-[3-(3-Chloro-phenyl)-propyl]-3-(trans-4-methyl-cyclohexyl)-ureido]-thiazol-5-ylsulfanyl}-acetic acid;
{2-[3-[4-(4-Methoxy-phenyl)-butyl]-3-(4-methyl-cyclohexyl)-ureido]-thiazol-5-ylsulfanyl}-acetic acid;
{2-[3-(4-Methyl-cyclohexyl)-3-(4-p-tolyl-butyl)-ureido]-thiazol-5-ylsulfanyl}-acetic acid;
{2-[-3-[3-(4-Fluoro-phenyl)-propyl]-3-(trans-4-methyl-cyclohexyl)-ureido]-thiazol-5-ylsulfanyl}-acetic acid;
{2-[3-[3-(5-Chloro-benzofuran-3-yl)-propyl]-3-(trans-4-methyl-cyclohexyl)-ureido]-thiazol-5-ylsulfanyl}-acetic acid;
{2-[3-[4-(4-Chloro-phenyl)-butyl]-3-(trans-4-methyl-cyclohexyl)-ureido]-thiazol-5-ylsulfanyl}-acetic acid;
{2-[3-(trans-4-Methyl-cyclohexyl)-3-(3-pyridin-3-yl-propyl)-ureido]-thiazol-5-ylsulfanyl}-acetic acid;
{2-[-3-(trans-4-Methyl-cyclohexyl)-3-(trans-2-phenyl-cyclopropylmethyl)-ureido]-thiazol-5-ylsulfanyl}-acetic acid;
{2-[3-(2-Methanesulfonyl-ethyl)-3-(trans-4-methyl-cyclohexyl)-ureido]-thiazol-5-ylsulfanyl}-acetic acid;
{2-[3-Benzo[1,3]dioxol-5-ylmethyl-3-(trans-4-methyl-cyclohexyl)-ureido]-thiazol-5-ylsulfanyl}-acetic acid;
{2-[3-[4-(1H-Indol-3-yl)-butyl]-3-(trans-4-methyl-cyclohexyl)-ureido]-thiazol-5-ylsulfanyl}-acetic acid;
{2-[3-(4-Cyclohexyl-butyl)-3-(trans-4-methyl-cyclohexyl)-ureido]-thiazol-5-ylsulfanyl}-acetic acid;
{2-[3-[4-(4-Fluoro-phenyl)-4-hydroxy-butyl]-3-(trans-4-methyl-cyclohexyl)-ureido]-thiazol-5-ylsulfanyl}-acetic acid;
{2-[3-[4-(3-Fluoro-4-methoxy-phenyl)-4-hydroxy-butyl]-3-(trans-4-methyl-cyclohexyl)-ureido]-thiazol-5-ylsulfanyl}-acetic acid;

{2-[3-(trans-4-Methyl-cyclohexyl)-3-(1,2,3,4-tetrahydro-naphthalen-2-ylmethyl)-ureido]-thiazol-5-ylsulfanyl}-acetic acid;

2-{2-[3-[2-(4-Acetyl-phenyl)-ethyl]-3-(trans-4-methyl-cyclohexyl)-ureido]-thiazol-5-ylsulfanyl}-2-methyl-propionic acid;

{2-[3-[3-(1H-Indol-3-yl)-propyl]-3-(trans-4-methyl-cyclohexyl)-ureido]-thiazol-5-ylsulfanyl}-acetic acid;

{2-[3-[4-(3,4-Dimethoxy-phenyl)-butyl]-3-(trans-4-methyl-cyclohexyl)-ureido]-thiazol-5-ylsulfanyl}-acetic acid;

{2-[3-(trans-4-Methyl-cyclohexyl)-3-(2-methyl-2-phenyl-propyl)-ureido]-thiazol-5-ylsulfanyl}-acetic acid;

{2-[3-(2,2-Difluoro-2-phenyl-ethyl)-3-(trans-4-methyl-cyclohexyl)-ureido]-thiazol-5-ylsulfanyl}-acetic acid;

{2-[3-(But-3-ynyl)-3-(trans-4-methyl-cyclohexyl)-ureido]-thiazol-5-ylsulfanyl}-acetic acid;

{2-[3-(Trans-4-methoxy-cyclohexyl)-3-phenethyl-ureido]-thiazol-5-ylsulfanyl}-acetic acid;

{2-[3-(2-Benzyloxy-ethyl)-3-(trans-4-methoxy-cyclohexyl)-ureido]-thiazol-5-ylsulfanyl}-acetic acid;

2-{2-[3-[2-(3-Chloro-phenyl)-ethyl]-3-(trans-4-methyl-cyclohexyl)-ureido]-thiazol-5-ylsulfanyl}-2-methyl-propionic acid;

2-{2-[3-[2-(3-Chloro-phenyl)-ethyl]-3-(trans-4-methyl-cyclohexyl)-ureido]-thiazol-5-ylsulfanyl}-2-methyl-propionic acid;

2-{2-[3-[2-(3-Methoxy-phenyl)-ethyl]-3-(trans-4-methyl-cyclohexyl)-ureido]-thiazol-5-ylsulfanyl}-2-methyl-propionic acid;

2-{2-[3-[2-(3,4-Dimethoxy-phenyl)-ethyl]-3-(trans-4-methyl-cyclohexyl)-ureido]-thiazol-5-ylsulfanyl}-2-methyl-propionic acid;

{2-[3-(2-Cyano-ethyl)-3-(trans-4-methyl-cyclohexyl)-ureido]-thiazol-5-ylsulfanyl}-acetic acid;

{2-[3-(trans-4-Methyl-cyclohexyl)-3-pyridin-4-ylmethyl-ureido]-thiazol-5-ylsulfanyl}-acetic acid;

{2-[3-(trans-4-Methyl-cyclohexyl)-3-pyridin-2-ylmethyl-ureido]-thiazol-5-ylsulfanyl}-acetic acid;

{2-[3-(trans-4-Methyl-cyclohexyl)-3-pyridin-3-ylmethyl-ureido]-thiazol-5-ylsulfanyl}-acetic acid;

{2-[3-[4-(4-Methanesulfonyl-phenyl)-but-3-ynyl]-3-(trans-4-methyl-cyclohexyl)-ureido]-thiazol-5-ylsulfanyl}-acetic acid;

{2-[3-(trans-4-Methyl-cyclohexyl)-3-(4-phenyl-but-3-ynyl)-ureido]-thiazol-5-ylsulfanyl}-acetic acid;

1-{2-[3-[2-(2-Chloro-benzyloxy)-ethyl]-3-(trans-4-methyl-cyclohexyl)-ureido]-thiazol-5-ylsulfanyl}-cyclobutanecarboxylic acid;

1-{2-[3-[2-(2-Chloro-benzyloxy)-ethyl]-3-(trans-4-methyl-cyclohexyl)-ureido]-thiazol-5-ylsulfanyl}-cyclohexanecarboxylic acid;

1-{2-[3-(trans-4-Methyl-cyclohexyl)-3-(4-phenyl-butyl)-ureido]-thiazol-5-ylsulfanyl}-cyclobutanecarboxylic acid;

1-{2-[3-(trans-4-Methyl-cyclohexyl)-3-(4-phenyl-butyl)-ureido]-thiazol-5-ylsulfanyl}-cyclohexanecarboxylic acid;

1-{2-[3-[2-(trans-4-Methoxy-phenyl)-ethyl]-3-(4-methyl-cyclohexyl)-ureido]-thiazol-5-ylsulfanyl}-cyclobutanecarboxylic acid;

1-{2-[3-[2-(4-Methoxy-phenyl)-ethyl]-3-(trans-4-methyl-cyclohexyl)-ureido]-thiazol-5-ylsulfanyl}-cyclohexanecarboxylic acid;

2-{2-[3-[2-(4-Fluoro-phenyl)-ethyl]-3-(trans-4-methyl-cyclohexyl)-ureido]-thiazol-5-ylsulfanyl}-2-methyl-propionic acid;

2-{2-[3-[2-(2,3-Dihydro-benzofuran-6-yl)-ethyl]-3-(trans-4-methyl-cyclohexyl)-ureido]-thiazol-5-ylsulfanyl}-2-methyl-propionic acid;

2-{2-[3-[2-(3-Fluoro-phenyl)-ethyl]-3-(trans-4-methyl-cyclohexyl)-ureido]-thiazol-5-ylsulfanyl}-2-methyl-propionic acid;

2-{2-[3-[2-(1,3-Benzodioxol-5-yl-ethyl]-3-(trans-4-methyl-cyclohexyl)-ureido]-thiazol-5-ylsulfanyl}-2-methyl-propionic acid;

(2-{3-(trans-4-Methyl-cyclohexyl)-3-[2-(pyridin-3-yl-methoxy)-ethyl]-ureido}-thiazol-5-ylsulfanyl)-acetic acid;

(2-{3-(trans-4-Methyl-cyclohexyl)-3-[2-(pyridin-2-yl-methoxy)-ethyl]-ureido}-thiazol-5-ylsulfanyl)-acetic acid;

(2-{3-(trans-4-Methyl-cyclohexyl)-3-[2-(pyridin-4-yl-methoxy)-ethyl]-ureido}-thiazol-5-ylsulfanyl)-acetic acid;

{2-[3-(2-Cyclopropylmethoxy-ethyl)-3-(trans-4-methyl-cyclohexyl)-ureido]-thiazol-5-ylsulfanyl}-acetic acid;

{2-[3-[2-(5-Chloro-benzo[b]thiophen-3-ylmethoxy)-ethyl]-3-(trans-4-methyl-cyclohexyl)-ureido]-thiazol-5-ylsulfanyl}-acetic acid;

{2-[3-(trans-4-Methyl-cyclohexyl)-3-(5-phenyl-pentyl)-ureido]-thiazol-5-ylsulfanyl}-acetic acid;

2-{2-[3-[3-(3-Methoxy-phenyl)-propyl]-3-(trans-4-methyl-cyclohexyl)-ureido]-thiazol-5-ylsulfanyl}-2-methyl-propionic acid;

2-{2-[3-[3-(3-Chloro-phenyl)-propyl]-3-(trans-4-methyl-cyclohexyl)-ureido]-thiazol-5-ylsulfanyl}-2-methyl-propionic acid;

2-{2-[3-[3-(4-Fluoro-phenyl)-propyl]-3-(trans-4-methyl-cyclohexyl)-ureido]-thiazol-5-ylsulfanyl}-2-methyl-propionic acid;

2-Methyl-2-{2-[3-(trans-4-methyl-cyclohexyl)-3-(4-p-tolyl-butyl)-ureido]-thiazol-5-ylsulfanyl}-propionic acid;

2-{2-[3-[4-(4-Methoxy-phenyl)-butyl]-3-(trans-4-methyl-cyclohexyl)-ureido]-thiazol-5-ylsulfanyl}-2-methyl-propionic acid;

2-{2-[3-[4-(4-Methoxy-phenyl)-butyl]-3-(trans-4-methyl-cyclohexyl)-ureido]-thiazol-5-ylsulfanyl}-2-methyl-propionic acid;

{2-[3-(trans-4-Methoxy-cyclohexyl)-3-(3-phenyl-propyl)-ureido]-thiazol-5-ylsulfanyl}-acetic acid;

{2-[3-(Trans-4-methoxy-cyclohexyl)-3-(4-phenyl-butyl)-ureido]-thiazol-5-ylsulfanyl}-acetic acid;

2-{2-[3-[4-(4-Chloro-phenyl)-butyl]-3-(trans-4-methyl-cyclohexyl)-ureido]-thiazol-5-ylsulfanyl}-2-methyl-propionic acid;

2-Methyl-2-{2-[3-(trans-4-methyl-cyclohexyl)-3-(3-pyridin-3-yl-propyl)-ureido]-thiazol-5-ylsulfanyl}-propionic acid;

2-{2-[3-[3-(1H-Indol-3-yl)-propyl]-3-(trans-4-methyl-cyclohexyl)-ureido]-thiazol-5-ylsulfanyl}-2-methyl-propionic acid;

2-{2-[3-[4-(3,4-Dimethoxy-phenyl)-butyl]-3-(trans-4-methyl-cyclohexyl)-ureido]-thiazol-5-ylsulfanyl}-2-methyl-propionic acid;

2-Methyl-2-(2-{3-(4-methyl-cyclohexyl)-3-[2-(trans-4-methylsulfanyl-phenyl)-ethyl]-ureido}-thiazol-5-ylsulfanyl)-propionic acid;

2-{2-[3-[2-(4-Isopropyl-phenyl)-ethyl]-3-(trans-4-methyl-cyclohexyl)-ureido]-thiazol-5-ylsulfanyl}-2-methyl-propionic acid;

2-Methyl-2-(2-{3-(trans-4-methyl-cyclohexyl)-3-[2-(3,4,5-trifluoro-phenyl)-ethyl]-ureido}-thiazol-5-ylsulfanyl)-propionic acid;

2-Methyl-2-(2-{3-(trans-4-methyl-cyclohexyl)-3-[2-(2,3,4-trifluoro-phenyl)-ethyl]-ureido}-thiazol-5-ylsulfanyl)-propionic acid;

2-{2-[3-[2-(2-Fluoro-4-methoxy-phenyl)-ethyl]-3-(trans-4-methyl-cyclohexyl)-ureido]-thiazol-5-ylsulfanyl}-2-methyl-propionic acid;

2-{2-[3-[2-(3-Fluoro-4-trifluoromethoxy-phenyl)-ethyl]-3-(trans-4-methyl-cyclohexyl)-ureido]-thiazol-5-ylsulfanyl}-2-methyl-propionic acid;

2-{2-[3-[2-(3,5-Difluoro-4-methoxy-phenyl)-ethyl]-3-(trans-4-methyl-cyclohexyl)-ureido]-thiazol-5-ylsulfanyl}-2-methyl-propionic acid;

2-{2-[3-[2-(4-Methoxy-3-methyl-phenyl)-ethyl]-3-(trans-4-methyl-cyclohexyl)-ureido]-thiazol-5-ylsulfanyl}-2-methyl-propionic acid;

2-{2-[3-[2-(2,3-Difluoro-4-methoxy-phenyl)-ethyl]-3-(trans-4-methyl-cyclohexyl)-ureido]-thiazol-5-ylsulfanyl}-2-methyl-propionic acid;

or a pharmaceutically acceptable salt thereof.

In one embodiment the present invention provides a novel compound wherein the compound is selected from the following:

3-{2-[3-[2-(2-Chloro-benzyloxy)-ethyl]-3-(trans-4-methyl-cyclohexyl)-ureido]-thiazol-5-ylsulfanyl}-2,2-dimethyl-propionic acid;

3-{2-[3-(2-Benzyloxy-ethyl)-3-(trans-4-methyl-cyclohexyl)-ureido]-thiazol-5-ylsulfanyl}-2,2-dimethyl-propionic acid;

2-{2-[3-(2-Benzyloxy-ethyl)-3-(trans-4-methyl-cyclohexyl)-ureido]-thiazol-5-ylsulfanyl}-2-methyl-propionic acid;

2-{2-[3-[3-(2-Methoxy-phenylsulfanyl)-propyl]-3-(trans-4-methyl-cyclohexyl)-ureido]-thiazol-5-ylsulfanyl}-2-methyl-propionic acid;

2-Methyl-2-{2-[3-(trans-4-methyl-cyclohexyl)-3-(4-phenyl-butyl)-ureido]-thiazol-5-ylsulfanyl}-propionic acid;

2-{2-[3-[2-(4-Methoxy-phenyl)-ethyl]-3-(trans-4-methyl-cyclohexyl)-ureido]-thiazol-5-ylsulfanyl}-2-methyl-propionic acid;

3-{2-[3-[2-(4-Methoxy-phenyl)-ethyl]-3-(trans-4-methyl-cyclohexyl)-ureido]-thiazol-5-ylsulfanyl}-2,2-dimethyl-propionic acid;

{2-[3-(trans-4-Methyl-cyclohexyl)-3-(2-phenylsulfanyl-ethyl)-ureido]-thiazol-5-ylsulfanyl}-acetic acid;

2-Methyl-2-{2-[3-(trans-4-methyl-cyclohexyl)-3-(2-phenylsulfanyl-ethyl)-ureido]-thiazol-5-ylsulfanyl}-propionic acid;

{2-[3-(2-Benzylsulfanyl-ethyl)-3-(trans-4-methyl-cyclohexyl)-ureido]-thiazol-5-ylsulfanyl}-acetic acid;

{2-[3-(trans-4-Methyl-cyclohexyl)-3-(3-phenylsulfanyl-propyl)-ureido]-thiazol-5-ylsulfanyl}-acetic acid;

2-Methyl-2-{2-[3-(trans-4-methyl-cyclohexyl)-3-(3-phenylsulfanyl-propyl)-ureido]-thiazol-5-ylsulfanyl}-propionic acid;

2,2-Dimethyl-3-{2-[3-(trans-4-methyl-cyclohexyl)-3-(3-phenylsulfanyl-propyl)-ureido]-thiazol-5-ylsulfanyl}-propionic acid;

2-Methyl-2-{2-[3-(trans-4-methyl-cyclohexyl)-3-(3-phenoxy-propyl)-ureido]-thiazol-5-ylsulfanyl}-propionic acid;

2,2-Dimethyl-3-{2-[3-(trans-4-methyl-cyclohexyl)-3-(3-phenoxy-propyl)-ureido]-thiazol-5-ylsulfanyl}-propionic acid;

{2-[3-(trans-4-Methyl-cyclohexyl)-3-(4-phenyl-butyl)-ureido]-thiazol-5-ylsulfanyl}-acetic acid;

2-{2-[3-(2-Indan-2-yl-ethyl)-3-(trans-4-methyl-cyclohexyl)-ureido]-thiazol-5-ylsulfanyl}-2-methyl-propionic acid;

{2-[3-(2-Indan-2-yl-ethyl)-3-(trans-4-methyl-cyclohexyl)-ureido]-thiazol-5-ylsulfanyl}-acetic acid;

2,2-Dimethyl-3-{2-[3-(3-methyl-butyl)-3-(4-trans-methyl-cyclohexyl)-ureido]-thiazol-5-ylsulfanyl}-propionic acid;

3-{2-[3-(trans-4-Methyl-cyclohexyl)-3-(3-phenylsulfanyl-propyl)-ureido]-thiazol-5-ylsulfanyl}-propionic acid;

2,2-Dimethyl-3-{2-[3-(trans-4-methyl-cyclohexyl)-3-(t-phenyl-butyl)-ureido]-thiazol-5-ylsulfanyl}-propionic acid;

{2-[3-[2-(4-Methoxy-phenyl)-ethyl]-3-(trans-4-methyl-cyclohexyl)-ureido]-thiazole-5-sulfanyl}-acetic acid;

{2-[3-(2-Benzyloxy-ethyl)-3-(trans-4-methyl-cyclohexyl)-ureido]-thiazole-5-sulfanyl}-acetic acid;

2-{2-[3-[2-(4-Fluoro-2-trifluoromethyl-benzyloxy)-ethyl]-3-(trans-4-methyl-cyclohexyl)-ureido]-thiazol-5-ylsulfanyl}-2-methyl-propionic acid;

2-{2-[3-[2-(2-Chloro-4-fluoro-benzyloxy)-ethyl]-3-(trans-4-methyl-cyclohexyl)-ureido]-thiazol-5-ylsulfanyl}-2-methyl-propionic acid;

2-Methyl-2-(2-{3-(trans-4-methyl-cyclohexyl)-3-[2-(2-trifluoromethyl-benzyloxy)-ethyl]-ureido}-thiazol-5-ylsulfanyl)-propionic acid;

2-{2-[3-[2-(2,4-Difluoro-benzyloxy)-ethyl]-3-(trans-4-methyl-cyclohexyl)-ureido]-thiazol-5-ylsulfanyl}-2-methyl-propionic acid;

2-Methyl-2-{2-[3-[2-(2-methyl-benzyloxy)-ethyl]-3-(trans-4-methyl-cyclohexyl)-ureido]-thiazol-5-ylsulfanyl}-propionic acid;

3-{2-[3-[2-(4-Fluoro-2-trifluoromethyl-benzyloxy)-ethyl]-3-(trans-4-methyl-cyclohexyl)-ureido]-thiazol-5-ylsulfanyl}-2,2-dimethyl-propionic acid;

3-{2-[3-[2-(2-Chloro-4-fluoro-benzyloxy)-ethyl]-3-(trans-4-methyl-cyclohexyl)-ureido]-thiazol-5-ylsulfanyl}-2,2-dimethyl-propionic acid;

2-Methyl-2-{2-[3-(trans-4-methyl-cyclohexyl)-3-phenethyl-ureido]-thiazol-5-ylsulfanyl}-propionic acid;

2,2-Dimethyl-3-{2-[3-(trans-4-methyl-cyclohexyl)-3-phenethyl-ureido]-thiazol-5-ylsulfanyl}-propionic acid;

3-{2-[3-[2-(2-Fluoro-benzyloxy)-ethyl]-3-(trans-4-methyl-cyclohexyl)-ureido]-thiazol-5-ylsulfanyl}-2,2-dimethyl-propionic acid;

3-{2-[3-[2-(2,4-Difluoro-benzyloxy)-ethyl]-3-(trans-4-methyl-cyclohexyl)-ureido]-thiazol-5-ylsulfanyl}-2,2-dimethyl-propionic acid;

2,2-Dimethyl-3-{2-[3-[2-(2-methyl-benzyloxy)-ethyl]-3-(trans-4-methyl-cyclohexyl)-ureido]-thiazol-5-ylsulfanyl}-propionic acid;

2-Methyl-2-(2-{3-(trans-4-methyl-cyclohexyl)-3-[2-(4-trifluoromethoxy-phenyl)-ethyl]-ureido}-thiazol-5-ylsulfanyl)-propionic acid;

2-{2-[3-[2-(4-Chloro-phenyl)-ethyl]-3-(trans-4-methyl-cyclohexyl)-ureido]-thiazol-5-ylsulfanyl}-2-methyl-propionic acid;

2-Methyl-2-{2-[3-(trans-4-methyl-cyclohexyl)-3-(3-phenyl-propyl)-ureido]-thiazol-5-ylsulfanyl}-propionic acid;

2,2-Dimethyl-3-(2-{3-(trans-4-methyl-cyclohexyl)-3-[2-(2-trifluoromethyl-benzyloxy)-ethyl]-ureido}-thiazol-5-ylsulfanyl)-propionic acid;

2-{2-[3-[2-(2-Difluoromethoxy-benzyloxy)-ethyl]-3-(trans-4-methyl-cyclohexyl)-ureido]-thiazol-5-ylsulfanyl}-2-methyl-propionic acid;

2-{2-[3-[2-(3-Fluoro-4-methoxy-phenyl)-ethyl]-3-(trans-4-methyl-cyclohexyl)-ureido]-thiazol-5-ylsulfanyl}-2-methyl-propionic acid;

2-{2-[3-[2-(3-Chloro-5-fluoro-phenyl)-ethyl]-3-(trans-4-methyl-cyclohexyl)-ureido]-thiazol-5-ylsulfanyl}-2-methyl-propionic acid;
2-Methyl-2-(2-{3-(trans-4-methyl-cyclohexyl)-3-[3-(3-trifluoromethyl-phenylsulfanyl)-propyl]-ureido}-thiazol-5-ylsulfanyl)-propionic acid;
2-{2-[3-[3-(2-Chloro-phenylsulfanyl)-propyl]-3-(trans-4-methyl-cyclohexyl)-ureido]-thiazol-5-ylsulfanyl}-2-methyl-propionic acid;
2-{2-[3-[2-(3,5-Difluoro-phenyl)-ethyl]-3-(trans-4-methyl-cyclohexyl)-ureido]-thiazol-5-ylsulfanyl}-2-methyl-propionic acid;
2-Methyl-2-{2-[3-(trans-4-methyl-cyclohexyl)-3-(2-p-tolyl-ethyl)-ureido]-thiazol-5-ylsulfanyl}-propionic acid;
2-{2-[3-[3-(4-Chloro-phenylsulfanyl)-propyl]-3-(trans-4-methyl-cyclohexyl)-ureido]-thiazol-5-ylsulfanyl}-2-methyl-propionic acid;
2-{2-[3-[3-(3-Chloro-phenylsulfanyl)-propyl]-3-(trans-4-methyl-cyclohexyl)-ureido]-thiazol-5-ylsulfanyl}-2-methyl-propionic acid;
2-{2-[3-[3-(4-Methoxy-phenylsulfanyl)-propyl]-3-(trans-4-methyl-cyclohexyl)-ureido]-thiazol-5-ylsulfanyl}-2-methyl-propionic acid;
2-{2-[3-[3-(3-Methoxy-phenylsulfanyl)-propyl]-3-(trans-4-methyl-cyclohexyl)-ureido]-thiazol-5-ylsulfanyl}-2-methyl-propionic acid;
2-{2-[3-[3-(2-Fluoro-phenylsulfanyl)-propyl]-3-(trans-4-methyl-cyclohexyl)-ureido]-thiazol-5-ylsulfanyl}-2-methyl-propionic acid;
2-{2-[3-[3-(4-Fluoro-phenylsulfanyl)-propyl]-3-(trans-4-methyl-cyclohexyl)-ureido]-thiazol-5-ylsulfanyl}-2-methyl-propionic acid;
2-Methyl-2-(2-{3-(trans-4-methyl-cyclohexyl)-3-[3-(2-trifluoromethoxy-phenylsulfanyl)-propyl]-ureido}-thiazol-5-ylsulfanyl)-propionic acid;
2-Methyl-2-(2-{3-(trans-4-methyl-cyclohexyl)-3-[3-(4-trifluoromethoxy-phenylsulfanyl)-propyl]-ureido}-thiazol-5-ylsulfanyl)-propionic acid;
2-{2-[3-[3-(3-Fluoro-phenylsulfanyl)-propyl]-3-(trans-4-methyl-cyclohexyl)-ureido]-thiazol-5-ylsulfanyl}-2-methyl-propionic acid;
{2-[3-(trans-4-Methyl-cyclohexyl)-3-(3-oxo-3-phenyl-propyl)-ureido]-thiazol-5-ylsulfanyl}-acetic acid;
{2-[-3-[3-(4-Methoxy-phenyl)-propyl]-3-(4-methyl-cyclohexyl)-ureido]-thiazol-5-ylsulfanyl}-acetic acid;
{2-[-3-[3-(3-Methoxy-phenyl)-propyl]-3-(4-methyl-cyclohexyl)-ureido]-thiazol-5-ylsulfanyl}-acetic acid;
{2-[3-Benzyl-3-(trans-4-methyl-cyclohexyl)-ureido]-thiazol-5-ylsulfanyl}-acetic acid;
(2-{3-(trans-4-Methyl-cyclohexyl)-3-[2-(toluene-4-sulfonyl)-ethyl]-ureido}-thiazol-5-ylsulfanyl)-acetic acid;
{2-[-3-(3-Cyclohexyl-propyl)-3-(trans-4-methyl-cyclohexyl)-ureido]-thiazol-5-ylsulfanyl}-acetic acid;
(2-{-3-(trans-4-Methyl-cyclohexyl)-3-[3-(3-trifluoromethyl-phenyl)-propyl]-ureido}-thiazol-5-ylsulfanyl)-acetic acid;
{2-[-3-[3-(4-Chloro-phenyl)-propyl]-3-(trans-4-methyl-cyclohexyl)-ureido]-thiazol-5-ylsulfanyl}-acetic acid;
{2-[3-[3-(3-Chloro-phenyl)-propyl]-3-(trans-4-methyl-cyclohexyl)-ureido]-thiazol-5-ylsulfanyl}-acetic acid;
{2-[3-[4-(4-Methoxy-phenyl)-butyl]-3-(4-methyl-cyclohexyl)-ureido]-thiazol-5-ylsulfanyl}-acetic acid;
{2-[3-(4-Methyl-cyclohexyl)-3-(4-p-tolyl-butyl)-ureido]-thiazol-5-ylsulfanyl}-acetic acid;
{2-[-3-[3-(4-Fluoro-phenyl)-propyl]-3-(trans-4-methyl-cyclohexyl)-ureido]-thiazol-5-ylsulfanyl}-acetic acid;
{2-[3-[3-(5-Chloro-benzofuran-3-yl)-propyl]-3-(trans-4-methyl-cyclohexyl)-ureido]-thiazol-5-ylsulfanyl}-acetic acid;
{2-[3-[4-(4-Chloro-phenyl)-butyl]-3-(trans-4-methyl-cyclohexyl)-ureido]-thiazol-5-ylsulfanyl}-acetic acid;
{2-[3-(trans-4-Methyl-cyclohexyl)-3-(3-pyridin-3-yl-propyl)-ureido]-thiazol-5-ylsulfanyl}-acetic acid;
{2[-3-(trans-4-Methyl-cyclohexyl)-3-(trans-2-phenyl-cyclopropylmethyl)-ureido]-thiazol-5-ylsulfanyl}-acetic acid;
{2-[3-(2-Methanesulfonyl-ethyl)-3-(trans-4-methyl-cyclohexyl)-ureido]-thiazol-5-ylsulfanyl}-acetic acid;
{2-[3-Benzo[1,3]dioxol-5-ylmethyl-3-(trans-4-methyl-cyclohexyl)-ureido]-thiazol-5-ylsulfanyl}-acetic acid;
{2-[3-[4-(1H-Indol-3-yl)-butyl]-3-(trans-4-methyl-cyclohexyl)-ureido]-thiazol-5-ylsulfanyl}-acetic acid;
{2-[3-(4-Cyclohexyl-butyl)-3-(trans-4-methyl-cyclohexyl)-ureido]-thiazol-5-ylsulfanyl}-acetic acid;
{2-[3-[4-(4-Fluoro-phenyl)-4-hydroxy-butyl]-3-(trans-4-methyl-cyclohexyl)-ureido]-thiazol-5-ylsulfanyl}-acetic acid;
{2-[3-[4-(3-Fluoro-4-methoxy-phenyl)-4-hydroxy-butyl]-3-(trans-4-methyl-cyclohexyl)-ureido]-thiazol-5-ylsulfanyl}-acetic acid;
{2-[3-(trans-4-Methyl-cyclohexyl)-3-(1,2,3,4-tetrahydro-naphthalen-2-ylmethyl)-ureido]-thiazol-5-ylsulfanyl}-acetic acid;
2-{2-[3-[2-(4-Acetyl-phenyl)-ethyl]-3-(trans-4-methyl-cyclohexyl)-ureido]-thiazol-5-ylsulfanyl}-2-methyl-propionic acid;
{2-[3-[3-(1H-Indol-3-yl)-propyl]-3-(trans-4-methyl-cyclohexyl)-ureido]-thiazol-5-ylsulfanyl}-acetic acid;
{2-[3-[4-(3,4-Dimethoxy-phenyl)-butyl]-3-(trans-4-methyl-cyclohexyl)-ureido]-thiazol-5-ylsulfanyl}-acetic acid;
{2-[3-(trans-4-Methyl-cyclohexyl)-3-(2-methyl-2-phenyl-propyl)-ureido]-thiazol-5-ylsulfanyl}-acetic acid;
{2-[3-(2,2-Difluoro-2-phenyl-ethyl)-3-(trans-4-methyl-cyclohexyl)-ureido]-thiazol-5-ylsulfanyl}-acetic acid;
{2-[3-(But-3-ynyl)-3-(trans-4-methyl-cyclohexyl)-ureido]-thiazol-5-ylsulfanyl}-acetic acid;
{2-[3-(Trans-4-methoxy-cyclohexyl)-3-phenethyl-ureido]-thiazol-5-ylsulfanyl}-acetic acid;
{2-[3-(2-Benzyloxy-ethyl)-3-(trans-4-methyl-cyclohexyl)-ureido]-thiazol-5-ylsulfanyl}-acetic acid;
2-{2-[3-[2-(3-Chloro-phenyl)-ethyl]-3-(trans-4-methyl-cyclohexyl)-ureido]-thiazol-5-ylsulfanyl}-2-methyl-propionic acid;
2-{2-[3-[2-(3-Chloro-phenyl)-ethyl]-3-(trans-4-methyl-cyclohexyl)-ureido]-thiazol-5-ylsulfanyl}-2-methyl-propionic acid;
2-{2-[3-[2-(3-Methoxy-phenyl)-ethyl]-3-(trans-4-methyl-cyclohexyl)-ureido]-thiazol-5-ylsulfanyl}-2-methyl-propionic acid;
2-{2-[3-[2-(3,4-Dimethoxy-phenyl)-ethyl]-3-(trans-4-methyl-cyclohexyl)-ureido]-thiazol-5-ylsulfanyl}-2-methyl-propionic acid;
{2-[3-(2-Cyano-ethyl)-3-(trans-4-methyl-cyclohexyl)-ureido]-thiazol-5-ylsulfanyl}-acetic acid;
{2-[3-(trans-4-Methyl-cyclohexyl)-3-pyridin-4-ylmethyl-ureido]-thiazol-5-ylsulfanyl}-acetic acid;
{2-[3-(trans-4-Methyl-cyclohexyl)-3-pyridin-2-ylmethyl-ureido]-thiazol-5-ylsulfanyl}-acetic acid;
{2-[3-(trans-4-Methyl-cyclohexyl)-3-pyridin-3-ylmethyl-ureido]-thiazol-5-ylsulfanyl}-acetic acid;
{2-[3-[4-(4-Methanesulfonyl-phenyl)-but-3-ynyl]-3-(trans-4-methyl-cyclohexyl)-ureido]-thiazol-5-ylsulfanyl}-acetic acid;

{2-[3-(trans-4-Methyl-cyclohexyl)-3-(4-phenyl-but-3-ynyl)-ureido]-thiazol-5-ylsulfanyl}-acetic acid;
1-{2-[3-[2-(2-Chloro-benzyloxy)-ethyl]-3-(trans-4-methyl-cyclohexyl)-ureido]-thiazol-5-ylsulfanyl}-cyclobutanecarboxylic acid;
1-{2-[3-[2-(2-Chloro-benzyloxy)-ethyl]-3-(trans-4-methyl-cyclohexyl)-ureido]-thiazol-5-ylsulfanyl}-cyclohexanecarboxylic acid;
1-{2-[3-(trans-4-Methyl-cyclohexyl)-3-(4-phenyl-butyl)-ureido]-thiazol-5-ylsulfanyl}-cyclobutanecarboxylic acid;
1-{2-[3-(trans-4-Methyl-cyclohexyl)-3-(4-phenyl-butyl)-ureido]-thiazol-5-ylsulfanyl}-cyclohexanecarboxylic acid;
1-{2-[3-[2-(trans-4-Methoxy-phenyl)-ethyl]-3-(4-methyl-cyclohexyl)-ureido]-thiazol-5-ylsulfanyl}-cyclobutanecarboxylic acid;
1-{2-[3-[2-(4-Methoxy-phenyl)-ethyl]-3-(trans-4-methyl-cyclohexyl)-ureido]-thiazol-5-ylsulfanyl}-cyclohexanecarboxylic acid;
2-{2-[3-[2-(4-Fluoro-phenyl)-ethyl]-3-(trans-4-methyl-cyclohexyl)-ureido]-thiazol-5-ylsulfanyl}-2-methyl-propionic acid;
2-{2-[3-[2-(2,3-Dihydro-benzofuran-6-yl)-ethyl]-3-(trans-4-methyl-cyclohexyl)-ureido]-thiazol-5-ylsulfanyl}-2-methyl-propionic acid;
2-{2-[3-[2-(3-Fluoro-phenyl)-ethyl]-3-(trans-4-methyl-cyclohexyl)-ureido]-thiazol-5-ylsulfanyl}-2-methyl-propionic acid;
2-{2-[3-(2-1,3-Benzodioxol-5-yl-ethyl)-3-(trans-4-methyl-cyclohexyl)-ureido]-thiazol-5-ylsulfanyl}-2-methyl-propionic acid;
(2-{3-(trans-4-Methyl-cyclohexyl)-3-[2-(pyridin-3-yl-methoxy)-ethyl]-ureido}-thiazol-5-ylsulfanyl)-acetic acid;
(2-{3-(trans-4-Methyl-cyclohexyl)-3-[2-(pyridin-2-yl-methoxy)-ethyl]-ureido}-thiazol-5-ylsulfanyl)-acetic acid;
(2-{3-(trans-4-Methyl-cyclohexyl)-3-[2-(pyridin-4-yl-methoxy)-ethyl]-ureido}-thiazol-5-ylsulfanyl)-acetic acid;
{2-[3-(2-Cyclopropylmethoxy-ethyl)-3-(trans-4-methyl-cyclohexyl)-ureido]-thiazol-5-ylsulfanyl}-acetic acid;
{2-[3-[2-(5-Chloro-benzo[b]thiophen-3-ylmethoxy)-ethyl]-3-(trans-4-methyl-cyclohexyl)-ureido]-thiazol-5-ylsulfanyl}-acetic acid;
{2-[3-(trans-4-Methyl-cyclohexyl)-3-(5-phenyl-pentyl)-ureido]-thiazol-5-ylsulfanyl}-acetic acid;
2-{2-[3-[3-(3-Methoxy-phenyl)-propyl]-3-(trans-4-methyl-cyclohexyl)-ureido]-thiazol-5-ylsulfanyl}-2-methyl-propionic acid;
2-{2-[3-[3-(3-Chloro-phenyl)-propyl]-3-(trans-4-methyl-cyclohexyl)-ureido]-thiazol-5-ylsulfanyl}-2-methyl-propionic acid;
2-{2-[3-[3-(4-Fluoro-phenyl)-propyl]-3-(trans-4-methyl-cyclohexyl)-ureido]-thiazol-5-ylsulfanyl}-2-methyl-propionic acid;
2-Methyl-2-{2-[3-(trans-4-methyl-cyclohexyl)-3-(4-p-tolyl-butyl)-ureido]-thiazol-5-ylsulfanyl}-propionic acid;
2-{2-[3-[4-(4-Methoxy-phenyl)-butyl]-3-(trans-4-methyl-cyclohexyl)-ureido]-thiazol-5-ylsulfanyl}-2-methyl-propionic acid;
2-{2-[3-[4-(4-Methoxy-phenyl)-butyl]-3-(trans-4-methyl-cyclohexyl)-ureido]-thiazol-5-ylsulfanyl}-2-methyl-propionic acid;
{2-[3-(trans-4-Methoxy-cyclohexyl)-3-(3-phenyl-propyl)-ureido]-thiazol-5-ylsulfanyl}-acetic acid;

{2-[3-(Trans-4-methoxy-cyclohexyl)-3-(4-phenyl-butyl)-ureido]-thiazol-5-ylsulfanyl}-acetic acid;
or a pharmaceutically acceptable salt thereof.

In one embodiment the present invention provides a novel compound wherein the compound is selected from the following:
3-{2-[3-[2-(2-Chloro-benzyloxy)-ethyl]-3-(trans-4-methyl-cyclohexyl)-ureido]-thiazol-5-ylsulfanyl}-2,2-dimethyl-propionic acid;
3-{2-[3-(2-Benzyloxy-ethyl)-3-(trans-4-methyl-cyclohexyl)-ureido]-thiazol-5-ylsulfanyl}-2,2-dimethyl-propionic acid;
2-{2-[3-(2-Benzyloxy-ethyl)-3-(trans-4-methyl-cyclohexyl)-ureido]-thiazol-5-ylsulfanyl}-2-methyl-propionic acid;
2-{2-[3-[3-(2-Methoxy-phenylsulfanyl)-propyl]-3-(trans-4-methyl-cyclohexyl)-ureido]-thiazol-5-ylsulfanyl}-2-methyl-propionic acid;
2-Methyl-2-{2-[3-(trans-4-methyl-cyclohexyl)-3-(4-phenyl-butyl)-ureido]-thiazol-5-ylsulfanyl}-propionic acid;
2-{2-[3-[2-(4-Methoxy-phenyl)-ethyl]-3-(trans-4-methyl-cyclohexyl)-ureido]-thiazol-5-ylsulfanyl}-2-methyl-propionic acid;
3-{2-[3-[2-(4-Methoxy-phenyl)-ethyl]-3-(trans-4-methyl-cyclohexyl)-ureido]-thiazol-5-ylsulfanyl}-2,2-dimethyl-propionic acid;
{2-[3-(trans-4-Methyl-cyclohexyl)-3-(2-phenylsulfanyl-ethyl)-ureido]-thiazol-5-ylsulfanyl}-acetic acid;
2-Methyl-2-{2-[3-(trans-4-methyl-cyclohexyl)-3-(2-phenylsulfanyl-ethyl)-ureido]-thiazol-5-ylsulfanyl}-propionic acid;
{2-[3-(2-Benzylsulfanyl-ethyl)-3-(trans-4-methyl-cyclohexyl)-ureido]-thiazol-5-ylsulfanyl}-acetic acid;
or a pharmaceutically acceptable salt thereof.

In one embodiment the present invention provides a novel compound wherein the compound is selected from the following:
{2-[3-(trans-4-Methyl-cyclohexyl)-3-(3-phenylsulfanyl-propyl)-ureido]-thiazol-5-ylsulfanyl}-acetic acid;
2-Methyl-2-{2-[3-(trans-4-methyl-cyclohexyl)-3-(3-phenylsulfanyl-propyl)-ureido]-thiazol-5-ylsulfanyl}-propionic acid;
2,2-Dimethyl-3-{2-[3-(trans-4-methyl-cyclohexyl)-3-(3-phenylsulfanyl-propyl)-ureido]-thiazol-5-ylsulfanyl}-propionic acid;
2-Methyl-2-{2-[3-(trans-4-methyl-cyclohexyl)-3-(3-phenoxy-propyl)-ureido]-thiazol-5-ylsulfanyl}-propionic acid;
2,2-Dimethyl-3-{2-[3-(trans-4-methyl-cyclohexyl)-3-(3-phenoxy-propyl)-ureido]-thiazol-5-ylsulfanyl}-propionic acid;
{2-[3-(trans-4-Methyl-cyclohexyl)-3-(4-phenyl-butyl)-ureido]-thiazol-5-ylsulfanyl}-acetic acid;
2-{2-[3-(2-Indan-2-yl-ethyl)-3-(trans-4-methyl-cyclohexyl)-ureido]-thiazol-5-ylsulfanyl}-2-methyl-propionic acid;
{2-[3-(2-Indan-2-yl-ethyl)-3-(trans-4-methyl-cyclohexyl)-ureido]-thiazol-5-ylsulfanyl}-acetic acid;
2,2-Dimethyl-3-{2-[3-(3-methyl-butyl)-3-(4-trans-methyl-cyclohexyl)-ureido]-thiazol-5-ylsulfanyl}-propionic acid;
3-{2-[3-(trans-4-Methyl-cyclohexyl)-3-(3-phenylsulfanyl-propyl)-ureido]-thiazol-5-ylsulfanyl}-propionic acid;
or a pharmaceutically acceptable salt thereof.

In one embodiment the present invention provides a novel compound wherein the compound is selected from the following:

2,2-Dimethyl-3-{2-[3-(trans-4-methyl-cyclohexyl)-3-(t-phenyl-butyl)-ureido]-thiazol-5-ylsulfanyl}-propionic acid;
{2-[3-[2-(4-Methoxy-phenyl)-ethyl]-3-(trans-4-methyl-cyclohexyl)-ureido]-thiazole-5-sulfanyl}-acetic acid;
{2-[3-(2-Benzyloxy-ethyl)-3-(trans-4-methyl-cyclohexyl)-ureido]-thiazole-5-sulfanyl}-acetic acid;
2-{2-[3-[2-(4-Fluoro-2-trifluoromethyl-benzyloxy)-ethyl]-3-(trans-4-methyl-cyclohexyl)-ureido]-thiazol-5-ylsulfanyl}-2-methyl-propionic acid;
2-{2-[3-[2-(2-Chloro-4-fluoro-benzyloxy)-ethyl]-3-(trans-4-methyl-cyclohexyl)-ureido]-thiazol-5-ylsulfanyl}-2-methyl-propionic acid;
2-Methyl-2-(2-{3-(trans-4-methyl-cyclohexyl)-3-[2-(2-trifluoromethyl-benzyloxy)-ethyl]-ureido}-thiazol-5-ylsulfanyl)-propionic acid;
2-{2-[3-[2-(2,4-Difluoro-benzyloxy)-ethyl]-3-(trans-4-methyl-cyclohexyl)-ureido]-thiazol-5-ylsulfanyl}-2-methyl-propionic acid;
2-Methyl-2-{2-[3-[2-(2-methyl-benzyloxy)-ethyl]-3-(trans-4-methyl-cyclohexyl)-ureido]-thiazol-5-ylsulfanyl}-propionic acid;
3-{2-[3-[2-(4-Fluoro-2-trifluoromethyl-benzyloxy)-ethyl]-3-(trans-4-methyl-cyclohexyl)-ureido]-thiazol-5-ylsulfanyl}-2,2-dimethyl-propionic acid;
3-{2-[3-[2-(2-Chloro-4-fluoro-benzyloxy)-ethyl]-3-(trans-4-methyl-cyclohexyl)-ureido]-thiazol-5-ylsulfanyl}-2,2-dimethyl-propionic acid;
or a pharmaceutically acceptable salt thereof.

In one embodiment the present invention provides a novel compound wherein the compound is selected from the following:
2-Methyl-2-{2-[3-(trans-4-methyl-cyclohexyl)-3-phenethyl-ureido]-thiazol-5-ylsulfanyl}-propionic acid;
2,2-Dimethyl-3-{2-[3-(trans-4-methyl-cyclohexyl)-3-phenethyl-ureido]-thiazol-5-ylsulfanyl}-propionic acid;
3-{2-[3-[2-(2-Fluoro-benzyloxy)-ethyl]-3-(trans-4-methyl-cyclohexyl)-ureido]-thiazol-5-ylsulfanyl}-2,2-dimethyl-propionic acid;
3-{2-[3-[2-(2,4-Difluoro-benzyloxy)-ethyl]-3-(trans-4-methyl-cyclohexyl)-ureido]-thiazol-5-ylsulfanyl}-2,2-dimethyl-propionic acid;
2,2-Dimethyl-3-{2-[3-[2-(2-methyl-benzyloxy)-ethyl]-3-(trans-4-methyl-cyclohexyl)-ureido]-thiazol-5-ylsulfanyl}-propionic acid;
2-Methyl-2-(2-{3-(trans-4-methyl-cyclohexyl)-3-[2-(4-trifluoromethoxy-phenyl)-ethyl]-ureido}-thiazol-5-ylsulfanyl)-propionic acid;
2-{2-[3-[2-(4-Chloro-phenyl)-ethyl]-3-(trans-4-methyl-cyclohexyl)-ureido]-thiazol-5-ylsulfanyl}-2-methyl-propionic acid;
2-Methyl-2-{2-[3-(trans-4-methyl-cyclohexyl)-3-(3-phenyl-propyl)-ureido]-thiazol-5-ylsulfanyl}-propionic acid;
2,2-Dimethyl-3-(2-{3-(trans-4-methyl-cyclohexyl)-3-[2-(2-trifluoromethyl-benzyloxy)-ethyl]-ureido}-thiazol-5-ylsulfanyl)-propionic acid;
2-{2-[3-[2-(2-Difluoromethoxy-benzyloxy)-ethyl]-3-(trans-4-methyl-cyclohexyl)-ureido]-thiazol-5-ylsulfanyl}-2-methyl-propionic acid;
or a pharmaceutically acceptable salt thereof.

In one embodiment the present invention provides a novel compound wherein the compound is selected from the following:
2-{2-[3-[2-(3-Fluoro-4-methoxy-phenyl)-ethyl]-3-(trans-4-methyl-cyclohexyl)-ureido]-thiazol-5-ylsulfanyl}-2-methyl-propionic acid;
2-{2-[3-[2-(3-Chloro-5-fluoro-phenyl)-ethyl]-3-(trans-4-methyl-cyclohexyl)-ureido]-thiazol-5-ylsulfanyl}-2-methyl-propionic acid;
2-Methyl-2-(2-{3-(trans-4-methyl-cyclohexyl)-3-[3-(3-trifluoromethyl-phenylsulfanyl)-propyl]-ureido}-thiazol-5-ylsulfanyl)-propionic acid;
2-{2-[3-[3-(2-Chloro-phenylsulfanyl)-propyl]-3-(trans-4-methyl-cyclohexyl)-ureido]-thiazol-5-ylsulfanyl}-2-methyl-propionic acid;
2-{2-[3-[2-(3,5-Difluoro-phenyl)-ethyl]-3-(trans-4-methyl-cyclohexyl)-ureido]-thiazol-5-ylsulfanyl}-2-methyl-propionic acid;
2-Methyl-2-{2-[3-(trans-4-methyl-cyclohexyl)-3-(2-p-tolyl-ethyl)-ureido]-thiazol-5-ylsulfanyl}-propionic acid;
2-{2-[3-[3-(4-Chloro-phenylsulfanyl)-propyl]-3-(trans-4-methyl-cyclohexyl)-ureido]-thiazol-5-ylsulfanyl}-2-methyl-propionic acid;
2-{2-[3-[3-(3-Chloro-phenylsulfanyl)-propyl]-3-(trans-4-methyl-cyclohexyl)-ureido]-thiazol-5-ylsulfanyl}-2-methyl-propionic acid;
2-{2-[3-[3-(4-Methoxy-phenylsulfanyl)-propyl]-3-(trans-4-methyl-cyclohexyl)-ureido]-thiazol-5-ylsulfanyl}-2-methyl-propionic acid;
2-{2-[3-[3-(3-Methoxy-phenylsulfanyl)-propyl]-3-(trans-4-methyl-cyclohexyl)-ureido]-thiazol-5-ylsulfanyl}-2-methyl-propionic acid;
or a pharmaceutically acceptable salt thereof.

In one embodiment the present invention provides a novel compound wherein the compound is selected from the following:
2-{2-[3-[3-(2-Fluoro-phenylsulfanyl)-propyl]-3-(trans-4-methyl-cyclohexyl)-ureido]-thiazol-5-ylsulfanyl}-2-methyl-propionic acid;
2-{2-[3-[3-(4-Fluoro-phenylsulfanyl)-propyl]-3-(trans-4-methyl-cyclohexyl)-ureido]-thiazol-5-ylsulfanyl}-2-methyl-propionic acid;
2-Methyl-2-(2-{3-(trans-4-methyl-cyclohexyl)-3-[3-(2-trifluoromethoxy-phenylsulfanyl)-propyl]-ureido}-thiazol-5-ylsulfanyl)-propionic acid;
2-Methyl-2-(2-{3-(trans-4-methyl-cyclohexyl)-3-[3-(4-trifluoromethoxy-phenylsulfanyl)-propyl]-ureido}-thiazol-5-ylsulfanyl)-propionic acid;
2-{2-[3-[3-(3-Fluoro-phenylsulfanyl)-propyl]-3-(trans-4-methyl-cyclohexyl)-ureido]-thiazol-5-ylsulfanyl}-2-methyl-propionic acid;
{2-[3-(trans-4-Methyl-cyclohexyl)-3-(3-oxo-3-phenyl-propyl)-ureido]-thiazol-5-ylsulfanyl}-acetic acid;
{2-[-3-[3-(4-Methoxy-phenyl)-propyl]-3-(4-methyl-cyclohexyl)-ureido]-thiazol-5-ylsulfanyl}-acetic acid;
{2-[-3-[3-(3-Methoxy-phenyl)-propyl]-3-(4-methyl-cyclohexyl)-ureido]-thiazol-5-ylsulfanyl}-acetic acid;
{2-[3-Benzyl-3-(trans-4-methyl-cyclohexyl)-ureido]-thiazol-5-ylsulfanyl}-acetic acid;
(2-{3-(trans-4-Methyl-cyclohexyl)-3-[2-(toluene-4-sulfonyl)-ethyl]-ureido}-thiazol-5-ylsulfanyl)-acetic acid;
or a pharmaceutically acceptable salt thereof.

In one embodiment the present invention provides a novel compound wherein the compound is selected from the following:
{2-[-3-(3-Cyclohexyl-propyl)-3-(trans-4-methyl-cyclohexyl)-ureido]-thiazol-5-ylsulfanyl}-acetic acid;
(2-{-3-(trans-4-Methyl-cyclohexyl)-3-[3-(3-trifluoromethyl-phenyl)-propyl]-ureido}-thiazol-5-ylsulfanyl)-acetic acid;
{2-[-3-[3-(4-Chloro-phenyl)-propyl]-3-(trans-4-methyl-cyclohexyl)-ureido]-thiazol-5-ylsulfanyl}-acetic acid;

{2-[-3-[3-(3-Chloro-phenyl)-propyl]-3-(trans-4-methyl-cyclohexyl)-ureido]-thiazol-5-ylsulfanyl}-acetic acid;
{2-[3-[4-(4-Methoxy-phenyl)-butyl]-3-(4-methyl-cyclohexyl)-ureido]-thiazol-5-ylsulfanyl}-acetic acid;
{2-[3-(4-Methyl-cyclohexyl)-3-(4-p-tolyl-butyl)-ureido]-thiazol-5-ylsulfanyl}-acetic acid;
{2[-3-[3-(4-Fluoro-phenyl)-propyl]-3-(trans-4-methyl-cyclohexyl)-ureido]-thiazol-5-ylsulfanyl}-acetic acid;
{2-[3-[3-(5-Chloro-benzofuran-3-yl)-propyl]-3-(trans-4-methyl-cyclohexyl)-ureido]-thiazol-5-ylsulfanyl}-acetic acid;
{2-[3-[4-(4-Chloro-phenyl)-butyl]-3-(trans-4-methyl-cyclohexyl)-ureido]-thiazol-5-ylsulfanyl}-acetic acid;
{2-[3-(trans-4-Methyl-cyclohexyl)-3-(3-pyridin-3-yl-propyl)-ureido]-thiazol-5-ylsulfanyl}-acetic acid;
or a pharmaceutically acceptable salt thereof.

In one embodiment the present invention provides a novel compound wherein the compound is selected from the following:
{2[-3-(trans-4-Methyl-cyclohexyl)-3-(trans-2-phenyl-cyclopropylmethyl)-ureido]-thiazol-5-ylsulfanyl}-acetic acid;
{2-[3-(2-Methanesulfonyl-ethyl)-3-(trans-4-methyl-cyclohexyl)-ureido]-thiazol-5-ylsulfanyl}-acetic acid;
{2-[3-Benzo[1,3]dioxol-5-ylmethyl-3-(trans-4-methyl-cyclohexyl)-ureido]-thiazol-5-ylsulfanyl}-acetic acid;
{2-[3-[4-(1H-Indol-3-yl)-butyl]-3-(trans-4-methyl-cyclohexyl)-ureido]-thiazol-5-ylsulfanyl}-acetic acid;
{2-[3-(4-Cyclohexyl-butyl)-3-(trans-4-methyl-cyclohexyl)-ureido]-thiazol-5-ylsulfanyl}-acetic acid;
{2-[3-[4-(4-Fluoro-phenyl)-4-hydroxy-butyl]-3-(trans-4-methyl-cyclohexyl)-ureido]-thiazol-5-ylsulfanyl}-acetic acid;
{2-[3-[4-(3-Fluoro-4-methoxy-phenyl)-4-hydroxy-butyl]-3-(trans-4-methyl-cyclohexyl)-ureido]-thiazol-5-ylsulfanyl}-acetic acid;
{2-[3-(trans-4-Methyl-cyclohexyl)-3-(1,2,3,4-tetrahydro-naphthalen-2-ylmethyl)-ureido]-thiazol-5-ylsulfanyl}-acetic acid;
2-{2-[3-[2-(4-Acetyl-phenyl)-ethyl]-3-(trans-4-methyl-cyclohexyl)-ureido]-thiazol-5-ylsulfanyl}-2-methyl-propionic acid;
{2-[3-[3-(1H-Indol-3-yl)-propyl]-3-(trans-4-methyl-cyclohexyl)-ureido]-thiazol-5-ylsulfanyl}-acetic acid;
or a pharmaceutically acceptable salt thereof.

In one embodiment the present invention provides a novel compound wherein the compound is selected from the following:
{2-[3-[4-(3,4-Dimethoxy-phenyl)-butyl]-3-(trans-4-methyl-cyclohexyl)-ureido]-thiazol-5-ylsulfanyl}-acetic acid;
{2-[3-(trans-4-Methyl-cyclohexyl)-3-(2-methyl-2-phenyl-propyl)-ureido]-thiazol-5-ylsulfanyl}-acetic acid;
{2-[3-(2,2-Difluoro-2-phenyl-ethyl)-3-(trans-4-methyl-cyclohexyl)-ureido]-thiazol-5-ylsulfanyl}-acetic acid;
{2-[3-(But-3-ynyl)-3-(trans-4-methyl-cyclohexyl)-ureido]-thiazol-5-ylsulfanyl}-acetic acid;
{2-[3-(Trans-4-methoxy-cyclohexyl)-3-phenethyl-ureido]-thiazol-5-ylsulfanyl}-acetic acid;
{2-[3-(2-Benzyloxy-ethyl)-3-(trans-4-methoxy-cyclohexyl)-ureido]-thiazol-5-ylsulfanyl}-acetic acid;
2-{2-[3-[2-(3-Chloro-phenyl)-ethyl]-3-(trans-4-methyl-cyclohexyl)-ureido]-thiazol-5-ylsulfanyl}-2-methyl-propionic acid;
2-{2-[3-[2-(3-Chloro-phenyl)-ethyl]-3-(trans-4-methyl-cyclohexyl)-ureido]-thiazol-5-ylsulfanyl}-2-methyl-propionic acid;
2-{2-[3-[2-(3-Methoxy-phenyl)-ethyl]-3-(trans-4-methyl-cyclohexyl)-ureido]-thiazol-5-ylsulfanyl}-2-methyl-propionic acid;
2-{2-[3-[2-(3,4-Dimethoxy-phenyl)-ethyl]-3-(trans-4-methyl-cyclohexyl)-ureido]-thiazol-5-ylsulfanyl}-2-methyl-propionic acid;
or a pharmaceutically acceptable salt thereof.

In one embodiment the present invention provides a novel compound wherein the compound is selected from the following:
{2-[3-(2-Cyano-ethyl)-3-(trans-4-methyl-cyclohexyl)-ureido]-thiazol-5-ylsulfanyl}-acetic acid;
{2-[3-(trans-4-Methyl-cyclohexyl)-3-pyridin-4-ylmethyl-ureido]-thiazol-5-ylsulfanyl}-acetic acid;
{2-[3-(trans-4-Methyl-cyclohexyl)-3-pyridin-2-ylmethyl-ureido]-thiazol-5-ylsulfanyl}-acetic acid;
{2-[3-(trans-4-Methyl-cyclohexyl)-3-pyridin-3-ylmethyl-ureido]-thiazol-5-ylsulfanyl}-acetic acid;
{2-[3-[4-(4-Methanesulfonyl-phenyl)-but-3-ynyl]-3-(trans-4-methyl-cyclohexyl)-ureido]-thiazol-5-ylsulfanyl}-acetic acid;
{2-[3-(trans-4-Methyl-cyclohexyl)-3-(4-phenyl-but-3-ynyl)-ureido]-thiazol-5-ylsulfanyl}-acetic acid;
1-{2-[3-[2-(2-Chloro-benzyloxy)-ethyl]-3-(trans-4-methyl-cyclohexyl)-ureido]-thiazol-5-ylsulfanyl}-cyclobutanecarboxylic acid;
1-{2-[3-[2-(2-Chloro-benzyloxy)-ethyl]-3-(trans-4-methyl-cyclohexyl)-ureido]-thiazol-5-ylsulfanyl}-cyclohexanecarboxylic acid;
1-{2-[3-(trans-4-Methyl-cyclohexyl)-3-(4-phenyl-butyl)-ureido]-thiazol-5-ylsulfanyl}-cyclobutanecarboxylic acid;
1-{2-[3-(trans-4-Methyl-cyclohexyl)-3-(4-phenyl-butyl)-ureido]-thiazol-5-ylsulfanyl}-cyclohexanecarboxylic acid;
or a pharmaceutically acceptable salt thereof.

In one embodiment the present invention provides a novel compound wherein the compound is selected from the following:
1-{2-[3-[2-(trans-4-Methoxy-phenyl)-ethyl]-3-(4-methyl-cyclohexyl)-ureido]-thiazol-5-ylsulfanyl}-cyclobutanecarboxylic acid;
1-{2-[3-[2-(4-Methoxy-phenyl)-ethyl]-3-(trans-4-methyl-cyclohexyl)-ureido]-thiazol-5-ylsulfanyl}-cyclohexanecarboxylic acid;
2-{2-[3-[2-(4-Fluoro-phenyl)-ethyl]-3-(trans-4-methyl-cyclohexyl)-ureido]-thiazol-5-ylsulfanyl}-2-methyl-propionic acid;
2-{2-[3-[2-(2,3-Dihydro-benzofuran-6-yl)-ethyl]-3-(trans-4-methyl-cyclohexyl)-ureido]-thiazol-5-ylsulfanyl}-2-methyl-propionic acid;
2-{2-[3-[2-(3-Fluoro-phenyl)-ethyl]-3-(trans-4-methyl-cyclohexyl)-ureido]-thiazol-5-ylsulfanyl}-2-methyl-propionic acid;
2-{2-[3-(2-1,3-Benzodioxol-5-yl-ethyl)-3-(trans-4-methyl-cyclohexyl)-ureido]-thiazol-5-ylsulfanyl}-2-methyl-propionic acid;
(2-{3-(trans-4-Methyl-cyclohexyl)-3-[2-(pyridin-3-ylmethoxy)-ethyl]-ureido}-thiazol-5-ylsulfanyl)-acetic acid;
(2-{3-(trans-4-Methyl-cyclohexyl)-3-[2-(pyridin-2-ylmethoxy)-ethyl]-ureido}-thiazol-5-ylsulfanyl)-acetic acid;
(2-{3-(trans-4-Methyl-cyclohexyl)-3-[2-(pyridin-4-ylmethoxy)-ethyl]-ureido}-thiazol-5-ylsulfanyl)-acetic acid;

{2-[3-(2-Cyclopropylmethoxy-ethyl)-3-(trans-4-methyl-cyclohexyl)-ureido]-thiazol-5-ylsulfanyl}-acetic acid;
or a pharmaceutically acceptable salt thereof.

In one embodiment the present invention provides a novel compound wherein the compound is selected from the following:
{2-[3-[2-(5-Chloro-benzo[b]thiophen-3-ylmethoxy)-ethyl]-3-(trans-4-methyl-cyclohexyl)-ureido]-thiazol-5-ylsulfanyl}-acetic acid;
{2-[3-(trans-4-Methyl-cyclohexyl)-3-(5-phenyl-pentyl)-ureido]-thiazol-5-ylsulfanyl}-acetic acid;
2-{2-[3-[3-(3-Methoxy-phenyl)-propyl]-3-(trans-4-methyl-cyclohexyl)-ureido]-thiazol-5-ylsulfanyl}-2-methyl-propionic acid;
2-{2-[3-[3-(3-Chloro-phenyl)-propyl]-3-(trans-4-methyl-cyclohexyl)-ureido]-thiazol-5-ylsulfanyl}-2-methyl-propionic acid;
2-{2-[3-[3-(4-Fluoro-phenyl)-propyl]-3-(trans-4-methyl-cyclohexyl)-ureido]-thiazol-5-ylsulfanyl}-2-methyl-propionic acid;
2-Methyl-2-{2-[3-(trans-4-methyl-cyclohexyl)-3-(4-p-tolyl-butyl)-ureido]-thiazol-5-ylsulfanyl}-propionic acid;
2-{2-[3-[4-(4-Methoxy-phenyl)-butyl]-3-(trans-4-methyl-cyclohexyl)-ureido]-thiazol-5-ylsulfanyl}-2-methyl-propionic acid;
2-{2-[3-[4-(4-Methoxy-phenyl)-butyl]-3-(trans-4-methyl-cyclohexyl)-ureido]-thiazol-5-ylsulfanyl}-2-methyl-propionic acid;
{2-[3-(trans-4-Methoxy-cyclohexyl)-3-(3-phenyl-propyl)-ureido]-thiazol-5-ylsulfanyl}-acetic acid;
{2-[3-(Trans-4-methoxy-cyclohexyl)-3-(4-phenyl-butyl)-ureido]-thiazol-5-ylsulfanyl}-acetic acid;
or a pharmaceutically acceptable salt thereof.

In one embodiment the present invention provides a novel compound wherein the compound is selected from the following:
2-{2-[3-[4-(4-Chloro-phenyl)-butyl]-3-(trans-4-methyl-cyclohexyl)-ureido]-thiazol-5-ylsulfanyl}-2-methyl-propionic acid;
2-Methyl-2-{2-[3-(trans-4-methyl-cyclohexyl)-3-(3-pyridin-3-yl-propyl)-ureido]-thiazol-5-ylsulfanyl}-propionic acid;
2-{2-[3-[3-(1H-Indol-3-yl)-propyl]-3-(trans-4-methyl-cyclohexyl)-ureido]-thiazol-5-ylsulfanyl}-2-methyl-propion ic acid;
2-{2-[3-[4-(3,4-Dimethoxy-phenyl)-butyl]-3-(trans-4-methyl-cyclohexyl)-ureido]-thiazol-5-ylsulfanyl}-2-methyl-propionic acid;
2-Methyl-2-(2-{3-(4-methyl-cyclohexyl)-3-[2-(trans-4-methylsulfanyl-phenyl)-ethyl]-ureido}-thiazol-5-ylsulfanyl)-propionic acid;
2-{2-[3-[2-(4-Isopropyl-phenyl)-ethyl]-3-(trans-4-methyl-cyclohexyl)-ureido]-thiazol-5-ylsulfanyl}-2-methyl-propionic acid;
2-Methyl-2-(2-{3-(trans-4-methyl-cyclohexyl)-3-[2-(3,4,5-trifluoro-phenyl)-ethyl]-ureido}-thiazol-5-ylsulfanyl)-propionic acid;
2-Methyl-2-(2-{3-(trans-4-methyl-cyclohexyl)-3-[2-(2,3,4-trifluoro-phenyl)-ethyl]-ureido}-thiazol-5-ylsulfanyl)-propionic acid;
2-{2-[3-[2-(2-Fluoro-4-methoxy-phenyl)-ethyl]-3-(trans-4-methyl-cyclohexyl)-ureido]-thiazol-5-ylsulfanyl}-2-methyl-propionic acid;
2-{2-[3-[2-(3-Fluoro-4-trifluoromethoxy-phenyl)-ethyl]-3-(trans-4-methyl-cyclohexyl)-ureido]-thiazol-5-ylsulfanyl}-2-methyl-propionic acid;
2-{2-[3-[2-(3,5-Difluoro-4-methoxy-phenyl)-ethyl]-3-(trans-4-methyl-cyclohexyl)-ureido]-thiazol-5-ylsulfanyl}-2-methyl-propionic acid;
2-{2-[3-[2-(4-Methoxy-3-methyl-phenyl)-ethyl]-3-(trans-4-methyl-cyclohexyl)-ureido]-thiazol-5-ylsulfanyl}-2-methyl-propionic acid;
2-{2-[3-[2-(2,3-Difluoro-4-methoxy-phenyl)-ethyl]-3-(trans-4-methyl-cyclohexyl)-ureido]-thiazol-5-ylsulfanyl}-2-methyl-propionic acid;
or a pharmaceutically acceptable salt thereof.

In one embodiment the present invention provides a novel compound wherein the compound is selected from the following:
2-{2-[3-(2-Benzyloxy-ethyl)-3-(trans-4-methyl-cyclohexyl)-ureido]-thiazol-5-ylsulfanyl}-2-methyl-propionic acid
or a pharmaceutically acceptable salt thereof.

In one embodiment the present invention provides a novel compound wherein the compound is selected from the following:
2-Methyl-2-{2-[3-(trans-4-methyl-cyclohexyl)-3-(4-phenyl-butyl)-ureido]-thiazol-5-ylsulfanyl}-propionic acid
or a pharmaceutically acceptable salt thereof.

In one embodiment the present invention provides a novel compound wherein the compound is selected from the following:
2-{2-[3-[2-(4-Methoxy-phenyl)-ethyl]-3-(trans-4-methyl-cyclohexyl)-ureido]-thiazol-5-ylsulfanyl}-2-methyl-propionic acid
or a pharmaceutically acceptable salt thereof.

In one embodiment the present invention provides a novel compound wherein the compound is selected from the following:
{2-[3-(trans-4-Methyl-cyclohexyl)-3-(2-phenylsulfanyl-ethyl)-ureido]-thiazol-5-ylsulfanyl}-acetic acid
or a pharmaceutically acceptable salt thereof.

In one embodiment the present invention provides a novel compound wherein the compound is selected from the following:
or a pharmaceutically acceptable salt thereof.

In one embodiment the present invention provides a novel compound wherein the compound is selected from the following:
2,2-Dimethyl-3-{2-[3-(trans-4-methyl-cyclohexyl)-3-(3-phenoxy-propyl)-ureido]-thiazol-5-ylsulfanyl}-propionic acid
or a pharmaceutically acceptable salt thereof.

In one embodiment the present invention provides a novel compound wherein the compound is selected from the following:
2-{2-[3-(2-Indan-2-yl-ethyl)-3-(trans-4-methyl-cyclohexyl)-ureido]-thiazol-5-ylsulfanyl}-2-methyl-propionic acid
or a pharmaceutically acceptable salt thereof.

In one embodiment the present invention provides a novel compound wherein the compound is selected from the following:
2-Methyl-2-{2-[3-(trans-4-methyl-cyclohexyl)-3-phenethyl-ureido]-thiazol-5-ylsulfanyl}-propionic acid
or a pharmaceutically acceptable salt thereof.

In one embodiment the present invention provides a novel compound wherein the compound is selected from the following:
2-{2-[3-[2-(3-Fluoro-4-methoxy-phenyl)-ethyl]-3-(trans-4-methyl-cyclohexyl)-ureido]-thiazol-5-ylsulfanyl}-2-methyl-propionic acid
or a pharmaceutically acceptable salt thereof.

In one embodiment the present invention provides a novel compound wherein the compound is selected from the following:

{2-[3-(trans-4-Methyl-cyclohexyl)-3-(1,2,3,4-tetrahydro-naphthalen-2-ylmethyl)-ureido]-thiazol-5-ylsulfanyl}-acetic acid or a pharmaceutically acceptable salt thereof.

In one embodiment the present invention provides a novel compound wherein the compound is selected from the following:

{2-[3-(trans-4-Methyl-cyclohexyl)-3-(2-methyl-2-phenyl-propyl)-ureido]-thiazol-5-ylsulfanyl}-acetic acid or a pharmaceutically acceptable salt thereof.

In one embodiment the present invention provides a novel compound wherein the compound is selected from the following:

{2-[3-(2,2-Difluoro-2-phenyl-ethyl)-3-(trans-4-methyl-cyclohexyl)-ureido]-thiazol-5-ylsulfanyl}-acetic acid or a pharmaceutically acceptable salt thereof.

In one embodiment the present invention provides a novel compound wherein the compound is selected from the following:

2-{2-[3-[2-(3,4-Dimethoxy-phenyl)-ethyl]-3-(trans-4-methyl-cyclohexyl)-ureido]-thiazol-5-ylsulfanyl}-2-methyl-propionic acid or a pharmaceutically acceptable salt thereof.

In one embodiment the present invention provides a novel compound wherein the compound is selected from the following:

2-{2-[3-[2-(2,3-Dihydro-benzofuran-6-yl)-ethyl]-3-(trans-4-methyl-cyclohexyl)-ureido]-thiazol-5-ylsulfanyl}-2-methyl-propionic acid or a pharmaceutically acceptable salt thereof.

In another embodiment, the present invention provides a novel pharmaceutical composition, comprising: a pharmaceutically acceptable carrier and a compound of the present invention, or a pharmaceutically acceptable salt thereof.

In another embodiment, the present invention provides a novel method of treating type 2 diabetes, comprising: administering to a subject in need thereof a therapeutically effective amount of a compound of the present invention.

In one embodiment the invention provides a method of preventing hypoglycaemia comprising administration of a compound according to the present invention.

In another embodiment the invention provides the use of a compound according to the present invention for the preparation of a medicament for the prevention of hypoglycaemia.

In another embodiment the invention provides a compound as described herein, which is an agent useful for the treatment of an indication selected from the group consisting of hyperglycemia, IGT, insulin resistance syndrome, syndrome X, type 2 diabetes, type 1 diabetes, dyslipidemia, hypertension, and obesity.

In another embodiment the invention provides a compound as described herein for use as a medicament.

In another embodiment the invention provides a compound as described herein for treatment of hyperglycemia, for treatment of IGT, for treatment of Syndrome X, for treatment of type 2 diabetes, for treatment of type 1 diabetes, for treatment of dyslipidemia, for treatment of hyperlipidemia, for treatment of hypertension, for treatment of obesity, for lowering of food in-take, for appetite regulation, for regulating feeding behaviour, or for enhancing the secretion of enteroincretins, such as GLP-1.

In another embodiment the invention provides a pharmaceutical composition comprising, as an active ingredient, at least one compound as described herein together with one or more pharmaceutically acceptable carriers or excipients.

In one embodiment such a pharmaceutical composition may be in unit dosage form, comprising from about 0.05 mg to about 1000 mg, preferably from about 0.1 mg to about 500 mg and especially preferred from about 0.5 mg to about 200 mg of the compound according to the present invention.

In another embodiment the invention provides the use of a compound according to the invention for increasing the activity of glucokinase.

In another embodiment the invention provides the use of a compound according to the invention for the preparation of a medicament for the treatment of metabolic disorders, for blood glucose lowering, for the treatment of hyperglycemia, for the treatment of IGT, for the treatment of Syndrome X, for the treatment of impaired fasting glucose (IFG), for the treatment of type 2 diabetes, for the treatment of type 1 diabetes, for delaying the progression of impaired glucose tolerance (IGT) to type 2 diabetes, for delaying the progression of non-insulin requiring type 2 diabetes to insulin requiring type 2 diabetes, for the treatment of dyslipidemia, for the treatment of hyperlipidemia, for the treatment of hypertension, for lowering of food intake, for appetite regulation, for the treatment of obesity, for regulating feeding behavior, or for enhancing the secretion of enteroincretins. In another embodiment the invention provides the use of a compound according to the invention for the preparation of a medicament for the adjuvant treatment of type 1 diabetes for preventing the onset of diabetic complications.

In another embodiment the invention provides the use of a compound according to the invention for the preparation of a medicament for increasing the number and/or the size of beta cells in a mammalian subject, for treatment of beta cell degeneration, in particular apoptosis of beta cells, or for treatment of functional dyspepsia, in particular irritable bowel syndrome.

In one embodiment the invention provides any of the above uses in a regimen which comprises treatment with a further antidiabetic agent.

In a further embodiment the invention provides the use of a compound according to the invention or a pharmaceutical composition as described above for the treatment of metabolic disorders, for blood glucose lowering, for the treatment of hyperglycemia, for treatment of IGT, for treatment of Syndrome X, for the treatment of impaired fasting glucose (IFG), for treatment of type 2 diabetes, for treatment of type 1 diabetes, for delaying the progression of impaired glucose tolerance (IGT) to type 2 diabetes, for delaying the progression of non-insulin requiring type 2 diabetes to insulin requiring type 2 diabetes, for treatment of dyslipidemia, for treatment of hyperlipidemia, for treatment of hypertension, for the treatment or prophylaxis of obesity, for lowering of food intake, for appetite regulation, for regulating feeding behavior, or for enhancing the secretion of enteroincretins.

In a further embodiment the invention provides the use of a compound according to the invention or a pharmaceutical composition as described above for the adjuvant treatment of type 1 diabetes for preventing the onset of diabetic complications.

In a further embodiment the invention provides the use of a compound according to the invention or a pharmaceutical composition as described above for increasing the number and/or the size of beta cells in a mammalian subject, for treatment of beta cell degeneration, in particular apoptosis of beta cells, or for treatment of functional dyspepsia, in particular irritable bowel syndrome.

In another embodiment the invention provides a method for the treatment of a glucokinase-deficiency mediated condition/disease which is caused by a glucokinase mutation.

In another embodiment the invention provides a method wherein the glucokinase-deficiency mediated condition/disease is Maturity-Onset Diabetes of the Young, Neonatal Diabetes Mellitus, or Persistent Neonatal Diabetes Mellitus.

In another embodiment the invention provides a method for preventing or ameliorating the development of diabetes in subjects exhibiting symptoms of Impaired Glucose Tolerance, Gestational Diabetes Mellitus, Polycystic Ovarian Syndrome, Cushings syndrome or Metabolic Syndrome comprising administering to a subject in need of such treatment a compound according to the invention or pharmaceutical composition thereof, wherein blood glucose normalization occurs with reduced risk of hypoglycemia.

In another embodiment the invention provides a method for preventing or ameliorating microvascular diseases comprising administering to a subject in need of such treatment a compound according to the invention or pharmaceutical composition thereof.

In another embodiment the invention provides a method for preventing macrovascular diseases in subjects exhibiting symptoms of Impaired Glucose Tolerance, Gestational Diabetes Mellitus, or Metabolic Syndrome, comprising administering to a subject in need of such treatment a compound according to the invention or pharmaceutical composition thereof, alone or in combination with lipid-lowering drugs, wherein blood glucose normalization occurs with reduced risk of hypoglycemia.

In another embodiment the invention provides a method for the preservation of beta-cell mass and function comprising administering to a subject in need of such treatment a compound according to the invention or pharmaceutical composition thereof, wherein blood glucose normalization occurs with reduced risk of hypoglycemia.

In another embodiment the invention provides a method for preventing amyloid beta peptide induced cell death comprising administering to a subject in need of such treatment a compound according to the invention or pharmaceutical composition thereof, wherein blood glucose normalization occurs with reduced risk of hypoglycemia.

In another embodiment the invention provides a method wherein the subject is a veterinary subject.

In another embodiment the invention provides a method wherein a compound according to the invention is administered as a food additive.

In another embodiment the invention provides a method for the treatment of hepatic conditions benefiting from blood glucose normalization comprising administering to a subject in need of such treatment a compound according to the invention or pharmaceutical composition thereof, wherein blood glucose normalization occurs with reduced risk of hypoglycemia.

In another embodiment the invention provides a method for the treatment of hepatic conditions benefiting from improved liver function comprising administering to a subject in need of such treatment a compound according to the invention or pharmaceutical composition thereof.

In another embodiment the invention provides a method for the treatment of hyperglycemic conditions that result from critical illness, or as a consequence of therapeutic intervention comprising administering to a subject in need of such treatment a compound according to the invention or pharmaceutical composition thereof, wherein blood glucose normalization occurs with reduced risk of hypoglycemia.

In another embodiment the invention provides a method for the treatment of hepatic conditions that result from critical illness like cancer, or are a consequence of therapy, for example cancer therapy or HIV-treatment, comprising administering to a subject in need of such treatment a compound according to the invention or pharmaceutical composition thereof.

In another embodiment the invention provides a method of treatment adjuvant to insulin in insulin-requiring diabetes type 2, or as replacement for insulin comprising administering to a subject in need of such treatment a compound according to the invention or pharmaceutical composition thereof, wherein blood glucose normalization occurs with reduced risk of hypoglycemia.

In another embodiment the invention provides a method for the treatment of lipodistrophy comprising administering to a subject in need of such treatment a compound according to the invention or pharmaceutical composition thereof, wherein blood glucose normalization occurs with reduced risk of hypoglycemia.

In another embodiment the invention provides a method for the treatment of hyperglycemia resulting from severe physical stress without signs of liver failure comprising administering to a subject in need of such treatment a compound according to the invention or pharmaceutical composition thereof, wherein blood glucose normalization occurs with reduced risk of hypoglycemia.

In another embodiment the invention provides a method wherein the severe physical stress is multiple trauma, or diabetic ketoacidosis.

In another embodiment the invention provides a method for preventing apoptotic liver damage comprising administering to a subject in need of such treatment a compound according to the invention or pharmaceutical composition thereof.

In another embodiment the invention provides a method for preventing hypoglycemia comprising administering to a subject in need of such treatment a compound according to the invention or pharmaceutical composition thereof, wherein blood glucose normalization occurs with reduced risk of hypoglycemia.

In another embodiment the invention provides a method for increasing beta-cell mass and function comprising administering to a subject in need of such treatment a compound according to the invention or pharmaceutical composition thereof, wherein blood glucose normalization occurs with reduced risk of hypoglycemia.

In another embodiment the invention provides a method of preventing type 1 diabetes comprising administering to a subject in need of such treatment a compound according to the invention or pharmaceutical composition thereof, wherein blood glucose normalization occurs with reduced risk of hypoglycemia.

In another embodiment the invention provides a method of preserving and/or increasing beta-cell mass and function in patients having undergone pancreatic islet transplantation comprising administering to a subject in need of such treatment a compound according to the invention or pharmaceutical composition thereof.

In another embodiment the invention provides a method of improving glucose control during and after surgery comprising administering to a subject in need of such treatment a compound according to the invention or pharmaceutical composition thereof.

In another embodiment the invention provides a method of improving liver function and/or survival in patients undergoing liver transplantation comprising administering to a subject in need of such treatment a compound according to the invention or pharmaceutical composition thereof. In another embodiment hereof the invention provides a method wherein the administration occurs before, during or after transplantation, or any combination thereof.

In another embodiment the invention provides a method of obtaining blood glucose normalization comprising administering to a subject in need of such treatment a compound according to the invention or pharmaceutical composition thereof, wherein blood glucose normalization occurs with reduced risk of hypoglycemia.

In another embodiment the invention provides a method of preventing or ameliorating diabetic late complications comprising administering to a subject in need of such treatment a compound according to the invention or pharmaceutical composition thereof.

In another embodiment the invention provides a method of treating type 1 or 2 diabetes comprising administering to a subject in need of such treatment a compound according to the invention or pharmaceutical composition thereof, wherein the treatment does not result in a weight gain.

In another embodiment the invention provides a method of preventing diabetic ketoacidosis comprising administering to a subject in need of such treatment a compound according to the invention or pharmaceutical composition thereof.

Combination Treatment

In a further embodiment of the present invention the present compounds are administered in combination with one or more further active substances in any suitable ratios. Such further active agents may be selected from antidiabetic agents, antihyperlipidemic agents, antiobesity agents, antihypertensive agents and agents for the treatment of complications resulting from or associated with diabetes.

Suitable antidiabetic agents include insulin, GLP-1 (glucagon like peptide-1) derivatives such as those disclosed in WO 98/08871 (Novo Nordisk A/S), which is incorporated herein by reference, as well as orally active hypoglycemic agents.

Suitable orally active hypoglycemic agents preferably include imidazolines, sulfonylureas, biguanides, meglitinides, oxadiazolidinediones, thiazolidinediones, insulin sensitizers, α-glucosidase inhibitors, agents acting on the ATP-dependent potassium channel of the pancreatic β-cells eg potassium channel openers such as those disclosed in WO 97/26265, WO 99/03861 and WO 00/37474 (Novo Nordisk A/S) which are incorporated herein by reference, potassium channel openers, such as ormitiglinide, potassium channel blockers such as nateglinide or BTS-67582, glucagon antagonists such as those disclosed in WO 99/01423 and WO 00/39088 (Novo Nordisk A/S and Agouron Pharmaceuticals, Inc.), all of which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antihyperlipidemic agents and antilipidemic agents, compounds lowering food intake, and PPAR (peroxisome proliferatoractivated receptor) and RXR (retinoid X receptor) agonists such as ALRT-268, LG-1268 or LG-1069.

In one embodiment of the present invention, the present compounds are administered in combination with a sulphonylurea eg tolbutamide, chlorpropamide, tolazamide, glibenclamide, glipizide, glimepiride, glicazide or glyburide.

In one embodiment of the present invention, the present compounds are administered in combination with a biguanide eg metformin.

In one embodiment of the present invention, the present compounds are administered in combination with a meglitinide eg repaglinide or senaglinide/nateglinide.

In one embodiment of the present invention, the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097 (DRF-2344), WO 97/41119, WO 97/41120, WO 00/41121 and WO 98/45292 (Dr. Reddy's Research Foundation), which are incorporated herein by reference.

In one embodiment of the present invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313 (NN622/DRF-2725), WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In one embodiment of the present invention the present compounds are administered in combination with an α-glucosidase inhibitor e.g. voglibose, emiglitate, miglitol or acarbose.

In one embodiment of the present invention the present compounds are administered in combination with a glycogen phosphorylase inhibitor eg the compounds described in WO 97/09040 (Novo Nordisk A/S).

In one embodiment of the present invention the present compounds are administered in combination with an agent acting on the ATP-dependent potassium channel of the pancreatic β-cells eg tolbutamide, glibenclamide, glipizide, glicazide, BTS-67582 or repaglinide.

In one embodiment of the present invention the present compounds are administered in combination with nateglinide.

In one embodiment of the present invention the present compounds are administered in combination with an antihyperlipidemic agent or a antilipidemic agent eg cholestyramine, colestipol, clofibrate, gemfibrozil, lovastatin, pravastatin, simvastatin, probucol or dextrothyroxine.

Furthermore, the compounds according to the invention may be administered in combination with one or more antiobesity agents or appetite regulating agents.

Such agents may be selected from the group consisting of CART (cocaine amphetamine regulated transcript) agonists, NPY (neuropeptide Y) antagonists, MC3 (melanocortin 3) agonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 adrenergic agonists such as CL-316243, AJ-9677, GW-0604, LY362884, LY377267 or AZ-40140, MSH (melanocytestimulating hormone) agonists, MCH (melanocyte-concentrating hormone) antagonists, CCK (cholecystokinin) agonists, serotonin reuptake inhibitors (fluoxetine, seroxat or citalopram), serotonin and norepinephrine reuptake inhibitors, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA (dopamine) agonists (bromocriptin, doprexin), lipase/amylase inhibitors, PPAR modulators, RXR modulators, TR β agonists, adrenergic CNS stimulating agents, AGRP (agouti related protein) inhibitors, H3 histamine antagonists such as those disclosed in WO 00/42023, WO 00/63208 and WO 00/64884, which are incorporated herein by reference, exendin-4, GLP-1 agonists, ciliary neurotrophic factor, and oxyntomodulin. Further antiobesity agents are bupropion (antidepressant), topiramate (anticonvulsant), ecopipam (dopamine D1/D5 antagonist) and naltrexone (opioid antagonist).

In one embodiment of the present invention the antiobesity agent is leptin.

In one embodiment of the present invention the antiobesity agent is a serotonin and norepinephrine reuptake inhibitor eg sibutramine.

In one embodiment of the present invention the antiobesity agent is a lipase inhibitor eg orlistat.

In one embodiment of the present invention the antiobesity agent is an adrenergic CNS stimulating agent eg dexamphetamine, amphetamine, phentermine, mazindol phendimetrazine, diethylpropion, fenfluramine or dexfenfluramine.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19th Edition, Gennaro, Ed., Mack Publishing Co., Easton, Pa., 1995.

In one embodiment of the present invention, the present compounds are administered in combination with insulin, insulin derivatives or insulin analogues.

In one embodiment of the invention the insulin is an insulin derivative is selected from the group consisting of B29-N$^\epsilon$-myristoyl-des(B30) human insulin, B29-N$^\epsilon$-palmitoyldes(B30) human insulin, B29-N$^\epsilon$-myristoyl human insulin, B29-N$^\epsilon$-palmitoyl human insulin, B28-N$^\epsilon$-myristoyl Lys$^{B28}$Pro$^{B29}$ human insulin, B28-N$^\epsilon$-palmitoyl Lys$^{B28}$Pro$^{B29}$ human insulin, B30-N$^\epsilon$-myristoyl-Thr$^{B29}$Lys$^{B30}$ human insulin, B30-N$^\epsilon$-palmitoyl-Thr$^{B29}$Lys$^{B30}$ human insulin, B29-N$^\epsilon$—(N-palmitoyl-γ-glutamyl)-des(B30) human insulin, B29-N$^\epsilon$—(N-lithocholyl-γ-glutamyl)-des(B30) human insulin, B29-N$^\epsilon$-(ω-carboxyheptadecanoyl)-des(B30) human insulin and B29-N$^\epsilon$-(ω-carboxyheptadecanoyl) human insulin.

In another embodiment of the invention the insulin derivative is B29-N$^\epsilon$-myristoyl-des(B30) human insulin.

In a further embodiment of the invention the insulin is an acid-stabilised insulin. The acid-stabilised insulin may be selected from analogues of human insulin having one of the following amino acid residue substitutions:

A21G
A21G, B28K, B29P
A21G, B28D
A21G, B28E
A21G, B3K, B29E
A21G, desB27
A21G, B9E
A21G, B9D
A21G, B10E insulin.

In a further embodiment of the invention the insulin is an insulin analogue. The insulin analogue may be selected from the group consisting of An analogue wherein position B28 is Asp, Lys, Leu, Val, or Ala and position B29 is Lys or Pro; and
des(B28-B30), des(B27) or des(B30) human insulin.

In another embodiment the analogue is an analogue of human insulin wherein position B28 is Asp or Lys, and position B29 is Lys or Pro.

In another embodiment the analogue is des(B30) human insulin.

In another embodiment the insulin analogue is an analogue of human insulin wherein position B28 is Asp.

In another embodiment the analogue is an analogue wherein position B3 is Lys and position B29 is Glu or Asp.

In another embodiment the GLP-1 derivative to be employed in combination with a compound of the present invention refers to GLP-1(1-37), exendin-4(1-39), insulinotropic fragments thereof, insulinotropic analogues thereof and insulinotropic derivatives thereof. Insulinotropic fragments of GLP-1(1-37) are insulinotropic peptides for which the entire sequence can be found in the sequence of GLP-1 (1-37) and where at least one terminal amino acid has been deleted. Examples of insulinotropic fragments of GLP-1(1-37) are GLP-1(7-37) wherein the amino acid residues in positions 1-6 of GLP-1(1-37) have been deleted, and GLP-1 (7-36) where the amino acid residues in position 1-6 and 37 of GLP-1(1-37) have been deleted. Examples of insulinotropic fragments of exendin-4(1-39) are exendin-4(1-38) and exendin-4(1-31). The insulinotropic property of a compound may be determined by in vivo or in vitro assays well known in the art. For instance, the compound may be administered to an animal and monitoring the insulin concentration over time. Insulinotropic analogues of GLP-1(1-37) and exendin-4(1-39) refer to the respective molecules wherein one or more of the amino acids residues have been exchanged with other amino acid residues and/or from which one or more amino acid residues have been deleted and/or from which one or more amino acid residues have been added with the proviso that said analogue either is insulinotropic or is a prodrug of an insulinotropic compound. Examples of insulinotropic analogues of GLP-1(1-37) are e.g. Met$^8$-GLP-1(7-37) wherein the alanine in position 8 has been replaced by methionine and the amino acid residues in position 1 to 6 have been deleted, and AreGLP-1(7-37) wherein the valine in position 34 has been replaced with arginine and the amino acid residues in position 1 to 6 have been deleted. An example of an insulinotropic analogue of exendin-4(1-39) is Ser$^2$Asp$^3$-exendin-4 (1-39) wherein the amino acid residues in position 2 and 3 have been replaced with serine and aspartic acid, respectively (this particular analogue also being known in the art as exendin-3). Insulinotropic derivatives of GLP-1(1-37), exendin-4 (1-39) and analogues thereof are what the person skilled in the art considers to be derivatives of these peptides, i.e. having at least one substituent which is not present in the parent peptide molecule with the proviso that said derivative either is insulinotropic or is a prodrug of an insulinotropic compound. Examples of substituents are amides, carbohydrates, alkyl groups and lipophilic substituents. Examples of insulinotropic derivatives of GLP-1(1-37), exendin-4(1-39) and analogues thereof are GLP-1(7-36)-amide, Arg$^{34}$, Lys$^{26}$(N$^\epsilon$-(γ-Glu(N$^\alpha$-hexadecanoyl)))-GLP-1(7-37) and Tyr$^{31}$-exendin-4 (1-31)-amide. Further examples of GLP-1(1-37), exendin-4 (1-39), insulinotropic fragments thereof, insulinotropic analogues thereof and insulinotropic derivatives thereof are described in WO 98/08871, WO 99/43706, U.S. Pat. No. 5,424,286 and WO 00/09666.

In another embodiment of the present invention, the present compounds are administered in combination with more than one of the above-mentioned compounds e.g. in combination with metformin and a sulphonylurea such as glyburide; a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

It should be understood that any suitable combination of the compounds according to the invention with diet and/or exercise, one or more of the above-mentioned compounds and optionally one or more other active substances are considered to be within the scope of the present invention. In one embodiment of the present invention, the pharmaceutical composition according to the present invention comprises e.g. a compound of the invention in combination with metformin and a sulphonylurea such as glyburide; a compound of the invention in combination with a sulphonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Pharmaceutical Compositions

The compounds of the present invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as hard or soft capsules, tablets, troches, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, aqueous or oily suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain from 0.05 to about 1000 mg, preferably from about 0.1 to about 500 mg, and more preferred from about 0.5 mg to about 200 mg.

For parenteral routes such as intravenous, intrathecal, intramuscular and similar administration, typically doses are in the order of about half the dose employed for oral administration.

The compounds of this invention are generally utilized as the free substance or as a pharmaceutically acceptable salt thereof. Examples are an acid addition salt of a compound having the utility of a free base and a base addition salt of a compound having the utility of a free acid. The term "pharmaceutically acceptable salts" refers to non-toxic salts of the compounds of this invention which are generally prepared by reacting the free base with a suitable organic or inorganic acid or by reacting the acid with a suitable organic or inorganic base. When a compound according to the present invention contains a free base such salts are prepared in a conventional manner by treating a solution or suspension of the compound with a chemical equivalent of a pharmaceutically acceptable acid. When a compound according to the present invention contains a free acid such salts are prepared in a conventional manner by treating a solution or suspension of the compound with a chemical equivalent of a pharmaceutically acceptable base. Physiologically acceptable salts of a compound with a hydroxy group include the anion of said compound in combination with a suitable cation such as sodium or ammonium ion. Other salts which are not pharmaceutically acceptable may be useful in the preparation of compounds of the present invention and these form a further embodiment of the present invention.

For parenteral administration, solutions of the novel compounds of the formula (I) in sterile aqueous solution, aqueous propylene glycol or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid and lower alkyl ethers of cellulose. Examples of liquid carriers are syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the novel compounds of the present invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. Furthermore, the orally available formulations may be in the form of a powder or granules, a solution or suspension in an aqueous or non-aqueous liquid, or an oil-in-water or water-in-oil liquid emulsion.

Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,356,108; 4,166,452; and 4,265,874, incorporated herein by reference, to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyl-eneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alchol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the present invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectible aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the present invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the present invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

In addition, some of the compounds of the present invention may form solvates with water or common organic solvents. Such solvates are also encompassed within the scope of the present invention.

Thus, in a further embodiment, there is provided a pharmaceutical composition comprising a compound according to the present invention, or a pharmaceutically acceptable salt, solvate, or prodrug thereof, and one or more pharmaceutically acceptable carriers, excipients, or diluents.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet that may be prepared by conventional tabletting techniques may contain:
Core:

| | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9-40 T** | approx. 0.9 mg |

*Polacrillin potassium NF, tablet disintegrant, Rohm and Haas.
**Acylated monoglyceride used as plasticizer for film coating.

If desired, the pharmaceutical composition of the present invention may comprise a compound according to the present invention in combination with further active substances such as those described in the foregoing.

The present invention also provides a method for the synthesis of compounds useful as intermediates in the preparation of compounds of formula (I) along with methods for the preparation of compounds of formula (I). The compounds can be prepared readily according to the following reaction Schemes (in which all variables are as defined before, unless so specified) using readily available starting materials, reagents and conventional synthesis procedures. In these reactions, it is also possible to make use of variants which are themselves known to those of ordinary skill in this art, but are not mentioned in greater detail.

Pharmacological Methods
Glucokinase Activity Assay (I)

Glucokinase activity is assayed spectrometrically coupled to glucose 6-phosphate dehydrogenase to determine compound activation of glucokinase. The final assay contains 50 mM Hepes, pH 7.1, 50 mM KCl, 5 mM $MgCl_2$, 2 mM dithiothreitol, 0.6 mM NADP, 1 mM ATP, 0.195 µM G-6-P dehydrogenase (from Roche, 127 671), 15 nM recombinant human glucokinase. The glucokinase is human liver glucokinase N-terminally truncated with an N-terminal His-tag ($(His)_8$-VEQILA ... Q466) and is expressed in E. coli as a soluble protein with enzymatic activity comparable to liver extracted GK.

The purification of His-tagged human glucokinase (hGK) was performed as follows: The cell pellet from 50 ml E. coli culture was resuspended in 5 ml extraction buffer A (25 mM HEPES, pH 8.0, 1 mM $MgCl_2$, 150 mM NaCl, 2 mM mercaptoethanol) with addition of 0.25 mg/ml lysozyme and 50 µg/ml sodium azide. After 5 minutes at room temperature 5 ml of extraction buffer B (1.5 M NaCl, 100 mM $CaCl_2$, 100 mM $MgCl_2$, 0.02 mg/ml DNase 1, protease inhibitor tablet (Complete® 1697498): 1 tablet pr. 20 ml buffer) was added. The extract was then centrifugated at 15.000 g for 30 minutes. The resulting supernatant was loaded on a 1 ml Metal Chelate Affinity Chromatography (MCAC) Column charged with $Ni^{2+}$. The column is washed with 2 volumes buffer A containing 20 mM imidazole and the bound his-tagged hGK is subsequently eluted using a 20 minute gradient of 20 to 500 mM imididazol in buffer A. Fractions are examined using SDS-gel-electrophoresis, and fractions containing hGK (MW: 52 KDa) are pooled. Finally a gelfiltration step is used for final polishing and buffer exhange. hGK containing fractions are loaded onto a Superdex 75 (16/60) gelfiltration column and eluted with Buffer B (25 mM HEPES, pH 8.0, 1 mM $MgCl_2$, 150 mM NaCl, 1 mM Dithiothreitol). The purified hGK is examined by SDS-gel electrophoresis and MALDI mass spectrometry and finally 20% glycerol is added before freezing. The yield from 50 ml E. coli culture is generally approximately 2-3 mg hGK with a purity >90%.

The compound to be tested is added into the well in final 2.5% DMSO concentration in an amount sufficient to give a desired concentration of compound, for instance 1, 5, 10, 25 or 50 µM. The reaction starts after glucose is added to a final concentration of 2, 5, 10 or 15 mM. The assay uses a 96-well UV plate and the final assay volume used is 200 µl/well. The plate is incubated at 25° C. for 5 min and kinetics is measured at 340 nm in SpectraMax every 30 seconds for 5 minutes. Results for each compound are expressed as the fold activation of the glucokinase activity compared to the activation of the glucokinase enzyme in an assay without compound after having been subtracted from a "blank", which is without glucokinase enzyme and without compound. The compounds in each of the Examples exhibits activation of glucokinase in this assay. A compound, which at a concentration of at or below 30 µM gives 1.5-fold higher glucokinase activity than the result from the assay without compound, is deemed to be an activator of glucokinase.

The glucose sensitivity of the compounds are measured at a compound concentration of 10 µM and at glucose concentrations of 5 and 15 mM.

Glucokinase Activity Assay (II)

Determination of Glycogen Deposition in Isolated Rat Hepatocytes:

Hepatocytes are isolated from rats fed ad libitum by a two-step perfusion technique. Cell viability, assessed by trypan blue exclusion, is consistently greater than 80%. Cells are plated onto collagen-coated 96-well plates in basal medium (Medium 199 (5.5 mM glucose) supplemented with 0.1 µM dexamethasone, 100 units/ml penicillin, 100 mg/ml streptomycin, 2 mM L-glutamine and 1 nM insulin) with 4% FCS at a cell density of 30,000 cells/well. The medium is replaced with basal medium 1 hour after initial plating in order to remove dead cells. Medium is changed after 24 hours to basal medium supplemented with 9.5 mM glucose and 10 nM insulin to induce glycogen synthesis, and experiments are performed the next day. The hepatocytes are washed twice with prewarmed (37° C.) buffer A (117.6 mM NaCl, 5.4 mM KCl, 0.82 mM $Mg_2SO_4$, 1.5 mM $KH_2PO_4$, 20 mM HEPES, 9 mM $NaHCO_3$, 0.1% w/v HSA, and 2.25 mM $CaCl_2$, pH 7.4 at 37° C.) and incubated in 100 µl buffer A containing 15 mM glucose and increasing concentrations of the test compound, such as for instance 1, 5, 10, 25, 50 or 100 µM, for 180 minutes. Glycogen content is measured using standard procedures (Agius, L. et al, Biochem J. 266, 91-102 (1990). A compound, which when used in this assay gives an significant increase in glycogen content compared to the result from the assay without compound, is deemed to have activity in this assay.

Glucokinase Activity Assay (III)

Stimulation of Insulin Secretion by Glucokinase Activators in INS-1E Cells

The glucose responsive β-cell line INS-1E is cultivated as described by Asfari M et al., Endocrinology, 130, 167-178 (1992). The cells are then seeded into 96 well cell culture plates and grown to a density of approximately $5 \times 10^4$ per well. Stimulation of glucose dependent insulin secretion is tested by incubation for 2 hours in Krebs Ringer Hepes buffer at glucose concentrations from 2.5 to 15 mM with or without addition of glucokinase activating compounds in concentrations of for instance 1, 5, 10, 25, 50 or 100 µM, and the supernatants collected for measurements of insulin concentrations by ELISA (n=4). A compound, which when used in this assay gives an significant increase in insulin secretion in response to glucose compared to the result from the assay without compound, is deemed to have activity in this assay.

While the invention has been described and illustrated with reference to certain preferred embodiments thereof, those skilled in the art will appreciate that various changes, modifications and substitutions can be made therein without departing from the spirit and scope of the present invention. For example, effective dosages other than the preferred dosages as set forth herein may be applicable as a consequence of variations in the responsiveness of the mammal being treated for glucokinase-deficiency mediated disease(s). Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention.

EXAMPLES

Abbreviations used in the Schemes and Examples are as follows:

| | |
|---|---|
| br. s = | broad singlet |
| d = | doublet |
| g = | gram(s) |
| h = | hour(s) |
| MHz = | mega hertz |
| L = | liter(s) |
| M = | molar |
| m = | multiplet |
| mg = | milligram(s) |
| min = | minute(s) |
| mL = | milliliter(s) |
| mM = | millimolar |
| mmol = | millimole(s) |
| mol = | mole(s) |
| N = | normal |
| ppm = | parts per million |
| i.v. = | intravenous |
| m/z = | mass to charge ratio |
| MS = | mass spectrometry |
| HPLC = | high pressure liquid chromatography |
| HPLC-MS = | high pressure liquid chromatography - mass spectrometry |
| NMR = | nuclear magnetic resonance spectroscopy |
| p.o. = | per oral |
| rt = | room temperature |
| s = | singlet |
| s.c. = | subcutaneous |
| Boc = | tert-Butyloxycarbonyl |
| CDI = | carbonyldiimidazole |
| DCM (CH$_2$Cl$_2$) = | dichloromethane, methylenechloride |
| DEAD = | Diethyl azodicarboxylate |

-continued

| | |
|---|---|
| DIC = | 1,3-Diisopropyl carbodiimide |
| DCC = | 1,3-Dicyclohexyl carbodiimide |
| DIPEA = | N,N-diisopropylethylamine |
| DMA = | N,N-dimethylacetamide |
| DMAP = | 4-(N,N-dimethylamino)pyridine |
| DMF = | N,N-dimethylformamide |
| EDAC = | 1-(3-Dimethylaminopropyl)-3-ethyl-carbodiimide hydrochloride |
| Et$_2$O = | diethyl ether |
| EtOAc = | ethyl acetate |
| HOBt = | N-Hydroxybenzotriazole |
| LAH, (LiAlH$_4$) = | Lithiumaluminium hydride |
| MeCN = | acetonitrile |
| MeOH = | methanol |
| NMP = | N-methylpyrrolidin-2-one |
| NaH = | Sodium Hydride |
| t = | triplet |
| TEA (Et$_3$N) = | triethylamine |
| TFA = | trifluoroacetic acid |
| THF = | tetrahydrofuran |
| CDCl$_3$ = | deuterio chloroform |
| CD$_3$OD = | tetradeuterio methanol |
| DMSO-d$_6$ = | hexadeuterio dimethylsulfoxide |
| q = | quartet |

HPLC-MS

The RP-analysis was performed on an Agilent HPLC system (1100 degasser, 1100 pump, 1100 injector and a 1100 DAD) fitted with an Agilent MS detector system Model SL (MW 0-3000) and a S.E.D.E.R.E Model Sedex 75 ELS detector system using a Waters X-terra MS C18 column (5 µm, 3.0 mm×50 mm) with gradient elution, 5% to 100% solvent B (0.05% TFA in acetonitrile) in solvent A (0.05% TFA in water) within 6.75 min, 1.5 mL/min.

Preparative HPLC

The RP-purification was performed on a Gilson system (3 Gilson 306 pumps, Gilson 170 DAD detector and a Gilson 215 liquid handler) using a Waters X-terra RP (10 µm, 30 mm×150 mm) with gradient elution, 5% to 95% solvent B (0.05% TFA in acetonitrile) in solvent A (0.05% TFA in water) within 15 min, 40 mL/min, detection at 210 nm, temperature rt. The pooled fractions are either evaporated to dryness in vacuo, or evaporated in vacuo until the acetonitrile is removed, and then frozen and freeze dried.

NMR

Proton NMR spectra were recorded at ambient temperature using a Brucker Avance DPX 400 (400 MHz) with tetramethylsilane as an internal standard. Chemical shifts (δ) are given in ppm General The following examples and general procedures refer to intermediate compounds and final products for the compounds identified in the specification and in the synthesis schemes. The preparation of the compounds of the present invention is described in detail using the following examples. Occasionally, the reaction may not be applicable as described to each compound included within the disclosed scope of the invention. The compounds for which this occurs will be readily recognized by those skilled in the art. In these cases the reactions can be successfully performed by conventional modifications known to those skilled in the art, which is, by appropriate protection of interfering groups, by changing to other conventional reagents, or by routine modification of reaction conditions. Alternatively, other reactions disclosed herein or otherwise conventional will be applicable to the preparation of the corresponding compounds of the invention. In all preparative methods, all starting materials are known or may be prepared by a person skilled in the art in analogy with the preparation of similar known compounds.

The structures of the compounds are confirmed by either by nuclear magnetic resonance (NMR) and/or by HPLS-MS.

General Procedure (A)

Compounds of the formula (Ia) according to the invention wherein $R^1$, $R^2$ and A are substituents as further shown in the Examples can be prepared as outlined below:

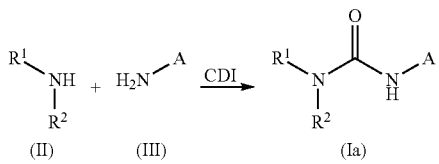

Step 1.

The aminoheterocycle ($NH_2A$) (III), can be converted using standard literature procedures (for example WO 2004/002481) to an acyl imidazonium intermediate with carbonyl diimidazole (CDI) or an equivalent of this in a solvent such as dichloromethane, dichloroethane, tetrahydrofuran, or DMF. Treatment with $R^1R^2NH$ (II) gives the compound of formula (Ia). The aminoheterocycle ($NH_2A$) or secondary amine ($R^1R^2NH$) can be either commercially available compounds or compounds that can be prepared following procedures described in the literature or prepared as described in the relevant example and general procedures.

Step 2.

In some cases it might be more convenient to generate the final substituents on $R^1$, $R^2$ and A after the urea formation. If for example the substituent on A in formula (Ia) contains an ester functionality this can be hydrolysed to the corresponding carboxylic acid using standard conditions for hydrolysis of esters. Suitable bases for the hydrolysis are NaOH and LiOH or equivalents of these in solvents like dioxane, THF, EtOH, MeOH and water or mixtures of these. The reactions can be performed at room temperature or at elevated temperatures.

General Procedure (B)

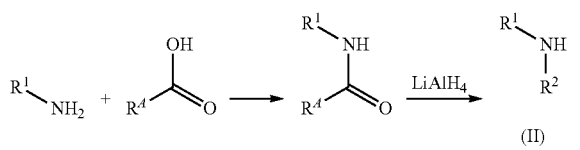

In case the primary amines ($R^1NH_2$) are not sufficiently reactive to undergo reductive amination or if the starting material is more readily available, the desired secondary amines can be prepared by initial formation of a secondary amide using a primary amine and an activated carboxylic acid or an equivalent thereof and subsequent reduction of the amide. The amide reduction can be performed in THF or similar solvents using lithium aluminium hydride or suitable equivalents. The primary amine and the carboxylic acid can be either commercially available compounds or compounds that can be prepared following procedures described in the literature or prepared as described in the relevant example and general procedures.

Synthesis of Central Intermediates

Preparation of (2-aminothiazol-5-ylsulfanyl)acetic acid ethyl ester

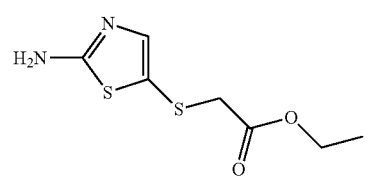

5-Bromo-2-aminothiazole (25 g, 96 mmol) and $K_2CO_3$ (26.5 g, 192 mmol) was suspended in DMF (50 mL) and stirred at 0° C. Ethyl thioglycolate (11.6 mL, 96 mmol) was added over 10 min. The reaction mixture was allowed to reach room temperature and stirred for a further 13 h. The mixture was divided between $H_2O$ (100 mL) and EtOAc (150 mL). Separation of the organic phase followed by extraction of the aqueous phase with EtOAc (2×100 mL). The combined organic phases were washed with aqueous $NaHCO_3$ (2000 mL), brine (2×200 mL) and dried ($MgSO_4$), filtered and evaporated. The crude product was dissolved in a small amount of DCM and purified by flash chromatography ($SiO_2$, 2% TEA in EtOAc-heptane, from 30%->100%) to give 50-65% pure (2-aminothiazol-5-ylsulfanyl)acetic acid ethyl ester as a dark red-brown oil.

$^1H$ NMR ($CDCl_3$): (ppm) 7.16 (s, 1H), 5.45 (br. s, 2H), 4.26 (q, 2H), 3.39 (s, 2H), 1.28 (t, 3H).

Preparation of 2-(2-amino-thiazol-5-ylsulfanyl)-2-methyl-propionic acid ethyl ester

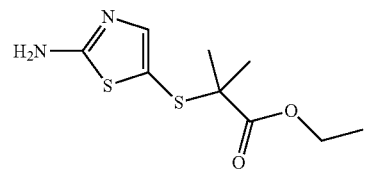

Step 1:

2-Aminothiazole (35 g, 350 mmol) and sodium thiocyanate (89 g, 1.08 mol) in MeOH (400 mL) was stirred at −10° C. Bromine (18.0 mL, 350 mmol) dissolved in MeOH (100 mL) saturated with NaBr was slowly added keeping the internal temperature between −10 and 0° C. After the addition the mixture was stirred at 0° C. for 3 h and the reaction mixture was poured into ice water (1500 mL). Aqueous $NH_4OH$ was added to pH ca 8.5 causing precipitation of light yellow crystals which were isolated by filtration, washed with ice water and dried in a vacuum oven to give 30 g (55%) 5-thiocyanato-thiazol-2-ylamine as light yellow crystals.

$^1H$ NMR (400 MHz, DMSO-$d_6$) (ppm) 7.83 (br. s., 2H) 7.44 (s, 1H)

Step 2:

In a nitrogen atmosphere 5-thiocyanato-thiazol-2-ylamine (10 g, 64 mmol) dissolved in MeOH (300 mL) was added 2,3-dihydroxy-1,4-dithiolbutane (DTT, 9.8 g, 64 mmol) and stirred at room temperature for 1½ h. Then 2-bromo-2-methyl-propionic acid ethyl ester (13.6 g, 70 mmol) and $K_2CO_3$ (10.5 g, 76 mmol) was added and the reaction mixture was stirred for further 13 hs. The reaction mixture was divided between water (500 mL) and EtOAc (500 mL). The aqueous phase was extracted with EtOAc (2×300 mL). The combined organic phases were washed with water (500 mL) and brine (2×400 mL) and dried ($MgSO_4$), filtered and evaporated. The crude product was dissolved in a small amount of DCM and purified by flash chromatography (heptane/EtOAc 2:1->1:2). Fractions containing the product were pooled and evaporated to a product containing impurities of DDT. This product was dissolved in diethyl ether (100 mL) and washed with water several times. The ether phase was dried ($MgSO_4$), filtered and evaporated to give 8.45 g (54%) of 95% pure 2-(2-amino-thiazol-5-ylsulfanyl)-2-methyl-propionic acid ethyl ester as light brown crystals.

$^1$H NMR (CDCl$_3$): (ppm) 7.10 (s, 1H) 5.30 (br. s., 2H) 4.16 (q, Hz, 2H) 1.50 (s, 6H) 1.27 (t, Hz, 3H)

Preparation of
3-(2-amino-thiazol-5-ylsulfanyl)-propionic acid
ethyl ester

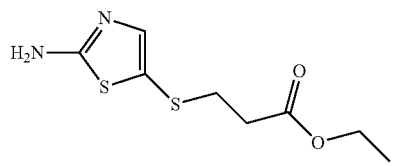

5-Bromo-2-aminothiazole (25 g, 96 mmol) in DMF (150 mL) was added K2CO3 (26.5 g, 192 mmol) and the mixture was purged with N2 for 5 min. The mixture was cooled to 0° C. on an ice bath before 3-mercaptopropionic acid ethyl ester (12.9 g, 96 mmol) was added dropwise over the course of 30 min. The reaction mixture was stirred for 16 hs before water (400 mL) was added. The aqueous mixture was extracted with Et2O (1×500 mL, 2×250 mL). The combined organic phases was washed with saturated NH4Cl (3×150 mL), dried ($MgSO_4$). The solvent was removed in vacuo to give a dark residue which was purified by column chromatography (SiO$_2$, EtOAc-heptane (1:1)). The solvent was removed in vacuo to give 11 g (49%) of the desired compound.

$^1$H NMR (400 MHz, CDCl3) (ppm) 7.1 (s, 1H), 5.2 (br. s, 2H), 4.2 (q, 2H), 2.8 (t, 2H), 2.6 (t, 2H), 1.3 (t, 3H).

Preparation of 3-(2-Amino-thiazol-5-ylsulfanyl)-2,2-dimethyl-propionic acid ethyl ester

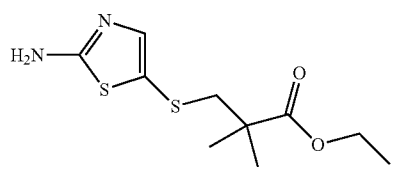 [SMILES: CCOC(=O)C(C)(C)CSc1cnc(N)s1]

5-thiocyanato-thiazol-2-ylamine (15.7 g) was dissolved in degassed methanol and sodium borohydride (4.5 g) in MeOH was added in one portion. The reaction was stirred for 30 min and 3-bromo-2,2-dimethyl-propionic acid (27 g) and diisopropylethylamine (17 mL) was added and the reaction stirred overnight at room temperature. The reaction was diluted with water, partially concentrated in vacuo and 5% citric acid was added until pH 4. The brown precipitate was filtered, washed with water and acetonitrile, and dried over night at room temperature. The residue was stirred with ethanol, filtered, washed with ethanol and dried in a vacuum oven at 40° C. to give 3-(2-amino-thiazol-5-ylsulfanyl)-2,2-dimethyl-propionic acid ethyl ester.

$^1$H NMR (CDCl$_3$): (ppm) 7.04 (s, 1H) 5.26 (br. s., 2H) 4.09 (q, 2H) 2.96 (s, 2H) 1.27 (s, 6H) 1.24 (t, 3H)

Example 1

3-{2-[3-[2-(2-Chloro-benzyloxy)-ethyl]-3-(trans-4-methyl-cyclohexyl)-ureido]-thiazol-5-ylsulfanyl}-2,2-dimethyl-propionic acid

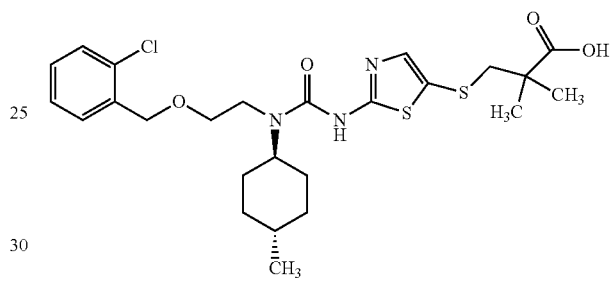

A refluxing solution of 4-trans-methyl-cyclohexylamine hydrochloride (13.9 g, 93 mmol) and potassium carbonate (25.6 g, 186 mmol) in acetonitrile (100 mL) was added a solution of 2-(benzyloxy)-ethylbromide (20 g, 93 mmol) in acetonitrile (50 mL) over the course of 30 min. The mixture was refluxed for 2 hs before it was allowed to reach room temperature whereupon a solution of di-tert-butyl-dicarbonate (1M, THF, 93 mL) was added. The reaction mixture was stirred at room temperature for 18 hours before the volatiles were removed in vacuo. The residue was dissolved in diethyl ether (150 mL) and washed with water (2×100 mL), dried ($MgSO_4$), filtered and concentrated in vacuo. The residue was purified by flash chromatography (SiO$_2$, heptane to 10% EtOAc in heptane) to give 23.7 g of (2-benzyloxy-ethyl)-(4-trans-methyl-cyclohexyl)-carbamic acid tert-butyl ester.

This was dissolved in abs. ethanol (250 mL) and Pd/C (10%, 2.0 g) was added. The reaction mixture was stirred under H$_2$ at room temperature for 4 hs before it was filtered through a pad of Celite and subsequently concentrated in vacuo to give 17.5 g of (2-hydroxy-ethyl)-(trans-4-methyl-cyclohexyl)-carbamic acid tert-butyl ester.

To a mixture of (2-hydroxy-ethyl)-(trans-4-methyl-cyclohexyl)-carbamic acid tert-butyl ester (0.75 g, 2.91 mmol) and 2-chlorobenzylbromide (0.90, 4.37 mmol) in DMF (8 mL) was added NaH (60% in mineral oil, 0.23 g, 5.83 mmol) and the reaction mixture was stirred for 16 h. H$_2$O (4 mL) was added and the mixture was extracted with diethyl ether (3×5 mL). The organic phase was collected and the solvent was removed in vacuo to give the crude product of [2-(2-chloro-benzyloxy)-ethyl]-(4-methyl-cyclohexyl)-carbamic acid tert-butyl ester. This was dissolved in DCM (4 mL) and TFA (4 mL) and the mixture was stirred for 2 hs before the volatiles were removed in vacuo.

The crude product was purified on preparative HPLC to give 515 mg (45%) of the TFA salt of [2-(2-chloro-benzyloxy)-ethyl]-(trans-4-methyl-cyclohexyl)-amine.

The TFA salt of [2-(2-chloro-benzyloxy)-ethyl]-(trans-4-methyl-cyclohexyl)-amine (169 mg, 0.60 mmol) in THF (5 mL) was added 3-(2-amino-thiazol-5-ylsulfanyl)-2,2-dimethyl-propionic acid ethyl ester (195 mg, 0.75 mmol), CDI (243 mg, 1.50 mmol) and DMAP (3.7 mg, 0.03 mmol). The reaction mixture was stirred for 18 h. Ethanol (1 mL) and NaOH (2.5 N, 3 mL, 7.5 mmol) was added and the reaction mixture was heated to 75° C. for 5 h. The mixture was allowed to cool to rt before pH was adjusted (pH<1). The precipitate was filtered off and purified by preparative HPLC to give 170 mg (53%) of 3-{2-[3-[2-(2-Chloro-benzyloxy)-ethyl]-3-(trans-4-methyl-cyclohexyl)-ureido]-thiazol-5-ylsulfanyl}-2,2-dimethyl-propionic acid.

$^1$H NMR (300 MHz, DMSO-$d_6$) (ppm) 7.48-7.54 (m, 1H) 7.41-7.46 (m, 1H) 7.29-7.35 (m, 3H) 4.60 (s, 2H) 3.86-4.00 (m, 1H) 3.56-3.64 (m, 2H) 3.43-3.55 (m, 3H) 2.95 (s, 2H) 1.63-1.72 (m, 2H) 1.50-1.62 (m, 4H) 1.18 (s, 6H) 0.96-1.09 (m, 2H) 0.86 (d, 3H)

HPLC-MS: m/z=540 (M+1)

Example 2

3-{2-[3-(2-Benzyloxy-ethyl)-3-(trans-4-methyl-cyclohexyl)-ureido]-thiazol-5-ylsulfanyl}-2,2-dimethyl-propionic acid

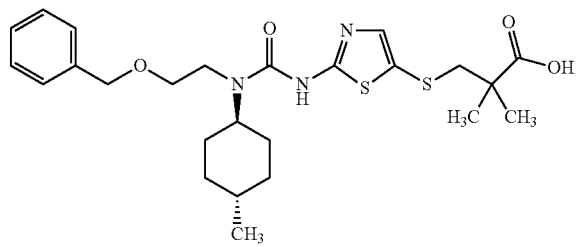 [SMILES: CC(C)(CSc1cnc(NC(=O)N(CCOCc2ccccc2)[C@H]2CC[C@H](C)CC2)s1)C(=O)O]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using benzyl bromide and 3-(2-amino-thiazol-5-ylsulfanyl)-2,2-dimethyl-propionic acid ethyl ester.

$^1$H NMR (300 MHz, CDCl$_3$) (ppm) 7.23-7.37 (m, 5H) 7.16 (s, 1H) 4.54 (s, 2H) 3.65-3.96 (m, 1H) 3.56-3.67 (m, 2H) 3.41-3.53 (m, 2H) 2.94 (br. s., 2H) 1.65-1.89 (m, 4H) 1.22-1.58 (m, 11H) 0.84-0.97 (m, 3H)

HPLC-MS: m/z=506 (M+1)

Example 3

2-{2-[3-(2-Benzyloxy-ethyl)-3-(trans-4-methyl-cyclohexyl)-ureido]-thiazol-5-ylsulfanyl}-2-methyl-propionic acid

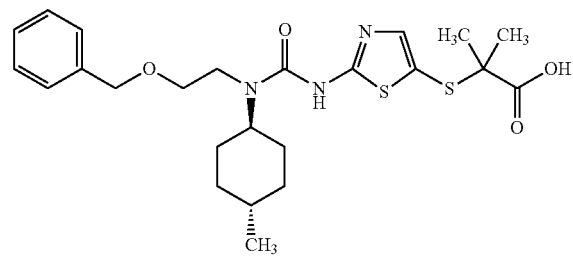 [SMILES: CC(C)(Sc1cnc(NC(=O)N(CCOCc2ccccc2)[C@H]2CC[C@H](C)CC2)s1)C(=O)O]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using benzyl bromide and 2-(2-amino-thiazol-5-ylsulfanyl)-2-methyl-propionic acid ethyl ester.

$^1$H NMR (300 MHz, CDCl$_3$) (ppm) 7.25-7.37 (m, 5H) 7.13 (br. s., 1H) 4.58 (s, 2H) 3.86-4.15 (m, 1H) 3.59-3.68 (m, 2H) 3.51-3.58 (m, 2H) 1.70-1.82 (m, 4H) 1.41-1.61 (m, 7H) 1.06-1.37 (m, 4H) 0.89 (d, 3H)

HPLC-MS: m/z=492 (M+1)

Example 4

2-{2-[3-[3-(2-Methoxy-phenylsulfanyl)-propyl]-3-(trans-4-methyl-cyclohexyl)-ureido]-thiazol-5-ylsulfanyl}-2-methyl-propionic acid

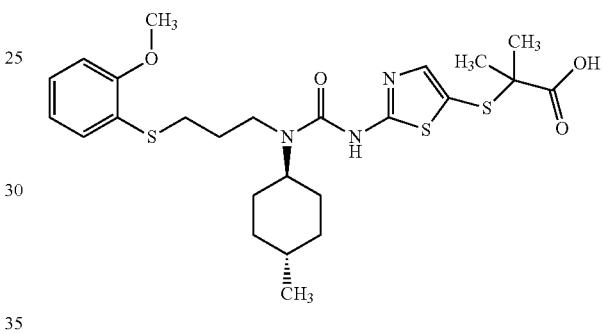

A refluxing solution of trans-4-methyl-cyclohexylamine (6.58 g, 44.2 mmol) and K$_2$CO$_3$ (12.2 g, 88.3 mmol) in MeCN (100 mL) was slowly added 3-bromopropyl benzyl ether (10.1 g, 44.2 mmol). The reaction mixture was refluxed for 2 h. The reaction was cooled to rt. and left for 18 h.

Di-tert-butyl dicarbonate (9.45 g, 44.2 mmol) in THF (44 mL) was added and the reaction mixture was left for 3 days. The volatiles were removed in vacuo and the residue was divided between diethyl eter (100 mL) and H$_2$O (100 mL). The aqueous phase was extracted with diethyl ether (100 mL) and the combined organic fractions was dried (MgSO$_4$), filtered and concentrated in vacuo. Flash chromatography (SiO$_2$, 5-8% EtOAc in heptane) gave 11.7 g of (3-benzyloxy-propyl)-(trans-4-methyl-cyclohexyl)-carbamic acid tert-butyl ester.

The ester (11.7 g, 32.4 mmol) in EtOH (50 mL) was added Pd/C (20%, wet, 1.17 g) and stirred for 16 h under an atmosphere of H$_2$ (balloon). Another batch of Pd/C (20%, wet, 1.17 g) was added and the reaction was stirred under H$_2$ for 20 h.

The reaction mixture was filtered through a pad of Celite and the filtrate was evaporated in vacuo to give (3-hydroxy-propyl)-(trans-4-methyl-cyclohexyl)-carbamic acid tert-butyl ester.

A solution of 3-(hydroxy-propyl)-(trans-4-methyl-cyclohexyl)-carbamic acid tert-butyl ester (467 mg, 1.72 mmol) and DIPEA (0.60 mL, 3.33 mmo) in DCM (5 mL) cooled on an ice bath was added methanesulfunyl chloride (0.146 mL, 1.89 mmol) and the reaction mixture was stirred for 1 h. at 0° C., before H$_2$O (25 mL) was introduced. The organic phase was dried (MgSO$_4$), filtered concentrated in vacuo. The residue was dissolved in MeCN (5 mL) containing K$_2$O$_3$ (475 mg, 3.44 mmol) and 2-methoxy-benzenethiol (241 mg, 1.72 mmol) was introduced. The reaction mixture was stirred for 48 h before the sovent was removed in vacuo. The residue was added DCM (15 mL) and H$_2$O (15 mL) and the phases were separated. The organic phase was added TFA (15 mL) and the mixture was stirred for 18 h at rt. The volatiles were removed in vacuo to give the crude secondary amine that was purified by preparative HPLC to give 155 mg of the TFA salt of [3-(2-methoxy-phenylsulfanyl)-propyl]-(trans-4-methyl-cyclohexyl)-amine.

[3-(2-Methoxy-phenylsulfanyl)-propyl]-(trans-4-methyl-cyclohexyl)-amine was transformed to 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using the procedure described for the synthesis of 2-{2-[3-[2-(2-chloro-benzyloxy)-ethyl]-3-(trans-4-methyl-cyclohexyl)-ureido]-thiazol-5-ylsulfanyl}-2,2-dimethyl-propionic acid.

$^1$H NMR (400 MHz, DMSO-d$_6$) (ppm) 7.40 (s, 1H) 7.27 (d, 1H) 7.17 (t, 1H) 6.90-6.99 (m, 2H) 3.88-4.01 (m, 1H) 3.80 (s, 3H) 2.88-2.94 (m, 2H) 1.62-1.79 (m, 4H) 1.41-1.56 (m, 4H) 1.39 (s, 6H) 1.20-1.34 (m, 1H) 0.95-1.08 (m, 2H) 0.87 (d, 3H)

HPLC-MS: m/z=538 (M+1)

Example 5

2-Methyl-2-{2-[3-(trans-4-methyl-cyclohexyl)-3-(4-phenyl-butyl)-ureido]-thiazol-5-ylsulfanyl}-propionic acid

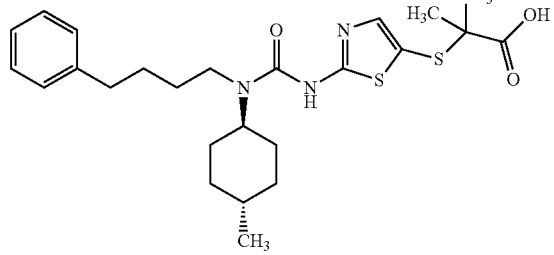

A solution of 4-phenyl-1-butanol (5.0 g, 33.3 mmol) and DIPEA (8.55 mL, 49.9 mmol) in DCM (100 mL) cooled on an ice bath were added methanesulfunyl chloride (2.83 mL, 36.6 mmol). The reaction mixture was stirred for 15 min before the cooling bath was removed and the reaction mixture was allowed to warm up to rt. After additional 45 min the mixture was added HCl (0.1 N, 100 mL) and the phases were separated. The aqueous phase were extracted with DCM (2×150 mL) and the combined organic phases were dried (MgSO$_4$), filtered and concentrated in vacuo to give the crude product of methanesulfonic acid 4-phenyl-butyl ester.

The intermediate was dissolved in MeCN (150 mL) and added trans-4-methylcyclohexylamine hydrochloride (4.98 g, 33.3 mmol) and K$_2$CO$_3$ (9.2 g, 66.6 mmol). The reaction mixture was refluxed for 18 h before the volatiles were removed in vacuo. The residue was divided between H$_2$O (100 mL) and diethylether (100 mL). The aqueous phase was extracted with diethylether (2×50 mL). The organic fractions were collected, dried (MgSO$_4$), filtered and concentrated in vacuo. The residue was purified by preparative HPLC to give 6.04 g of the TFA salt of (trans-4-methyl-cyclohexyl)-(4-phenyl-butyl)-amine.

This was transformed to 2-methyl-2-{2-[3-(trans-4-methyl-cyclohexyl)-3-(4-phenyl-butyl)-ureido]-thiazol-5-ylsulfanyl}-propionic acid using the procedure described for the synthesis of 2-{2-[3-[2-(2-chloro-benzyloxy)-ethyl]-3-(trans-4-methyl-cyclohexyl)-ureido]-thiazol-5-ylsulfanyl}-2,2-dimethyl-propionic acid.

$^1$H NMR (400 MHz, DMSO-d$_6$) (ppm) 7.35 (s, 1H) 7.19-7.26 (m, 2H) 7.10-7.18 (m, 3H) 3.83-3.95 (m, 1H) 3.52-3.62 (m, 2H) 3.14-3.24 (m, 2H) 2.51-2.58 (m, 2H) 2.45-2.49 (m, 9H) 1.70-1.75 (m, 1H) 1.60-1.67 (m, 2H) 1.40-1.57 (m, 9H) 1.35 (s, 6H) 0.92-1.07 (m, 2H) 0.82 (d, 3H)

HPLC-MS: m/z=490 (M+1)

Example 6

2-{2-[3-[2-(4-Methoxy-phenyl)-ethyl]-3-(trans-4-methyl-cyclohexyl)-ureido]-thiazol-5-ylsulfanyl}-2-methyl-propionic acid

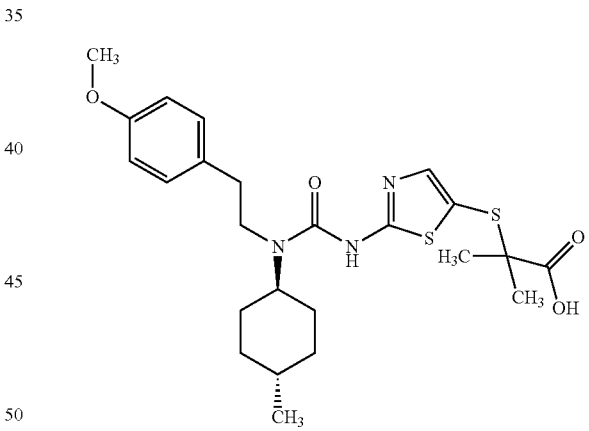

The compound was prepared following an analogous procedure to the one described for the synthesis of 2-methyl-2-{2-[3-(trans-4-methyl-cyclohexyl)-3-(4-phenyl-butyl)-ureido]-thiazol-5-ylsulfanyl}-propionic acid using 2-(4-methoxy-phenyl)-ethanol and 2-(2-amino-thiazol-5-ylsulfanyl)-2-methyl-propionic acid ethyl ester.

$^1$H NMR (300 MHz, CDCl$_3$) (ppm) 7.20 (d, 2H) 7.08 (s, 1H) 6.84 (d, 2H) 3.69-3.86 (m, 4H) 3.36-3.62 (m, 2H) 2.87 (t, 2H) 1.71-1.92 (m, 4H) 1.46-1.68 (m, 8H) 1.02-1.46 (m, 3H) 0.91 (d, 3H)

HPLC-MS: m/z=492 (M+1)

Example 7

3-{2-[3-[2-(4-Methoxy-phenyl)-ethyl]-3-(trans-4-methyl-cyclohexyl)-ureido]-thiazol-5-ylsulfanyl}-2,2-dimethyl-propionic acid

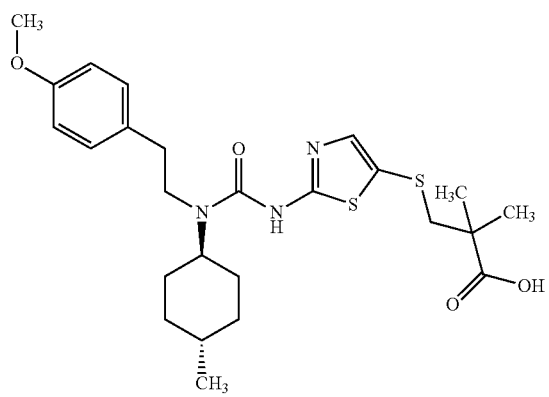 [SMILES: COc1ccc(CCN(C(=O)Nc2ncc(SCC(C)(C)C(=O)O)s2)[C@H]2CC[C@H](C)CC2)cc1]

The compound was prepared following an analogous procedure to the one described for the synthesis of 2-methyl-2-{2-[3-(trans-4-methyl-cyclohexyl)-3-(4-phenyl-butyl)-ureido]-thiazol-5-ylsulfanyl}-propionic acid using 2-(4-methoxy-phenyl)-ethanol and 3-(2-amino-thiazol-5-ylsulfanyl)-2,2-dimethyl-propionic acid ethyl ester.

$^1$H NMR (300 MHz, CDCl$_3$) (ppm) 7.21 (s, 1H) 7.10-7.19 (m, 2H) 6.80 (d, 2H) 3.81-3.98 (m, 1H) 3.78 (s, 3H) 3.27-3.50 (m, 2H) 2.97 (s, 2H) 2.76-2.86 (m, 2H) 1.70-1.95+1.41-1.58+1.27-1.37 (m, 15H) 0.85-0.98 (m, 3H)

HPLC-MS: m/z=506 (M+1)

Example 8

{2-[3-(trans-4-Methyl-cyclohexyl)-3-(2-phenylsulfanyl-ethyl)-ureido]-thiazol-5-ylsulfanyl}-acetic acid

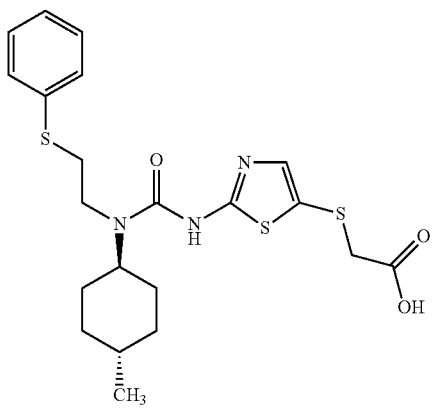 [SMILES: C[C@H]1CC[C@H](N(CCSc2ccccc2)C(=O)Nc2ncc(SCC(=O)O)s2)CC1]

To a solution of (2-Hydroxy-ethyl)-(trans-4-methyl-cyclohexyl)-carbamic acid tert-butyl ester (0.50 g, 1.94 mmol) in THF (20 mL) was added DEAD (372 mg, 2.14 mmol) and resin bound triphenyl phosphine (polystyrene 2% cross linking, loading=3 mmol/g, 0.97 g). The mixture was stirred for 15 m before thiophenol (0.21 g, 1.94 mmol) was added. The mixture was stirred for 18 h before another portion of resin bound triphenyl phosphine (0.97 g) and DEAD (372 mg, 2.14 mmol) was added. The mixture was stirred for 1 h before a new portion of thiophenol (0.21 g, 1.94 mmol) was added. The mixture was stirred for 18 h before it was filtered. The resin was washed with THF (2×20 mL) and the combined filtrates were concentrated in vacuo. The residue was divided between DCM (100 mL) and H$_2$O (100 mL). The aqueous layer was extracted once more with DCM (100 mL). The organic fractions were combined, dried (MgSO$_4$), filtered and concentrated in vacuo to give the crude intermediate (4-methyl-cyclohexyl)-(2-phenylsulfanyl-ethyl)-amine.

The amine was coupled and the resulting ester hydrolyzed as previously described for 3-{2-[3-[2-(2-Chloro-benzyloxy)-ethyl]-3-(trans-4-methyl-cyclohexyl)-ureido]-thiazol-5-ylsulfanyl}-2,2-dimethyl-propionic acid.

$^1$H NMR (400 MHz, DMSO-d$_6$) (ppm) 7.38-7.49 (m, 3H) 7.34 (t, 2H) 7.14-7.28 (m, 1H) 3.82-4.09 (m, 1H) 3.49 (s, 2H) 2.99-3.16 (m, 2H) 1.62 (t, 4H) 1.29-1.45 (m, 2H) 1.15-1.29 (m, 1H) 0.93-1.13 (m, 2H) 0.85 (d, 3H)

HPLC-MS: m/z=466 (M+1)

Example 9

2-Methyl-2-{2-[3-(trans-4-methyl-cyclohexyl)-3-(2-phenylsulfanyl-ethyl)-ureido]-thiazol-5-ylsulfanyl}-propionic acid

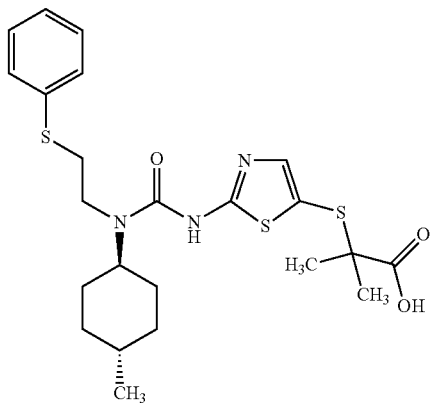 [SMILES: CC(C)(Sc1cnc(NC(=O)N(CCSc2ccccc2)[C@H]2CC[C@H](C)CC2)s1)C(=O)O]

The compound was prepared following an analogous procedure to the one described for the synthesis of {2-[3-(trans-4-methyl-cyclohexyl)-3-(2-phenylsulfanyl-ethyl)-ureido]-thiazol-5-ylsulfanyl}-acetic acid using 2-(2-amino-thiazol-5-ylsulfanyl)-2-methyl-propionic acid ethyl ester.

HPLC-MS: m/z=494 (M+1)

Example 10

{2-[3-(2-Benzylsulfanyl-ethyl)-3-(trans-4-methyl-cyclohexyl)-ureido]-thiazol-5-ylsulfanyl}-acetic acid

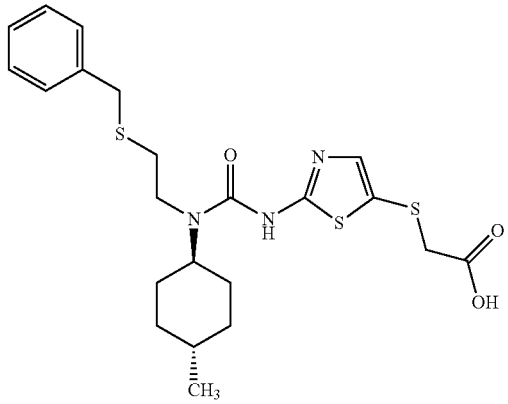

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using benzylsulfanyl-acetic acid and (2-aminothiazol-5-ylsulfanyl)acetic acid ethyl ester.

¹H NMR (400 MHz, DMSO-d₆) (ppm) 7.27-7.51 (m, 5H) 7.15-7.27 (m, 1H) 3.72-4.02 (m, 3H) 3.48 (s, 2H) 3.35 (2H, under water signal) 2.5 (2H, under DMSO residual peak) 1.64 (d, 2H) 1.49 (d, 2H) 1.19-1.44 (m, 3H) 0.93-1.14 (m, 2H) 0.87 (d, 3H))

HPLC-MS: m/z=480 (M+1)

Example 11

{2-[3-(trans-4-Methyl-cyclohexyl)-3-(3-phenylsulfanyl-propyl)-ureido]-thiazol-5-ylsulfanyl}-acetic acid

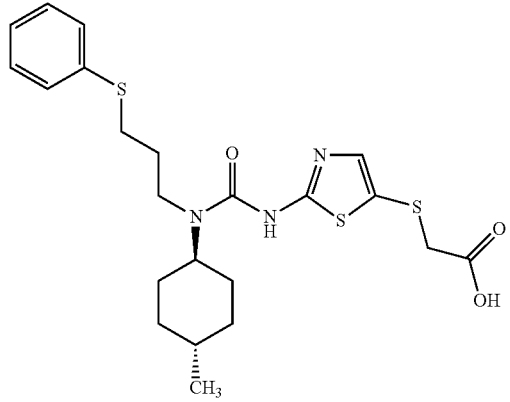 [SMILES: C[C@H]1CC[C@H](N(CCCSc2ccccc2)C(=O)Nc2ncc(SCC(=O)O)s2)CC1]

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using thiophenol and (2-aminothiazol-5-ylsulfanyl)acetic acid ethyl ester.

¹H NMR (400 MHz, CDCl₃) (ppm) 7.35 (d, 2H) 7.29 (t, 3H) 7.18 (t, 1H) 3.38-3.45 (m, 2H) 3.34 (s, 2H) 2.99-3.07 (m, 2H) 1.88-1.97 (m, 2H) 1.60-1.75 (m, 4H) 1.37-1.51 (m, 2H) 1.22-1.35 (m, 2H) 1.03-1.18 (m, 2H) 0.90 (d, 3H)

HPLC-MS: m/z=480 (M+1)

Example 12

2-Methyl-2-{2-[3-(trans-4-methyl-cyclohexyl)-3-(3-phenylsulfanyl-propyl)-ureido]-thiazol-5-ylsulfanyl}-propionic acid

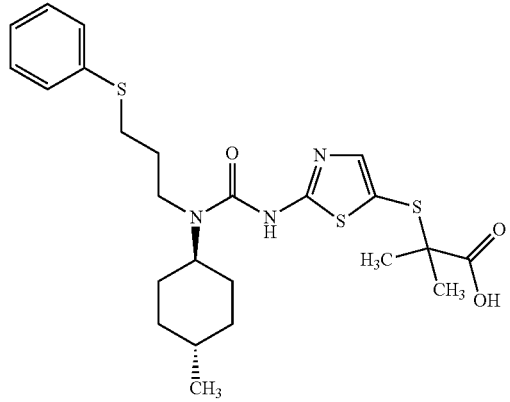 [SMILES: CC(C)(Sc1cnc(NC(=O)N(CCCSc2ccccc2)[C@H]2CC[C@H](C)CC2)s1)C(=O)O]

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using thiophenol and 2-(2-amino-thiazol-5-ylsulfanyl)-2-methyl-propionic acid ethyl ester.

¹H NMR (400 MHz, DMSO-d₆) (ppm) 7.40 (s, 1H) 7.29-7.36 (m, 4H) 7.18 (t, 1H) 3.89-3.99 (m, 1H) 3.30-3.37 (m, 2H) 2.99 (t, 2H) 1.71-1.81 (m, 2H) 1.61-1.69 (m, 2H) 1.36-1.56 (m, 10H) 1.22-1.34 (m, 1H) 0.95-1.08 (m, 2H) 0.86 (d, 3H)

HPLC-MS: m/z=508 (M+1)

Example 13

2,2-Dimethyl-3-{2-[3-(trans-4-methyl-cyclohexyl)-3-(3-phenylsulfanyl-propyl)-ureido]-thiazol-5-ylsulfanyl}-propionic acid

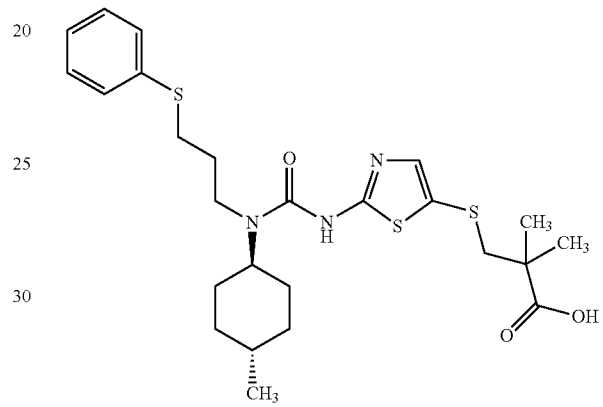

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using thiophenol and 3-(2-amino-thiazol-5-ylsulfanyl)-2,2-dimethyl-propionic acid ethyl ester.

¹H NMR (400 MHz, DMSO-d₆) (ppm) 7.29-7.37 (m, 5H) 7.18 (t, 1H) 3.89-4.00 (m, 1H) 3.28-3.41 (m, 2H) 2.91-3.02 (m, 4H) 1.71-1.81 (m, 2H) 1.65 (d, 2H) 1.37-1.55 (m, 4H) 1.21-1.34 (m, 1H) 1.18 (s, 6H) 0.95-1.07 (m, 2H) 0.86 (d, 3H)

HPLC-MS: m/z=522 (M+1)

Example 14

2-Methyl-2-{2-[3-(trans-4-methyl-cyclohexyl)-3-(3-phenoxy-propyl)-ureido]-thiazol-5-ylsulfanyl}-propionic acid

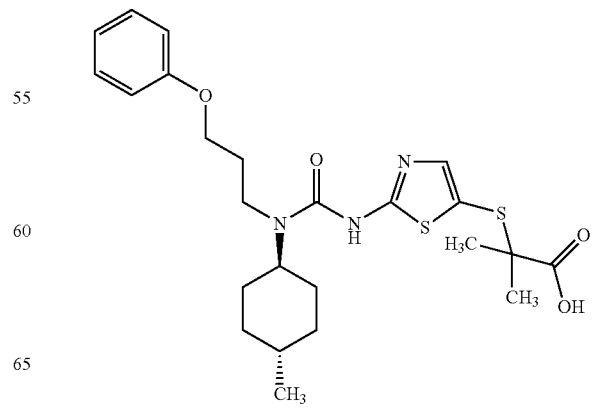

(3-Hydroxy-propyl)-(trans-4-methyl-cyclohexyl)-carbamic acid tert-butyl ester (1.5 g, 5.53 mmol) and phenol (0.52 g, 5.53 mmol) in dry THF (15 mL) was added DEAD (1.06 g, 6.08 mmol) and resin bound triphenyl phosphine (polystyrene, 2% cross linking, loading=3 mmol/g, 2.76 g). The reaction mixture was gently stirred for 18 h before the resin was filtered off and washed with THF (2×15 mL). The fitrate was concentrated in vacuo and the resulting residue was purified (SiO$_2$, 0-20% EtOAc in heptane) to give 0.99 g of (4-methyl-cyclohexyl)-(3-phenoxy-propyl)-carbamic acid tert-butyl ester. This was dissolved in DCMTFA ((3:1), 16 mL) and the mixture was stirred for 18 h before the solvent was removed in vacuo to give 0.75 g of the TFA salt of (4-methyl-cyclohexyl)-(3-phenoxy-propyl)-amine.

The amine was coupled and the resulting ester hydrolyzed as previously described for 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 2-(2-aminothiazol-5-ylsulfanyl)-2-methyl-propionic acid ethyl ester.

$^1$H NMR (400 MHz, DMSO-d$_6$) (ppm) 7.36 (s, 1H) 7.25 (t, 2H) 6.86-6.93 (m, 3H) 3.89-4.00 (m, 3H) 3.31-3.54 (m, 2H) 1.86-1.95 (m, 2H) 1.43-1.66 (m, 6H) 1.17-1.38 (m, 7H) 0.95-1.08 (m, 2H) 0.82 (d, 3H)

HPLC-MS: m/z=492 (M+1)

Example 15

2,2-Dimethyl-3-{2-[3-(trans-4-methyl-cyclohexyl)-3-(3-phenoxy-propyl)-ureido]-thiazol-5-ylsulfanyl}-propionic acid

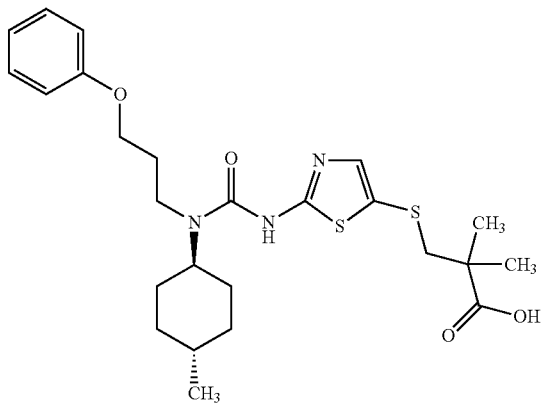 [SMILES: CC(C)(CSc1cnc(NC(=O)N(CCCOc2ccccc2)[C@H]2CC[C@H](C)CC2)s1)C(=O)O]

The compound was prepared following an analogous procedure to the one described for the synthesis 2-methyl-2-{2-[3-(trans-4-methyl-cyclohexyl)-3-(3-phenoxy-propyl)-ureido]-thiazol-5-ylsulfanyl}-propionic acid using phenol and 3-(2-amino-thiazol-5-ylsulfanyl)-2,2-dimethyl-propionic acid ethyl ester.

$^1$H NMR (400 MHz, CDCl$_3$) (ppm) 7.26 (t, 2H) 7.18 (s, 1H) 6.79-7.00 (m, 3H) 3.92-4.15 (m, 3H) 3.42 (t, 2H) 2.95 (br. s., 2H) 2.01-2.12 (m, 2H) 1.69-1.91 (m, 4H) 1.46-1.60 (m, 2H) 1.23-1.38 (m, 9H) 0.85-0.97 (m, 3H)

HPLC-MS: m/z: 506 (M+1)

Example 16

{2-[3-(trans-4-Methyl-cyclohexyl)-3-(4-phenyl-butyl)-ureido]-thiazol-5-ylsulfanyl}-acetic acid

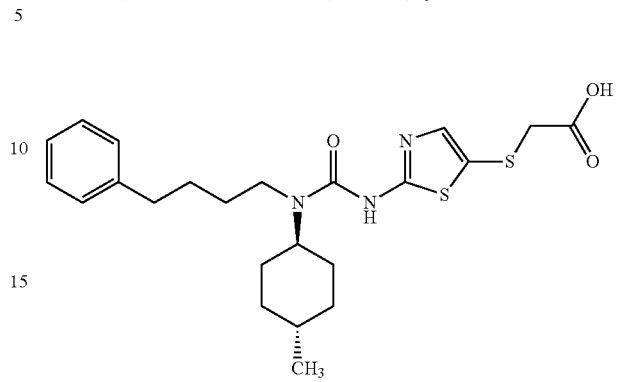

The compound was prepared following an analogous procedure to the one described for the synthesis of 2-methyl-2-{2-[3-(trans-4-methyl-cyclohexyl)-3-(4-phenyl-butyl)-ureido]-thiazol-5-ylsulfanyl}-propionic acid using 4-phenyl butan-1-ol and (2-aminothiazol-5-ylsulfanyl)acetic acid ethyl ester.

$^1$H NMR (400 MHz, DMSO-d$_6$) (ppm) 7.37 (s, 1H) 7.19-7.26 (m, 2H) 7.10-7.18 (m, 3H) 3.82-3.95 (m, 1H) 3.56 (t, 3H) 3.43 (s, 3H) 3.15-3.21 (m, 2H) 2.55 (t, 2H) 1.70-1.74 (m, 2H) 1.60-1.66 (m, 2H) 1.39-1.57 (m, 7H) 1.19-1.33 (m, 1H) 0.93-1.05 (m, 2H) 0.82 (d, 3H)

HPLC-MS: m/z=462 (M+1)

Example 17

2-{2-[3-(2-Indan-2-yl-ethyl)-3-(trans-4-methyl-cyclohexyl)-ureido]-thiazol-5-ylsulfanyl}-2-methyl-propionic acid

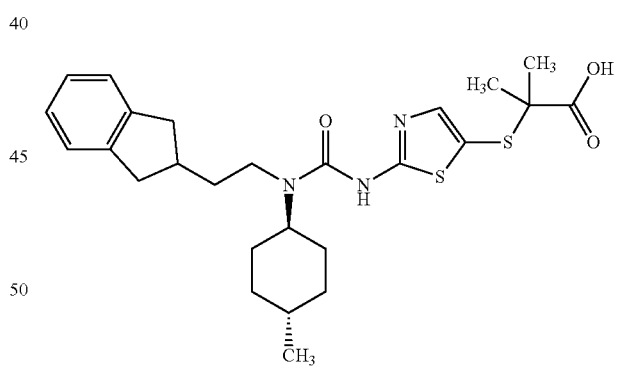

The compound was prepared following an analogous procedure to the one described for the synthesis of 2-methyl-2-{2-[3-(trans-4-methyl-cyclohexyl)-3-(4-phenyl-butyl)-ureido]-thiazol-5-ylsulfanyl}-propionic acid using 2-indan-2-yl-ethanol (prepared as described in J. Med. Chem. 1994, 37, 13, 2071-2078) and 2-(2-amino-thiazol-5-ylsulfanyl)-2-methyl-propionic acid ethyl ester.

$^1$H NMR (400 MHz, DMSO-d$_6$) (ppm) 7.39 (s, 1H) 7.16-7.22 (m, 2H) 7.06-7.14 (m, 2H) 3.92-4.03 (m, 1H) 3.60 (t, 4H) 2.99-3.08 (m, 2H) 2.53-2.63 (m, 3H) 2.31-2.43 (m, 1H) 1.67-1.78 (m, 8H) 1.53-1.63 (m, 4H) 1.39 (s, 6H) 1.02-1.12 (m, 2H) 0.87 (d, 3H)

HPLC-MS: m/z=502 (M+1)

Example 18

{2-[3-(2-Indan-2-yl-ethyl)-3-(trans-4-methyl-cyclohexyl)-ureido]-thiazol-5-ylsulfanyl}-acetic acid

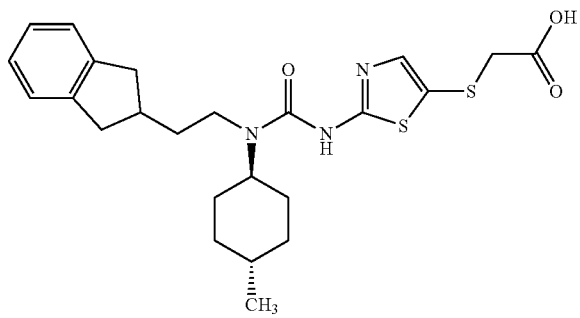 [SMILES: C[C@H]1CC[C@H](N(CCC2Cc3ccccc3C2)C(=O)Nc2ncc(SCC(=O)O)s2)CC1]

The compound was prepared following an analogous procedure to the one described for the synthesis of 2-methyl-2-{2-[3-(trans-4-methyl-cyclohexyl)-3-(4-phenyl-butyl)-ureido]-thiazol-5-ylsulfanyl}-propionic acid using 2-indan-2-yl-ethanol and (2-aminothiazol-5-ylsulfanyl)acetic acid ethyl ester $^1$H NMR (400 MHz, DMSO-d$_6$) (ppm) 7.33-7.41 (m, 1H) 7.10-7.18 (m, 2H) 7.02-7.09 (m, 2H) 3.86-3.99 (m, 1H) 3.52-3.59 (m, 3H) 3.40-3.48 (m, 3H) 2.87-3.06 (m, 2H) 2.56 (t, 2H) 2.29-2.41 (m, 1H) 1.61-1.74 (m, 6H) 1.49-1.58 (m, 3H) 1.22-1.36 (m, 1H) 0.94-1.10 (m, 2H) 0.83 (s, 3H)

HPLC-MS: m/z=474 (M+1)

Example 19

2,2-Dimethyl-3-{2-[3-(3-methyl-butyl)-3-(4-trans-methyl-cyclohexyl)-ureido]-thiazol-5-ylsulfanyl}-propionic acid

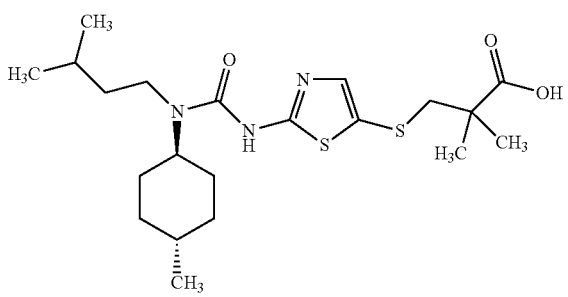 [SMILES: CC(C)CCN(C(=O)Nc1ncc(SCC(C)(C)C(=O)O)s1)[C@H]1CC[C@H](C)CC1]

4-trans-methyl-cyclohexylamine hydrochloride (15 g, 100 mmol) in THF-MeOH (2:1, 200 mL) was added solid NaOH (6.01 g, 150 mmol). The mixture was stirred for 30 m before isovaleraldehyde (10.4 g, 120 mmol), 20 mL AcOH was added. Subsequently sodium cyanoborohydride (6.0 g, 150 mmol) was added in small portions. The reaction mixture was stirred for 18 h before H$_2$O (200 mL) was added and the mixture was extracted with DCM (2×100 mL). The organic fraction were dried (MgSO$_4$) before an excess of HCl in diethyl ether were added. The solvent were removed in vacuo and diethyl ether was added (200 mL). The precipitate was filtered off washed with diethyl ether and dried in vacuo to give 18.8 g of (3-methyl-butyl)-(4-methyl-cyclohexyl)-amine.

The amine was coupled and the resulting ester hydrolyzed as previously described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 3-(2-amino-thiazol-5-ylsulfanyl)-2,2-dimethyl-propionic acid ethyl ester.

$^1$H NMR (400 MHz, DMSO-d$_6$) (ppm) 12.15 (br. s., 1H) 11.11 (br. s., 1H) 7.33 (s, 1H) 3.85-4.05 (m, 1H) 3.21 (t, 2H) 2.95 (s, 2H) 1.69 (d, 2H) 1.43-1.64 (m, 5H) 1.25-1.42 (m, 3H) 1.18 (s, 6H) 0.98-1.12 (m, 2H) 0.77-0.95 (m, 9H)

HPLC-MS: m/z=442 (m+1)

Example 20

3-{2-[3-(trans-4-Methyl-cyclohexyl)-3-(3-phenylsulfanyl-propyl)-ureido]-thiazol-5-ylsulfanyl}-propionic acid

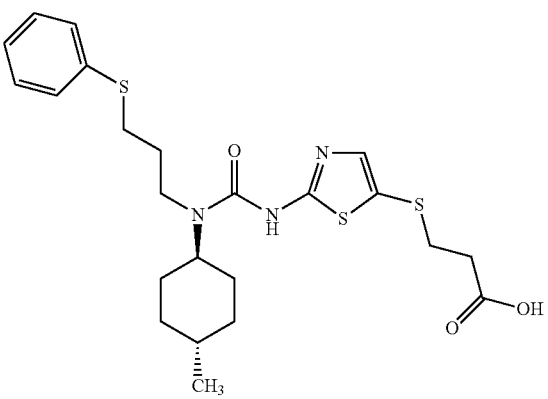 [SMILES: C[C@H]1CC[C@H](N(CCCSc2ccccc2)C(=O)Nc2ncc(SCCC(=O)O)s2)CC1]

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using thiophenol and 3-(2-amino-thiazol-5-ylsulfanyl)-propionic acid ethyl ester $^1$H NMR (400 MHz, CDCl$_3$) (ppm) 7.23-7.40 (m, 5H) 7.17 (t, 1H) 3.32 (t, 2H) 2.86-3.10 (m, 4H) 2.64-2.77 (m, 2H) 1.80-1.95 (m, 2H) 1.61-1.79 (m, 4H) 0.96-1.47 (m, 6H) 0.90 (d, 3H)

HPLC-MS: m/z: 494 (M+1)

Example 21

2,2-Dimethyl-3-{2-[3-(trans-4-methyl-cyclohexyl)-3-(t-phenyl-butyl)-ureido]-thiazol-5-ylsulfanyl}-propionic acid

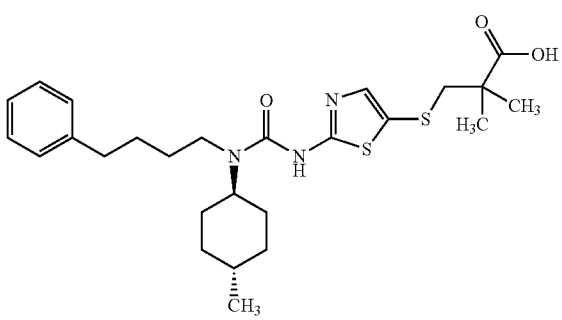 [SMILES: CC(C)(CSc1cnc(NC(=O)N(CCCCc2ccccc2)[C@H]2CC[C@H](C)CC2)s1)C(=O)O]

The compound was prepared following an analogous procedure to the one described for the synthesis of 2-methyl-2-{2-[3-(trans-4-methyl-cyclohexyl)-3-(4-phenyl-butyl)-ureido]-thiazol-5-ylsulfanyl}-propionic acid using 3-(2-amino-thiazol-5-ylsulfanyl)-2,2-dimethyl-propionic acid ethyl ester.

$^1$H NMR (400 MHz, DMSO-d$_6$) (ppm) 7.33 (s, 1H) 7.24-7.29 (m, 2H) 7.12-7.23 (m, 3H) 3.87-3.99 (m, 1H) 3.17-3.26 (m, 2H) 2.95 (s, 2H) 2.59 (t, 2H) 1.67 (d, 2H) 1.43-1.61 (m, 8H) 1.24-1.37 (m, 1H) 1.18 (s, 6H) 0.97-1.10 (m, 2H) 0.86 (d, 3H)

HPLC-MS: m/z=504 (M+1)

Example 22

{2-[3-[2-(4-Methoxy-phenyl)-ethyl]-3-(trans-4-methyl-cyclohexyl)-ureido]-thiazole-5-sulfanyl}-acetic acid

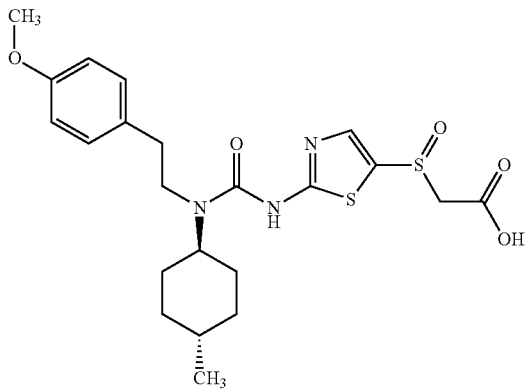 [SMILES: COc1ccc(CCN(C(=O)Nc2ncc(S(=O)CC(=O)O)s2)[C@H]2CC[C@H](C)CC2)cc1]

To Montmorinonite (415 mg) was added H$_2$O (98 µL) the mixture was stirred for 10 min before DCM (0.5 mL), oxone (428 mg, 0.70 mmol) and 2-{2-[3-[2-(4-methoxy-phenyl)-ethyl]-3-(trans-4-methyl-cyclohexyl)-ureido]-thiazol-5-ylsulfanyl}-2-methyl-propionic acid (129 mg, 0.278 mmol) suspended in DCM (2.6 mL) was added in seqence. The mixture was stirred at rt for 1.5 hs. LCMS showed a 1:1 mixture of the sulfoxide and sulfone. The reaction mixture was filtered, washed with DCM and the filtrate was concentrated in vacuo. The mixture was purified by HPLC to give 37 mg of {2-[3-[2-(4-methoxy-phenyl)-ethyl]-3-(trans-4-methyl-cyclohexyl)-ureido]-thiazole-5-sulfanyl}-acetic acid.

$^1$H NMR (400 MHz, DMSO-d$_6$) (ppm) 7.91 (s, 1H) 7.20 (d, 2H) 6.87 (d, 2H) 4.16 (dd, 2H) 3.93-4.06 (m, 1H) 3.72 (s, 3H) 3.31-3.48 (m, 2H) 2.74 (t, 2H) 1.70 (d, 2H) 1.48-1.64 (m, 4H) 1.25-1.43 (m, 1H) 0.97-1.16 (m, 2H) 0.87 (d, 3H)

HPLC-MS: m/z=480 (M+1)

Example 23

{2-[3-(2-Benzyloxy-ethyl)-3-(trans-4-methyl-cyclohexyl)-ureido]-thiazole-5-sulfanyl}-acetic acid

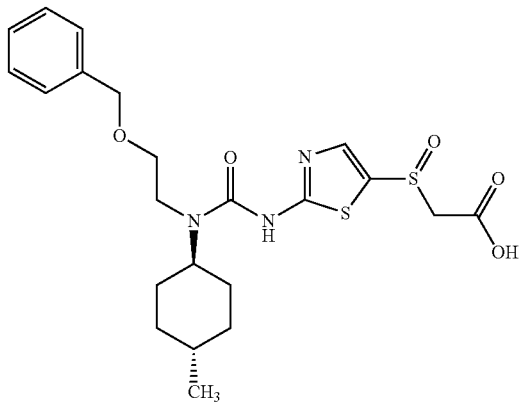 [SMILES: C[C@H]1CC[C@H](N(CCOCc2ccccc2)C(=O)Nc2ncc(S(=O)CC(=O)O)s2)CC1]

The compound was prepared as previously described for {2-[3-[2-(4-methoxy-phenyl)-ethyl]-3-(trans-4-methyl-cyclohexyl)-ureido]-thiazole-5-sulfanyl}-acetic acid using {2-[3-(2-benzyloxy-ethyl)-3-(4-methyl-cyclohexyl)-ureido]-thiazol-5-ylsulfanyl}-acetic acid.

$^1$H NMR (300 MHz, CDCl$_3$) (ppm) 7.71 (s, 1H) 7.14-7.42 (m, 5H) 4.59 (s, 2H) 3.84-4.30 (m, 3H) 3.38-3.69 (m, 4H) 1.59-1.86 (m, 4H) 0.99-1.57 (m, 5H) 0.89 (d, 3H)

Example 24

2-{2-[3-[2-(4-Fluoro-2-trifluoromethyl-benzyloxy)-ethyl]-3-(trans-4-methyl-cyclohexyl)-ureido]-thiazol-5-ylsulfanyl}-2-methyl-propionic acid

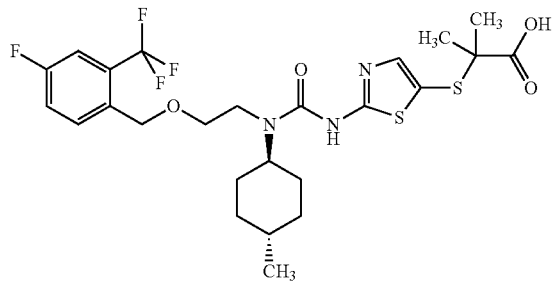 [SMILES: CC(C)(Sc1cnc(NC(=O)N(CCOCc2ccc(F)cc2C(F)(F)F)[C@H]2CC[C@H](C)CC2)s1)C(=O)O]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-bromomethyl-4-fluoro-2-trifluoromethyl-benzene and 2-(2-amino-thiazol-5-ylsulfanyl)-2-methyl-propionic acid ethyl ester.

$^1$H NMR (300 MHz, DMSO-d$_6$) (ppm) 7.65-7.74 (m, 1H) 7.53-7.60 (m, 1H) 7.41-7.51 (m, 1H) 7.33 (s, 1H) 4.61 (s, 2H) 3.80-3.98 (m, 1H) 3.53-3.59 (m, 2H) 3.45-3.52 (m, 2H) 1.59-1.68 (m, 2H) 1.42-1.58 (m, 4H) 1.36 (s, 6H) 1.22-1.30 (m, 1H) 1.17-1.21 (m, 1H) 0.91-1.07 (m, 2H) 0.82 (d, 3H)

HPLC-MS: m/z=578 (M+1)

Example 25

2-{2-[3-[2-(2-Chloro-4-fluoro-benzyloxy)-ethyl]-3-(trans-4-methyl-cyclohexyl)-ureido]-thiazol-5-ylsulfanyl}-2-methyl-propionic acid

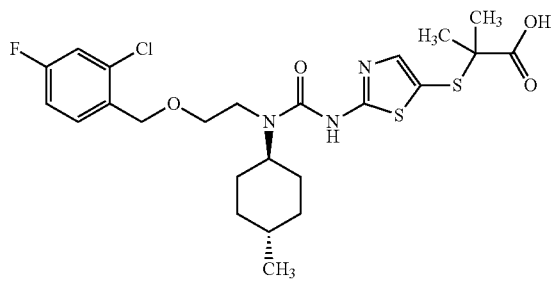 [SMILES: CC(C)(Sc1cnc(NC(=O)N(CCOCc2ccc(F)cc2Cl)[C@H]2CC[C@H](C)CC2)s1)C(=O)O]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-bromomethyl-2-chloro-4-fluoro-benzene and 2-(2-amino-thiazol-5-ylsulfanyl)-2-methyl-propionic acid ethyl ester.

$^1$H NMR (300 MHz, DMSO-$d_6$) (ppm) 7.50-7.59 (m, 1H) 7.42 (dd, 1H) 7.37 (s, 1H) 7.12-7.25 (m, 1H) 4.57 (s, 2H) 3.85-4.03 (m, 1H) 3.56-3.63 (m, 2H) 3.47-3.55 (m, 2H) 1.63-1.73 (m, 2H) 1.46-1.62 (m, 4H) 1.39 (s, 6H) 0.96-1.10 (m, 2H) 0.86 (d, 3H)

HPLC-MS: m/z=544 (M+1)

Example 26

2-Methyl-2-(2-{3-(trans-4-methyl-cyclohexyl)-3-[2-(2-trifluoromethyl-benzyloxy)-ethyl]-ureido}-thiazol-5-ylsulfanyl)-propionic acid

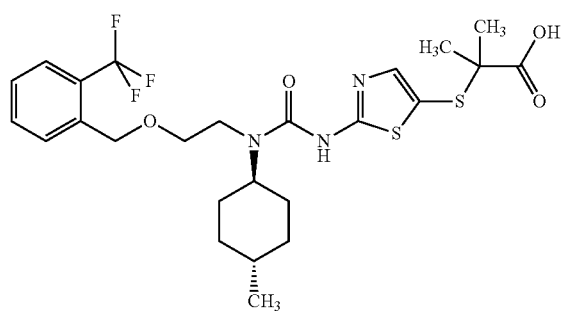 [SMILES: CC(C)(Sc1cnc(NC(=O)N(CCOCc2ccccc2C(F)(F)F)[C@H]2CC[C@H](C)CC2)s1)C(=O)O]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-bromomethyl-2-trifluoromethyl-benzene and 2-(2-amino-thiazol-5-ylsulfanyl)-2-methyl-propionic acid ethyl ester.

$^1$H NMR (300 MHz, DMSO-$d_6$) (ppm) 7.63-7.71 (m, 2H) 7.59 (t, 1H) 7.45 (t, 1H) 7.32 (s, 1H) 4.65 (s, 2H) 3.78-3.98 (m, 1H) 3.52-3.61 (m, 3H) 1.59-1.70 (m, 2H) 1.44-1.59 (m, 4H) 1.35 (s, 6H) 1.21-1.30 (m, 1H) 1.19 (s, 1H) 0.91-1.08 (m, 2H) 0.82 (d, 3H)

HPLC-MS: m/z=560 (M+1)

Example 27

2-{2-[3-[2-(2,4-Difluoro-benzyloxy)-ethyl]-3-(trans-4-methyl-cyclohexyl)-ureido]-thiazol-5-ylsulfanyl}-2-methyl-propionic acid

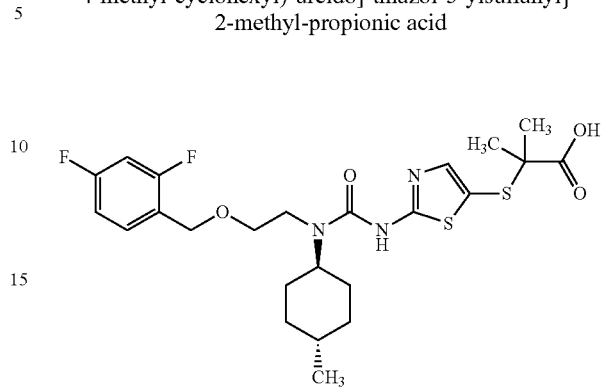

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-bromomethyl-2,4-difluoro-benzene and 2-(2-amino-thiazol-5-ylsulfanyl)-2-methyl-propionic acid ethyl ester.

$^1$H NMR (300 MHz, DMSO-$d_6$) (ppm) 7.39-7.52 (m, 1H) 7.33 (s, 1H) 7.10-7.23 (m, 1H) 6.92-7.07 (m, 1H) 4.50 (s, 2H) 3.77-3.94 (m, 1H) 1.58-1.68 (m, 2H) 1.43-1.57 (m, 4H) 1.35 (s, 6H) 1.22-1.31 (m, 1H) 0.90-1.07 (m, 2H) 0.82 (d, 3H)

HPLC-MS: m/z=528 (M+1)

Example 28

2-Methyl-2-{2-[3-[2-(2-methyl-benzyloxy)-ethyl]-3-(trans-4-methyl-cyclohexyl)-ureido]-thiazol-5-ylsulfanyl}-propionic acid

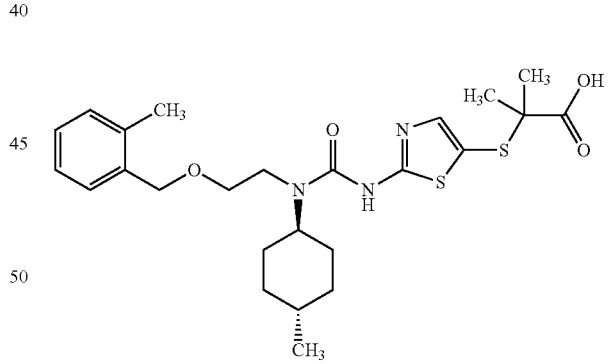

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-bromomethyl-2-methyl-benzene and 2-(2-amino-thiazol-5-ylsulfanyl)-2-methyl-propionic acid ethyl ester.

$^1$H NMR (400 MHz, DMSO-$d_6$) (ppm) 7.37 (s, 1H) 7.31 (d, 1H) 7.10-7.20 (m, 3H) 4.52 (s, 2H) 3.85-4.00 (m, 1H) 3.46-3.57 (m, 4H) 2.25 (s, 3H) 1.63-1.71 (m, 2H) 1.46-1.62 (m, 4H) 1.39 (s, 6H) 1.25-1.34 (m, 1H) 1.03 (q, 2H) 0.86 (d, 3H)

HPLC-MS: m/z=506 (M+1)

Example 29

3-{2-[3-[2-(4-Fluoro-2-trifluoromethyl-benzyloxy)-ethyl]-3-(trans-4-methyl-cyclohexyl)-ureido]-thiazol-5-ylsulfanyl}-2,2-dimethyl-propionic acid

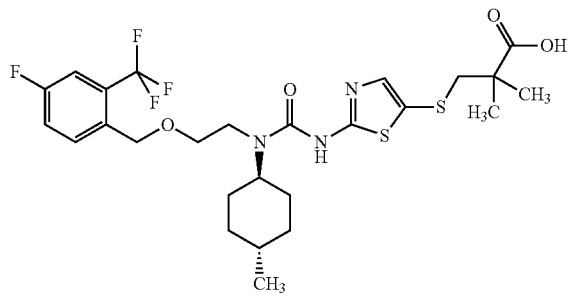 [SMILES: CC(C)(CSc1cnc(NC(=O)N(CCOCc2ccc(F)cc2C(F)(F)F)[C@H]2CC[C@H](C)CC2)s1)C(=O)O]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-bromomethyl-4-fluoro-2-trifluoromethyl-benzene and 3-(2-amino-thiazol-5-ylsulfanyl)-2,2-dimethyl-propionic acid ethyl ester.

$^1$H NMR (400 MHz, DMSO-$d_6$) (ppm) 7.74 (dd, 1H) 7.61 (dd, 1H) 7.46-7.54 (m, 1H) 7.32 (s, 1H) 4.65 (s, 2H) 3.88-3.99 (m, 1H) 3.59 (t, 2H) 3.47-3.53 (m, 2H) 2.95 (s, 2H) 1.63-1.72 (m, 2H) 1.47-1.62 (m, 4H) 1.26-1.35 (m, 1H) 1.18 (s, 6H) 0.97-1.09 (m, 2H) 0.86 (d, 3H)

HPLC-MS: m/z=592 (M+1)

Example 30

3-{2-[3-[2-(2-Chloro-4-fluoro-benzyloxy)-ethyl]-3-(trans-4-methyl-cyclohexyl)-ureido]-thiazol-5-ylsulfanyl}-2,2-dimethyl-propionic acid

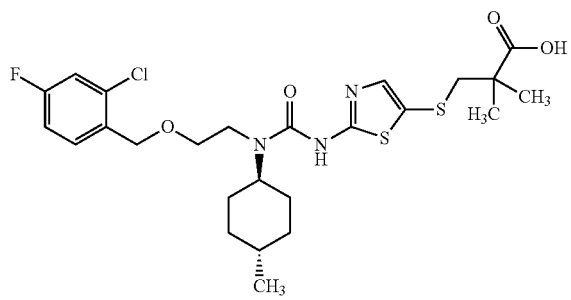 [SMILES: CC(C)(CSc1cnc(NC(=O)N(CCOCc2ccc(F)cc2Cl)[C@H]2CC[C@H](C)CC2)s1)C(=O)O]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-bromomethyl-2-chloro-4-fluoro-benzene and 3-(2-amino-thiazol-5-ylsulfanyl)-2,2-dimethyl-propionic acid ethyl ester.

$^1$H NMR (400 MHz, DMSO-$d_6$) (ppm) 7.55 (dd, 1H) 7.43 (dd, 1H) 7.32 (s, 1H) 7.14-7.22 (m, 1H) 4.57 (s, 2H) 3.57-3.62 (m, 3H) 3.46-3.53 (m, 2H) 2.95 (s, 2H) 1.73-1.81 (m, 1H) 1.64-1.72 (m, 2H) 1.47-1.61 (m, 4H) 1.27-1.37 (m, 1H) 1.18 (s, 6H) 0.96-1.09 (m, 2H) 0.86 (d, 3H)

HPLC-MS: m/z=558 (M+1)

Example 31

2-Methyl-2-{2-[3-(trans-4-methyl-cyclohexyl)-3-phenethyl-ureido]-thiazol-5-ylsulfanyl}-propionic acid

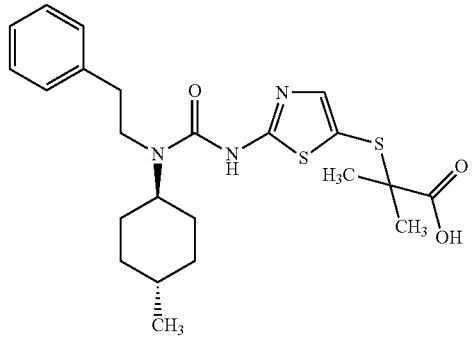 [SMILES: CC(C)(Sc1cnc(NC(=O)N(CCc2ccccc2)[C@H]2CC[C@H](C)CC2)s1)C(=O)O]

A refluxing solution of 4-trans-methyl-cyclohexylamine hydrochloride (2.64 g, 17.7 mmol) and potassium carbonate (4.87 g, 35.3) in acetonitrile (20 mL) was added a solution of 2-phenylethylbromide (3.27 g, 17.7 mmol) and the reaction mixture was refluxed for 18 h.

The volatiles were removed in vacuo and the residue was separated between diethyl ether (100 mL) and $H_2O$ (100 mL). The aqueous phase was extracted with an additional 100 mL diethyl ether and the combined organic phases were dried ($Na_2SO_4$), filtered and concentrated in vacuo to give the crude secondary amine. Purification on preparative HPLC gave 3.2 g the TFA salt of (trans-4-methyl-cyclohexyl)-phenethyl-amine.

(trans-4-Methyl-cyclohexyl)-phenethyl-amine was transformed to 2-methyl-2-{2-[3-(trans-4-methyl-cyclohexyl)-3-phenethyl-ureido]-thiazol-5-ylsulfanyl}-propionic acid using the procedure described for the synthesis of 2-{2-[3-[2-(2-chloro-benzyloxy)-ethyl]-3-(trans-4-methyl-cyclohexyl)-ureido]-thiazol-5-ylsulfanyl}-2,2-dimethyl-propionic acid.

$^1$H NMR (400 MHz, DMSO-$d_6$) (ppm) 7.41 (s, 1H) 7.23-7.36 (m, 3H) 7.15-7.24 (m, 1H) 3.88-4.10 (m, 1H) 3.32-3.50 (m, 2H) 2.79 (t, 2H) 1.63-1.75 (m, 2H) 1.48-1.64 (m, 4H) 1.26-1.46 (m, 8H) 0.98-1.15 (m, 2H) 0.87 (d, 3H)

HPLC-MS: m/z=462 (M+1)

Example 32

2,2-Dimethyl-3-{2-[3-(trans-4-methyl-cyclohexyl)-3-phenethyl-ureido]-thiazol-5-ylsulfanyl}-propionic acid

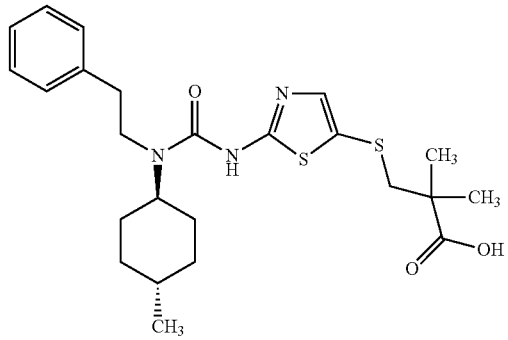 [SMILES: CC(C)(CSc1cnc(NC(=O)N(CCc2ccccc2)[C@H]2CC[C@H](C)CC2)s1)C(=O)O]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 3-(2-amino-thiazol-5-ylsulfanyl)-2,2-dimethyl-propionic acid ethyl ester.

$^1$H NMR (400 MHz, DMSO-$d_6$) (ppm) 7.35 (s, 1H) 7.24-7.34 (m, 5H) 7.16-7.25 (m, 1H) 3.35-3.49 (m, 2H) 2.97 (s, 2H) 2.78 (t, 2H) 1.63-1.74 (m, 2H) 1.46-1.63 (m, 4H) 1.26-1.40 (m, 1H) 1.19 (s, 6H) 0.97-1.13 (m, 2H) 0.87 (d, 3H)

HPLC-MS: m/z=476 (M+1)

Example 33

3-{2-[3-[2-(2-Fluoro-benzyloxy)-ethyl]-3-(trans-4-methyl-cyclohexyl)-ureido]-thiazol-5-ylsulfanyl}-2,2-dimethyl-propionic acid

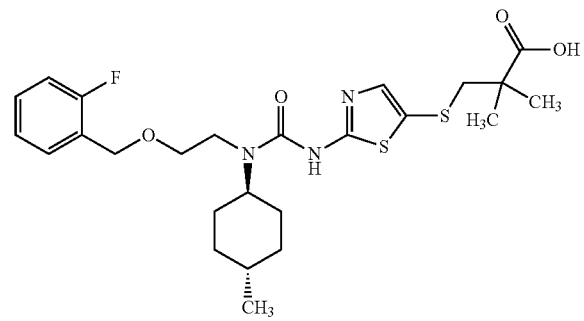 [SMILES: CC(C)(CSc1cnc(NC(=O)N(CCOCc2ccccc2F)[C@H]2CC[C@H](C)CC2)s1)C(=O)O]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-bromomethyl-2-fluoro-benzene and 3-(2-amino-thiazol-5-ylsulfanyl)-2,2-dimethyl-propionic acid ethyl ester.

$^1$H NMR (400 MHz, DMSO-$d_6$) (ppm) 7.45 (t, 1H) 7.31-7.38 (m, 2H) 7.14-7.20 (m, 2H) 4.58 (s, 2H) 3.85-3.97 (m, 1H) 3.56 (t, 2H) 3.40-3.50 (m, 3H) 2.95 (s, 2H) 1.63-1.71 (m, 2H) 1.46-1.59 (m, 4H) 1.25-1.36 (m, 1H) 1.18 (s, 6H) 0.96-1.08 (m, 2H) 0.86 (d, 3H)

HPLC-MS: m/z=524 (M+1)

Example 34

3-{2-[3-[2-(2,4-Difluoro-benzyloxy)-ethyl]-3-(trans-4-methyl-cyclohexyl)-ureido]-thiazol-5-ylsulfanyl}-2,2-dimethyl-propionic acid

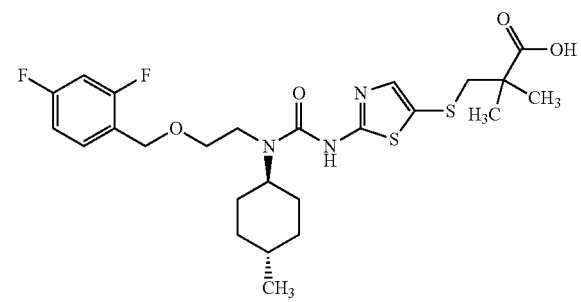 [SMILES: CC(C)(CSc1cnc(NC(=O)N(CCOCc2ccc(F)cc2F)[C@H]2CC[C@H](C)CC2)s1)C(=O)O]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-bromomethyl-2,4-difluoro-benzene and 3-(2-amino-thiazol-5-ylsulfanyl)-2,2-dimethyl-propionic acid ethyl ester.

$^1$H NMR (400 MHz, DMSO-$d_6$) (ppm) 7.44-7.56 (m, 1H) 7.32 (s, 1H) 7.22 (t, 1H) 7.05 (t, 1H) 4.54 (s, 2H) 3.84-4.01 (m, 1H) 3.51-3.57 (m, 2H) 3.43-3.49 (m, 2H) 2.95 (s, 2H) 1.63-1.71 (m, 2H) 1.44-1.60 (m, 4H) 1.26-1.37 (m, 1H) 1.18 (s, 6H) 0.96-1.08 (m, 2H) 0.86 (d, 3H)

HPLC-MS: m/z=542 (M+1)

Example 35

2,2-Dimethyl-3-{2-[3-[2-(2-methyl-benzyloxy)-ethyl]-3-(trans-4-methyl-cyclohexyl)-ureido]-thiazol-5-ylsulfanyl}-propionic acid

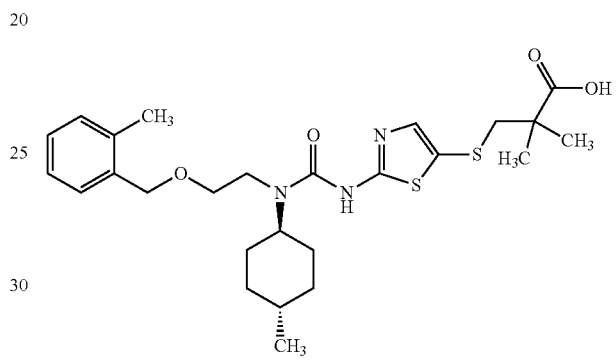

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-bromomethyl-2-methyl-benzene and 3-(2-amino-thiazol-5-ylsulfanyl)-2,2-dimethyl-propionic acid ethyl ester.

$^1$H NMR (400 MHz, DMSO-$d_6$) (ppm) 7.28-7.35 (m, 2H) 7.10-7.20 (m, 3H) 4.52 (s, 2H) 3.51-3.56 (m, 2H) 3.46-3.51 (m, 2H) 2.95 (s, 2H) 2.25 (s, 3H) 1.67 (d, 2H) 1.46-1.61 (m, 4H) 1.25-1.40 (m, 1H) 1.18 (s, 6H) 1.02 (q, 2H) 0.86 (d, 3H)

HPLC-MS: m/z=520 (M+1)

Example 36

2-Methyl-2-(2-{3-(trans-4-methyl-cyclohexyl)-3-[2-(4-trifluoromethoxy-phenyl)-ethyl]-ureido}-thiazol-5-ylsulfanyl)-propionic acid

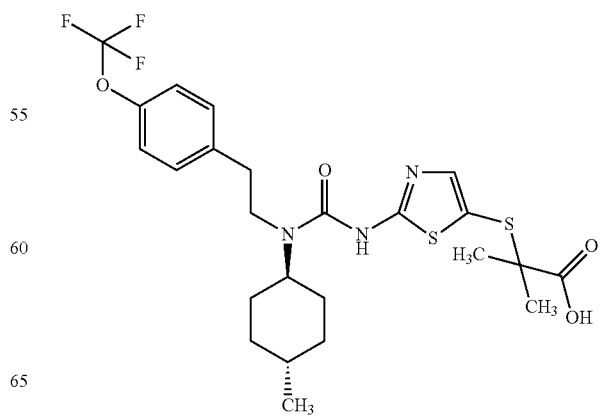

A mixture of 2-(4-trifluoromethoxy-phenyl)-ethanol (383 mg, 1.86 mmol), cyanomethyl-trimethyl-phosphoniumiodide (J. Org. Chem. 2001, 66, 7, 2518-2521) (500 mg, 2.1 mmol) and DIPEA (0.76 mL, 4.34 mmol) in propionitrile (4 mL) was heated to 90° C. for 18 hs, then stirred for 48 hs at rt, before the reaction mixture was poured in to a solution of 2 g $K_2CO_3$ in $H_2O$ (30 mL). The mixture was extracted with DCM (3×30 mL) and the combined organic phases were dried ($MgSO_4$) and filtered and the solvent was removed in vacuo. The residue was purified using preparative HPLC tog give 238 mg of (4-methyl-cyclohexyl)-[2-(4-trifluoromethoxy-phenyl)-ethyl]-amine.

The amine was coupled and the resulting ester hydrolyzed as previously described for 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 2-(2-amino-thiazol-5-ylsulfanyl)-2-methyl-propionic acid ethyl ester $^1$H NMR (400 MHz, DMSO-$d_6$) (ppm) 7.38-7.45 (m, 3H) 7.30 (d, 2H) 3.93-4.03 (m, 1H) 2.83 (t, 2H) 1.63-1.73 (m, 2H) 1.46-1.61 (m, 4H) 1.25-1.45 (m, 7H) 0.98-1.12 (m, 2H) 0.86 (d, 3H) 1.40 (m, 1H) 1.19 (s, 6H) 0.97-1.13 (m, 2H) 0.87 (d, 3H)

HPLC-MS: m/z=546 (M+1)

Example 37

2-{2-[3-[2-(4-Chloro-phenyl)-ethyl]-3-(trans-4-methyl-cyclohexyl)-ureido]-thiazol-5-ylsulfanyl}-2-methyl-propionic acid

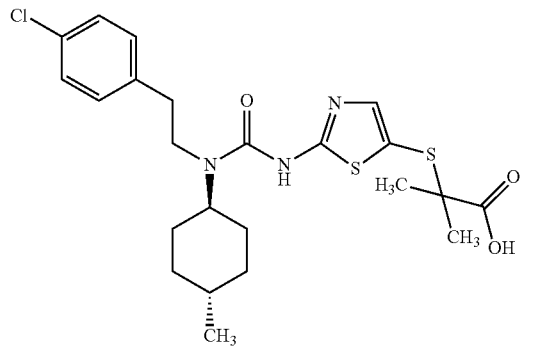 [SMILES: CC(C)(Sc1cnc(NC(=O)N(CCc2ccc(Cl)cc2)[C@H]2CC[C@H](C)CC2)s1)C(=O)O]

The compound was prepared following an analogous procedure to the one described for the synthesis of 2-Methyl-2-{2-[3-(trans-4-methyl-cyclohexyl)-3-phenethyl-ureido]-thiazol-5-ylsulfanyl}-propionic acid using 1-chloro-4-(2-iodo-ethyl)-benzene (J. Med. Chem. 1998, 41, 3, 358-378) and 2-(2-amino-thiazol-5-ylsulfanyl)-2-methyl-propionic acid ethyl ester.

$^1$H NMR (400 MHz, CDCl$_3$) (ppm) 7.15-7.34 (m, 4H) 7.06 (s, 1H) 3.73-4.37 (m, 1H) 3.35-3.63 (m, 2H) 2.78-3.01 (m, 2H) 1.81 (t, 4H) 1.45-1.69 (m, 8H) 1.06-1.43 (m, 3H) 0.91 (d, 3H)

Example 38

2-Methyl-2-{2-[3-(trans-4-methyl-cyclohexyl)-3-(3-phenyl-propyl)-ureido]-thiazol-5-ylsulfanyl}-propionic acid

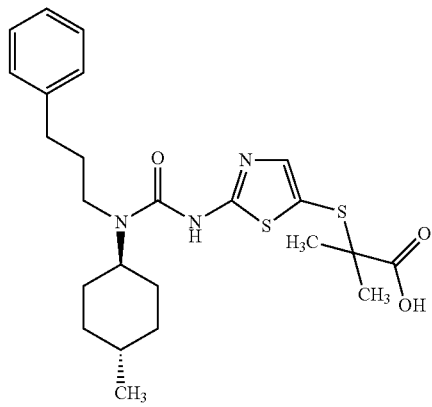 [SMILES: CC(C)(Sc1cnc(NC(=O)N(CCCc2ccccc2)[C@H]2CC[C@H](C)CC2)s1)C(=O)O]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 1-bromo-3-phenylpropane and 2-(2-amino-thiazol-5-ylsulfanyl)-2-methyl-propionic acid ethyl ester.

$^1$H NMR (400 MHz, CDCl$_3$) (ppm) 7.14-7.34 (m, 5H) 7.05 (s, 1H) 3.70-4.33 (m, 1H) 3.17-3.47 (m, 2H) 2.58-2.78 (m, 2H) 1.86-2.04 (m, 2H) 1.66-1.84 (m, 4H) 1.61 (s, 6H) 1.34-1.53 (m, 2H) 1.00-1.34 (m, 3H) 0.88 (d, 3H)

HPLC-MS: m/z=477 (M+1)

Example 39

2,2-Dimethyl-3-(2-{3-(trans-4-methyl-cyclohexyl)-3-[2-(2-trifluoromethyl-benzyloxy)-ethyl]-ureido}-thiazol-5-ylsulfanyl)-propionic acid

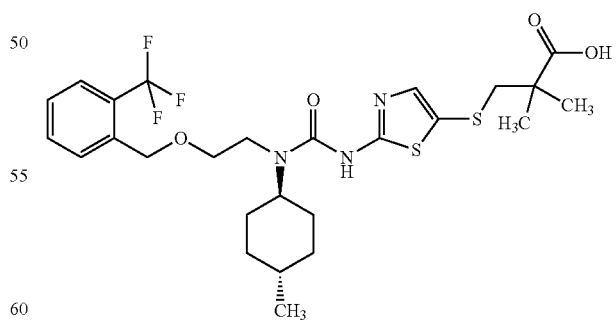

The compound was prepared following an analogous procedure to the one described for the synthesis of 3-{2-[3-[2-(2-Chloro-benzyloxy)-ethyl]-3-(trans-4-methyl-cyclohexyl)-ureido]-thiazol-5-ylsulfanyl}-2,2-dimethylpropionic acid using 3-(2-amino-thiazol-5-ylsulfanyl)-2,2-dimethyl-propionic acid ethyl ester and 2-trifluoromethylbenzyl bromide.

¹H NMR (400 MHz, DMSO-d₆) (ppm) 7.67-7.74 (m, 2H) 7.71 (d, 2H) 7.63 (t, 1H) 7.49 (t, 1H) 7.33 (s, 1H) 4.68 (s, 2H) 3.85-4.02 (m, 1H) 3.57-3.61 (m, 2H) 2.95 (s, 2H) 1.62-1.71 (m, 2H) 1.47-1.62 (m, 4H) 1.22-1.37 (m, 2H) 1.18 (s, 6H) 0.97-1.09 (m, 2H) 0.86 (d, 3H)

HPLC-MS: m/z=574 (M+1)

Example 40

2-{2-[3-[2-(2-Difluoromethoxy-benzyloxy)-ethyl]-3-(trans-4-methyl-cyclohexyl)-ureido]-thiazol-5-ylsulfanyl}-2-methyl-propionic acid

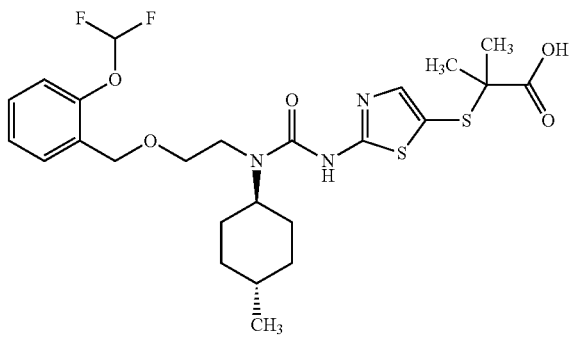 [SMILES: CC(C)(Sc1cnc(NC(=O)N(CCOCc2ccccc2OC(F)F)[C@H]2CC[C@H](C)CC2)s1)C(=O)O]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 2-(2-amino-thiazol-5-ylsulfanyl)-2-methyl-propionic acid ethyl ester and 2-difluoromethyl-benzylbromide.

¹H NMR (400 MHz, DMSO-d₆) (ppm) 7.49 (d, 1H) 7.31-7.42 (m, 2H) 7.15-7.26 (m, 2H) 4.56 (s, 2H) 3.84-4.07 (m, 1H) 3.54-3.63 (m, 3H) 3.45-3.54 (m, 2H) 1.73-1.81 (m, 1H) 1.63-1.72 (m, 2H) 1.48-1.63 (m, 4H) 1.39 (s, 6H) 1.23-1.36 (m, 2H) 0.95-1.10 (m, 2H) 0.86 (d, 6H)

HPLC-MS: m/z=559 (M+1)

Example 41

2-{2-[3-[2-(3-Fluoro-4-methoxy-phenyl)-ethyl]-3-(trans-4-methyl-cyclohexyl)-ureido]-thiazol-5-ylsulfanyl}-2-methyl-propionic acid

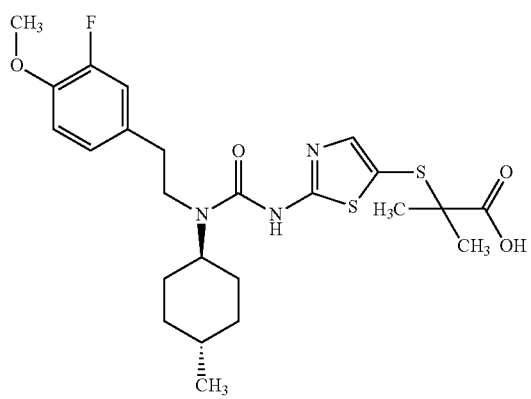 [SMILES: COc1ccc(CCN(C(=O)Nc2ncc(SC(C)(C)C(=O)O)s2)[C@H]2CC[C@H](C)CC2)cc1F]

A mixture of resin bound triphenyl phosphine (polystyrene 2% cross linking, loading=3 mmol/g, 3 g, 9 mmol) and imidazole (0.48 g, 7.1 mmol) in DCM (30 mL) cooled on an ice bath was drop wise added Br₂ (1.13 g, 7.1 mmol), whereupon a solution of 4-(2-hydroxy-ethyl)-2-fluoro-1-methoxy-benzene (1.0 g, 5.88 mmol) in DCM (5 mL) was added. The cooling bath was removed and the reaction mixture was stirred for 16 hs before the resin was filtered off. The resin was washed with DCM and the filtrate was concentrated in vacuo. The residue was purified using column chromatography (SiO₂, heptane-EtAOc 95:5) to give 0.82 g of 4-(2-bromo-ethyl)-2-fluoro-1-methoxy-benzene The bromide was reacted with the amine, coupled and hydrolysed following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 2-(2-amino-thiazol-5-ylsulfanyl)-2-methyl-propionic acid ethyl ester.

¹H NMR (400 MHz, CDCl₃) (ppm) 6.94-7.07 (m, 3H) 6.83-6.92 (m, 1H) 3.87 (s, 3H) 3.40-3.57 (m, 2H) 2.82-2.91 (m, 2H) 1.73-1.90 (m, 4H) 1.46-1.68 (m, 8H) 1.08-1.42 (m, 3H) 0.91 (d, 3H)

HPLC-MS: m/z=510 (M+1)

Example 42

2-{2-[3-[2-(3-Chloro-5-fluoro-phenyl)-ethyl]-3-(trans-4-methyl-cyclohexyl)-ureido]-thiazol-5-ylsulfanyl}-2-methyl-propionic acid

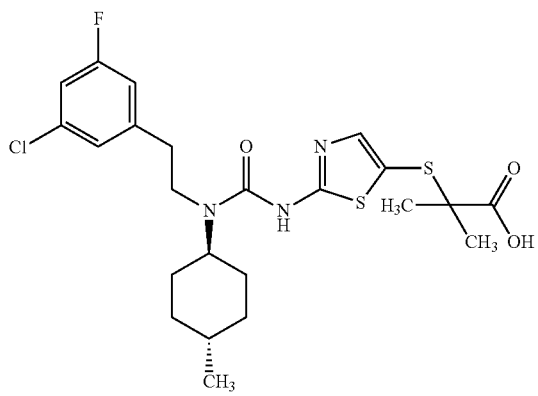 [SMILES: CC(C)(Sc1cnc(NC(=O)N(CCc2cc(F)cc(Cl)c2)[C@H]2CC[C@H](C)CC2)s1)C(=O)O]

The compound was prepared following an analogous procedure to the one described for the synthesis of 2-{2-[3-[2-(3-fluoro-4-methoxy-phenyl)-ethyl]-3-(trans-4-methyl-cyclohexyl)-ureido]-thiazol-5-ylsulfanyl}-2-methyl-propionic acid using 1-(2-hydroxy-ethyl)-3-chloro-5-fluoro-benzene and 2-(2-amino-thiazol-5-ylsulfanyl)-2-methyl-propionic acid ethyl ester.

¹H NMR (400 MHz, DMSO-d₆) (ppm) 7.41 (s, 1H) 7.23-7.31 (m, 2H) 7.20 (d, 1H) 3.91-4.06 (m, 1H) 3.40-3.51 (m, 2H) 2.81 (t, 2H) 1.69 (d, 2H) 1.51-1.64 (m, 4H) 1.29-1.46 (m, 7H) 0.98-1.13 (m, 2H) 0.87 (d, 3H)

HPLC-MS: m/z=514 (M+1)

Example 43

2-Methyl-2-(2-{3-(trans-4-methyl-cyclohexyl)-3-[3-(3-trifluoromethyl-phenylsulfanyl)-propyl]-ureido}-thiazol-5-ylsulfanyl)-propionic acid

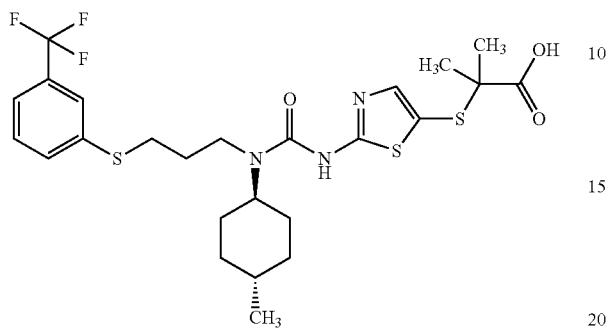

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 2-(2-amino-thiazol-5-ylsulfanyl)-2-methyl-propionic acid ethyl ester and 3-trifluoromethyl thiophenol.

$^1$H NMR (400 MHz, DMSO-$d_6$) (ppm) 7.64-7.68 (m, 1H) 7.63 (br. s., 1H) 7.51-7.58 (m, 2H) 7.40 (s, 1H) 3.87-4.01 (m, 1H) 3.10 (t, 2H) 1.73-1.82 (m, 2H) 1.59-1.67 (m, 2H) 1.47-1.55 (m, 2H) 1.40-1.47 (m, 2H) 1.39 (s, 6H) 1.21-1.31 (m, 1H) 0.95-1.07 (m, 2H) 0.86 (d, 3H)

HPLC-MS: m/z=576 (M+1)

Example 44

2-{2-[3-[3-(2-Chloro-phenylsulfanyl)-propyl]-3-(trans-4-methyl-cyclohexyl)-ureido]-thiazol-5-ylsulfanyl}-2-methyl-propionic acid

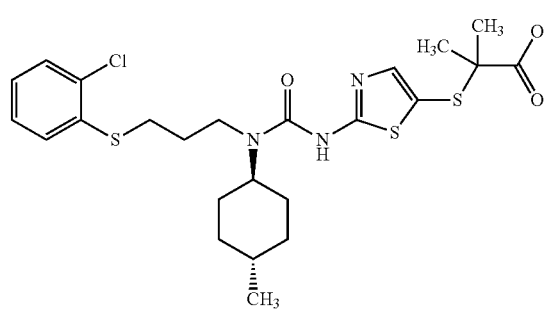

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 2-(2-amino-thiazol-5-ylsulfanyl)-2-methyl-propionic acid ethyl ester and 2-chloro-thiophenol.

$^1$H NMR (400 MHz, DMSO-$d_6$) (ppm) 7.42-7.47 (m, 2H) 7.41 (s, 1H) 7.29-7.36 (m, 1H) 7.15-7.23 (m, 1H) 3.88-4.02 (m, 1H) 3.05 (t, 2H) 1.76-1.84 (m, 2H) 1.62-1.69 (m, 2H) 1.49-1.55 (m, 2H) 1.40-1.49 (m, 2H) 0.96-1.08 (m, 2H) 0.86 (d, 3H)

HPLC-MS: m/z: 542 (M+1)

Example 45

2-{2-[3-[2-(3,5-Difluoro-phenyl)-ethyl]-3-(trans-4-methyl-cyclohexyl)-ureido]-thiazol-5-ylsulfanyl}-2-methyl-propionic acid

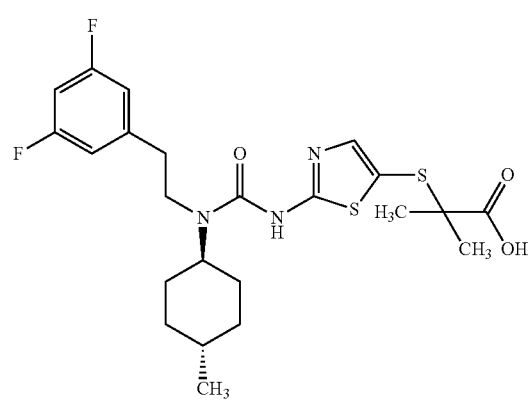 [SMILES: CC(C)(Sc1cnc(NC(=O)N(CCc2cc(F)cc(F)c2)[C@H]2CC[C@H](C)CC2)s1)C(=O)O]

The compound was prepared following an analogous procedure to the one described for the synthesis of 2-{2-[3-[2-(3-fluoro-4-methoxy-phenyl)-ethyl]-3-(trans-4-methyl-cyclohexyl)-ureido]-thiazol-5-ylsulfanyl}-2-methyl-propionic acid using 1-(2-hydroxy-ethyl)-3,5-difluoro-benzene and 2-(2-amino-thiazol-5-ylsulfanyl)-2-methyl-propionic acid ethyl ester.

$^1$H NMR (400 MHz, DMSO-$d_6$) (ppm) 7.41 (s, 1H) 6.99-7.13 (m, 3H) 3.90-4.08 (m, 1H) 3.39-3.52 (m, 2H) 2.82 (t, 2H) 1.63-1.76 (m, 2H) 1.52-1.64 (m, 4H) 1.26-1.48 (m, 7H) 0.96-1.15 (m, 2H) 0.87 (d, 3H)

HPLC-MS: m/z=498 (M+1)

Example 46

2-Methyl-2-{2-[3-(trans-4-methyl-cyclohexyl)-3-(2-p-tolyl-ethyl)-ureido]-thiazol-5-ylsulfanyl}-propionic acid

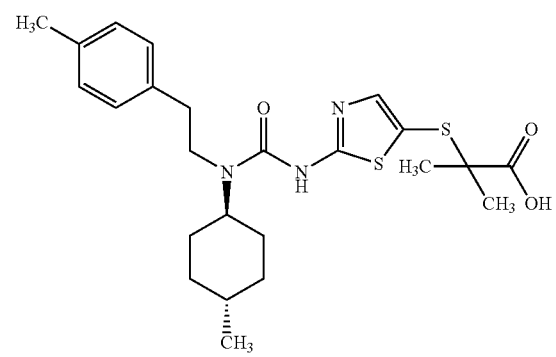 [SMILES: Cc1ccc(CCN(C(=O)Nc2ncc(SC(C)(C)C(=O)O)s2)[C@H]2CC[C@H](C)CC2)cc1]

The compound was prepared following an analogous procedure to the one described for the synthesis of 2-{2-[3-[2-(3-fluoro-4-methoxy-phenyl)-ethyl]-3-(trans-4-methyl-cyclohexyl)-ureido]-thiazol-5-ylsulfanyl}-2-methyl-propionic acid using 1-(2-hydroxy-ethyl)-4-methyl-benzene and 2-(2-amino-thiazol-5-ylsulfanyl)-2-methyl-propionic acid ethyl ester.

¹H NMR (400 MHz, DMSO-d₆) (ppm) 7.41 (s, 1H) 7.17 (d, 2H) 7.11 (d, 2H) 3.91-4.09 (m, 1H) 2.73 (t, 2H) 2.27 (s, 3H) 1.69 (d, 2H) 1.48-1.65 (m, 4H) 1.24-1.48 (m, 7H) 0.96-1.18 (m, 2H) 0.87 (d, 3H)
HPLC-MS: m/z=476 (M+1)

Example 47

2-{2-[3-[3-(4-Chloro-phenylsulfanyl)-propyl]-3-(trans-4-methyl-cyclohexyl)-ureido]-thiazol-5-ylsulfanyl}-2-methyl-propionic acid

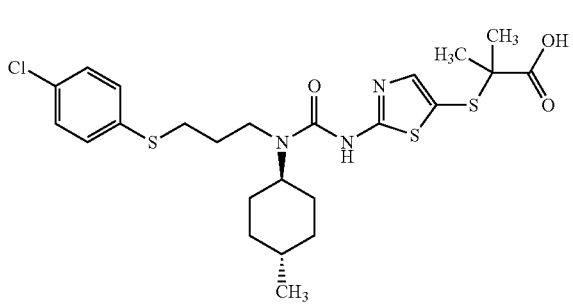 [SMILES: CC(C)(Sc1cnc(NC(=O)N(CCCSc2ccc(Cl)cc2)[C@H]2CC[C@H](C)CC2)s1)C(=O)O]

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 2-(2-amino-thiazol-5-ylsulfanyl)-2-methyl-propionic acid ethyl ester and 4-chloro-thiophenol.

¹H NMR (400 MHz, DMSO-d₆) (ppm) 7.40 (s, 1H) 7.37 (s, 4H) 3.82-4.06 (m, 1H) 3.01 (t, 2H) 1.70-1.83 (m, 2H) 1.65 (d, 2H) 1.41-1.56 (m, 4H) 1.39 (s, 6H) 1.19-1.33 (m, 2H) 1.02 (q, 2H) 0.86 (d, 3H)
HPLC-MS: m/z=542 (M+1)

Example 48

2-{2-[3-[3-(3-Chloro-phenylsulfanyl)-propyl]-3-(trans-4-methyl-cyclohexyl)-ureido]-thiazol-5-ylsulfanyl}-2-methyl-propionic acid

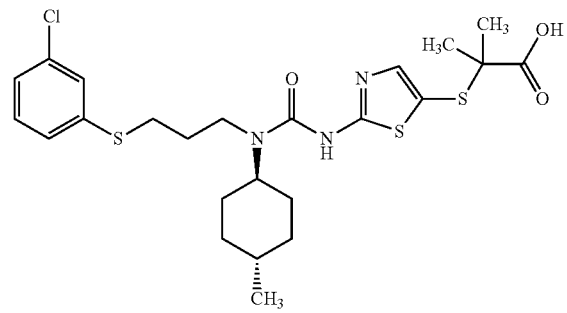 [SMILES: CC(C)(Sc1cnc(NC(=O)N(CCCSc2cccc(Cl)c2)[C@H]2CC[C@H](C)CC2)s1)C(=O)O]

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 2-(2-amino-thiazol-5-ylsulfanyl)-2-methyl-propionic acid ethyl ester and 3-chloro-thiophenol.

¹H NMR (400 MHz, DMSO-d₆) (ppm) 7.29-7.42 (m, 4H) 7.21-7.26 (m, 1H) 3.90-4.00 (m, 1H) 3.05 (t, 2H) 1.71-1.81 (m, 2H) 1.62-1.70 (m, 2H) 1.47-1.56 (m, 2H) 1.41-1.47 (m, 2H) 1.39 (s, 6H) 1.21-1.36 (m, 2H) 0.95-1.08 (m, 2H) 0.87 (d, 3H)
HPLC-MS: m/z=542 (M+1)

Example 49

2-{2-[3-[3-(4-Methoxy-phenylsulfanyl)-propyl]-3-(trans-4-methyl-cyclohexyl)-ureido]-thiazol-5-ylsulfanyl}-2-methyl-propionic acid

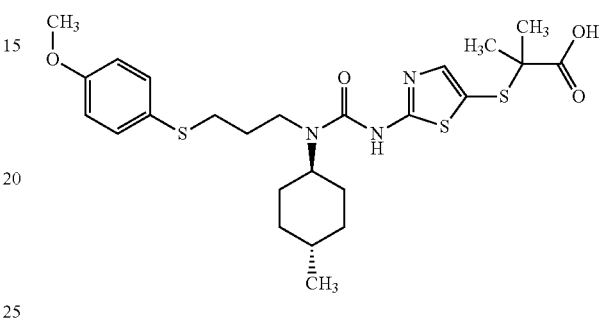

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 2-(2-amino-thiazol-5-ylsulfanyl)-2-methyl-propionic acid ethyl ester and 4-methoxy-thiophenol.

¹H NMR (400 MHz, DMSO-d₆) (ppm) 7.36 (s, 1H) 7.30 (d, 2H) 6.87 (d, 2H) 3.82-3.96 (m, 1H) 3.69 (s, 3H) 3.18-3.29 (m, 2H) 2.84 (t, 2H) 1.55-1.71 (m, 4H) 1.42-1.52 (m, 2H) 1.37-1.41 (m, 1H) 1.36 (s, 6H) 1.16-1.32 (m, 2H) 0.89-1.03 (m, 2H) 0.82 (d, 3H)
HPLC-MS: m/z=542 (M+1)

Example 50

2-{2-[3-[3-(3-Methoxy-phenylsulfanyl)-propyl]-3-(trans-4-methyl-cyclohexyl)-ureido]-thiazol-5-ylsulfanyl}-2-methyl-propionic acid

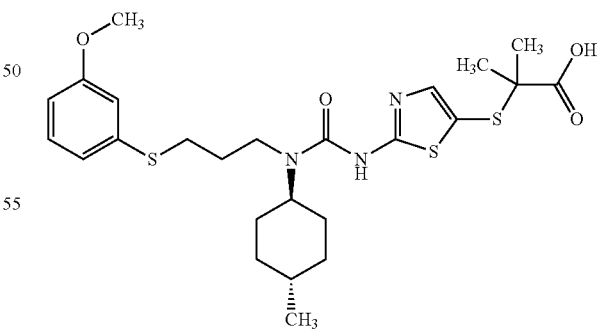

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 3-methoxy-thiophenol and 2-(2-amino-thiazol-5-ylsulfanyl)-2-methyl-propionic acid ethyl ester.

¹H NMR (400 MHz, DMSO-d₆) (ppm) 7.36 (s, 1H) 7.18 (t, 1H) 6.83-6.89 (m, 2H) 6.71 (dd, 1H) 3.82-3.96 (m, 1H) 3.70 (s, 3H) 2.96 (t, 2H) 1.66-1.78 (m, 2H) 1.56-1.65 (m, 2H) 1.37-1.51 (m, 5H) 1.35 (s, 6H) 1.15-1.28 (m, 2H) 0.91-1.04 (m, 2H) 0.82 (d, 3H)
HPLC-MS: m/z=538 (M+1)

Example 51

2-{2-[3-[3-(2-Fluoro-phenylsulfanyl)-propyl]-3-(trans-4-methyl-cyclohexyl)-ureido]-thiazol-5-ylsulfanyl}-2-methyl-propionic acid

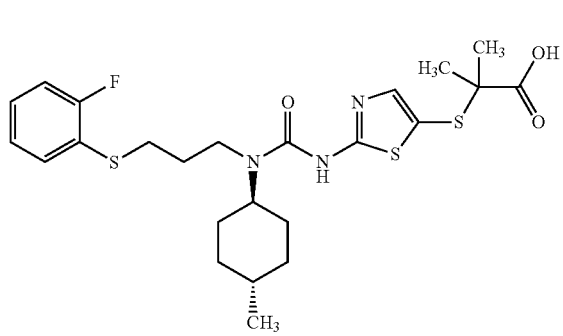

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 2-fluoro-thiophenol and 2-(2-amino-thiazol-5-ylsulfanyl)-2-methyl-propionic acid ethyl ester.

¹H NMR (400 MHz, DMSO-d₆) (ppm) 7.35-7.47 (m, 1H) 7.35 (s, 1H) 7.13-7.27 (m, 3H) 3.82-3.97 (m, 1H) 2.96 (t, 2H) 1.66-1.76 (m, 2H) 1.57-1.65 (m, 2H) 1.42-1.51 (m, 2H) 1.36-1.42 (m, 2H) 1.35 (s, 6H) 1.16-1.29 (m, 2H) 0.91-1.04 (m, 2H) 0.82 (d, 3H)
HPLC-MS: m/z=526 (M+1)

Example 52

2-{2-[3-[3-(4-Fluoro-phenylsulfanyl)-propyl]-3-(trans-4-methyl-cyclohexyl)-ureido]-thiazol-5-ylsulfanyl}-2-methyl-propionic acid

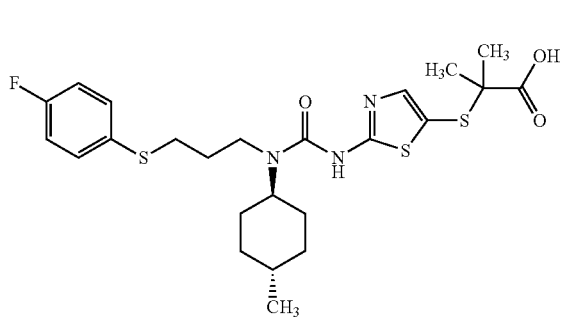 [SMILES: CC(C)(Sc1cnc(NC(=O)N(CCCSc2ccc(F)cc2)[C@H]2CC[C@H](C)CC2)s1)C(=O)O]

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 4-fluoro-thiophenol and 2-(2-amino-thiazol-5-ylsulfanyl)-2-methyl-propionic acid ethyl ester.

¹H NMR (400 MHz, DMSO-d₆) (ppm) 7.38-7.47 (m, 3H) 7.15-7.21 (m, 2H) 3.87-4.03 (m, 1H) 2.97 (t, 2H) 1.60-1.79 (m, 5H) 1.42-1.56 (m, 4H) 1.39 (s, 6H) 1.20-1.35 (m, 2H) 0.97-1.08 (m, 2H) 0.86 (d, 3H)
HPLC-MS: m/z=526 (M+1)

Example 53

2-Methyl-2-(2-{3-(trans-4-methyl-cyclohexyl)-3-[3-(2-trifluoromethoxy-phenylsulfanyl)-propyl]-ureido}-thiazol-5-ylsulfanyl)-propionic acid

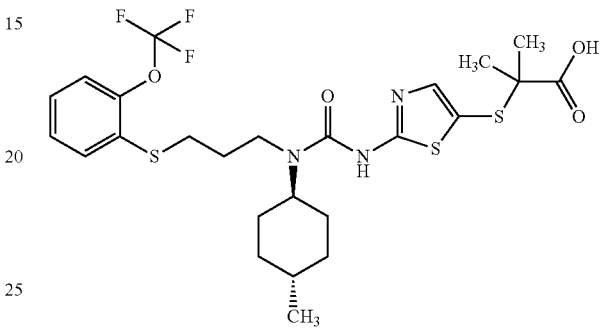

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 2-trifluoromethoxy-thiophenol and 2-(2-amino-thiazol-5-ylsulfanyl)-2-methyl-propionic acid ethyl ester.

¹H NMR (400 MHz, DMSO-d₆) (ppm) 7.54 (d, 1H) 7.35-7.43 (m, 3H) 7.25-7.34 (m, 1H) 3.88-4.01 (m, 1H) 3.05 (t, 2H) 1.72-1.84 (m, 2H) 1.60-1.70 (m, 2H) 1.42-1.56 (m, 5H) 1.39 (s, 6H) 1.21-1.36 (m, 2H) 0.97-1.08 (m, 2H) 0.86 (d, 3H)
HPLC-MS: m/z=592 (M+1)

Example 54

2-Methyl-2-(2-{3-(trans-4-methyl-cyclohexyl)-3-[3-(4-trifluoromethoxy-phenylsulfanyl)-propyl]-ureido}-thiazol-5-ylsulfanyl)-propionic acid

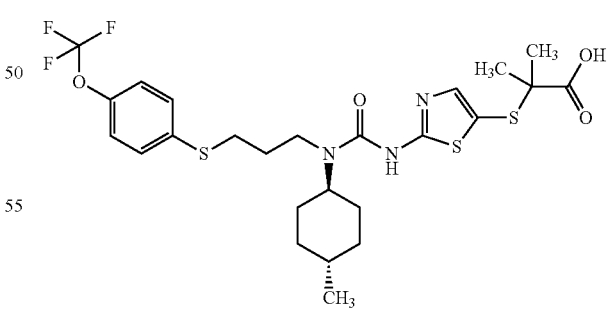

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 4-trifluoromethoxy-thiophenol.

¹H NMR (400 MHz, DMSO-d₆) (ppm) 7.47 (d, 2H) 7.40 (s, 1H) 7.32 (d, 2H) 3.87-4.01 (m, 1H) 3.24-3.39 (m, 2H) 3.03

(t, 2H) 1.70-1.84 (m, 2H) 1.58-1.70 (m, 2H) 1.41-1.55 (m, 4H) 1.39 (s, 6H) 1.19-1.32 (m, 2H) 0.94-1.09 (m, 2H) 0.86 (d, 3H)

HPLC-MS: m/z=592 (M+1)

Example 55

2-{2-[3-[3-(3-Fluoro-phenylsulfanyl)-propyl]-3-(trans-4-methyl-cyclohexyl)-ureido]-thiazol-5-ylsulfanyl}-2-methyl-propionic acid

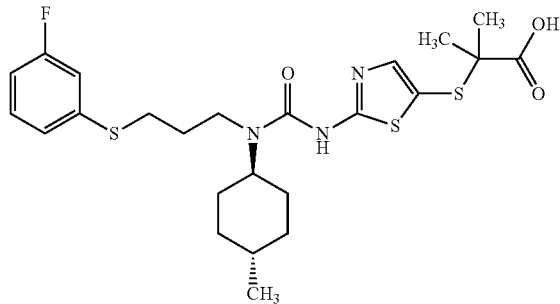 [SMILES: CC(C)(Sc1cnc(NC(=O)N(CCCSc2cccc(F)c2)[C@H]2CC[C@H](C)CC2)s1)C(=O)O]

The compound was prepared following an analogous procedure to the one described for the synthesis 2-{2-[3-[3-(2-methoxy-phenylsulfanyl)-propyl]-3-(trans-4-methyl-cyclohexyl)-ureido]-thiazol-5-ylsulfanyl}-2-methyl-propionic acid using 3-fluoro-thiophenol and 2-(2-amino-thiazol-5-ylsulfanyl)-2-methyl-propionic acid ethyl ester.

$^1$H NMR (400 MHz, DMSO-$d_6$) (ppm) 7.40 (s, 1H) 7.31-7.38 (m, 1H) 7.15-7.23 (m, 2H) 6.97-7.03 (m, 1H) 3.90-4.01 (m, 1H) 3.04 (t, 2H) 1.74-1.81 (m, 2H) 1.62-1.69 (m, 2H) 1.48-1.56 (m, 2H) 1.45 (dd, 2H) 1.22-1.36 (m, 3H) 0.96-1.09 (m, 2H) 0.86 (d, 3H)

HPLC-MS: m/z=526 (M+1)

Example 56

{2-[3-(trans-4-Methyl-cyclohexyl)-3-(3-oxo-3-phenyl-propyl)-ureido]-thiazol-5-ylsulfanyl}-acetic acid

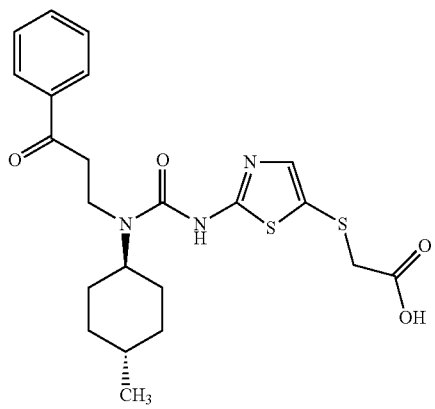 [SMILES: C[C@H]1CC[C@H](N(CCC(=O)c2ccccc2)C(=O)Nc2ncc(SCC(=O)O)s2)CC1]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 3-chloro-1-phenyl-propan-1-one and (2-aminothiazol-5-ylsulfanyl) acetic acid ethyl ester.

$^1$H NMR (400 MHz, CDCl$_3$) (ppm) 7.98 (d, 2H) 7.53-7.62 (m, 1H) 7.43-7.52 (m, 2H) 7.20 (s, 1H) 4.01-4.17 (m, 1H) 3.75 (t, 2H) 3.35 (t, 2H) 3.05 (s, 2H) 1.71-1.82 (m, 4H) 1.50-1.66 (m, 2H) 1.08-1.40 (m, 3H) 0.90 (d, 3H)

HPLC-MS: m/z=462 (M+1)

Example 57

{2[-3-[3-(4-Methoxy-phenyl)-propyl]-3-(4-methyl-cyclohexyl)-ureido]-thiazol-5-ylsulfanyl}-acetic acid

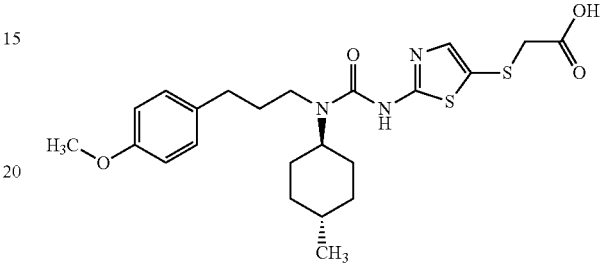

The compound was prepared following an analogous procedure to the one described for the synthesis of {2-[3-[3-(3-chloro-phenyl)-propyl]-3-(trans-4-methyl-cyclohexyl)-ureido]-thiazol-5-ylsulfanyl}-acetic acid using 3-(4-methoxy-phenyl)-propionic acid and (2-aminothiazol-5-ylsulfanyl) acetic acid ethyl ester.

1H NMR (300 MHz, DMSO-$d_6$) (ppm) 11.60 (br. s, 1H), 7.41 (s, 1H), 7.13 (d, 2H), 6.84 (d, 2H), 4.00-3.88 (m, 1H), 3.71 (s, 3H), 3.48 (s, 2H), 3.28-3.16 (m, 2H), 1.80-1.17 (m, 11H), 1.11-0.95 (m, 2H), 0.87 (d, 3H)

HPLC-MS: m/z=478 (M+1)

Example 58

{2-[-3-[3-(3-Methoxy-phenyl)-propyl]-3-(4-methyl-cyclohexyl)-ureido]-thiazol-5-ylsulfanyl}-acetic acid

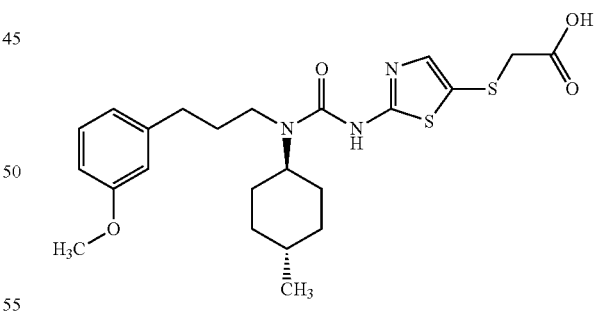

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 3-(3-methoxy-phenyl)-propionic acid and (2-aminothiazol-5-ylsulfanyl) acetic acid ethyl ester.

1H NMR (300 MHz, DMSO-$d_6$) (ppm) 11.70 (br. s, 1H), 7.41 (s, 1H), 7.19 (t, 1H), 6.68-6.60 (m, 3H), 4.02-3.88 (m, 1H), 3.71 (s, 3H), 3.48 (s, 2H), 3.28-3.14 (m, 2H), 2.57 (t, 2H), 1.75-1.15 (m, 11H), 1.11-0.95 (m, 2H), 0.87 (d, 3H)

HPLC-MS: m/z=478 (M+1)

Example 59

{2-[3-Benzyl-3-(trans-4-methyl-cyclohexyl)-ureido]-thiazol-5-ylsulfanyl}-acetic acid

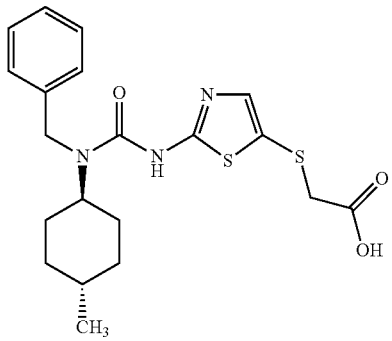 [SMILES: C[C@H]1CC[C@H](N(Cc2ccccc2)C(=O)Nc2ncc(SCC(=O)O)s2)CC1]

The compound was prepared using the procedure previously described for 2,2-dimethyl-3-{2-[3-(3-methyl-butyl)-3-(4-trans-methyl-cyclohexyl)-ureido]-thiazol-5-ylsulfanyl}-propionic acid using benzaldehyde and (2-aminothiazol-5-ylsulfanyl)acetic acid ethyl ester.

$^1$H NMR (400 MHz, DMSO-$d_6$) (ppm) 7.38 (s, 1H) 7.27-7.34 (m, 2H) 7.17-7.24 (m, 3H) 4.60 (br. s., 2H) 4.10-4.20 (m, 1H) 3.47 (s, 2H) 1.52-1.67 (m, 4H) 1.37-1.51 (m, 2H) 1.19-1.31 (m, 1H) 0.97-1.10 (m, 2H) 0.84 (d, 3H)

HPLC-MS: m/z=420 (M+1)

Example 60

(2-{3-(trans-4-Methyl-cyclohexyl)-3-[2-(toluene-4-sulfonyl)-ethyl]-ureido}-thiazol-5-ylsulfanyl)-acetic acid

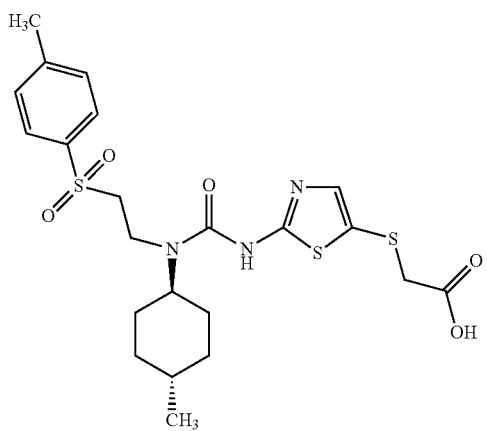 [SMILES: Cc1ccc(S(=O)(=O)CCN(C(=O)Nc2ncc(SCC(=O)O)s2)[C@H]2CC[C@H](C)CC2)cc1]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 1-(2-chloro-ethanesulfonyl)-4-methyl-benzene and (2-aminothiazol-5-ylsulfanyl)acetic acid ethyl ester.

$^1$H NMR (400 MHz, DMSO-$d_6$) (ppm) 7.84 (d, 2H) 7.51 (d, 2H) 7.39 (s, 1H) 3.87-3.99 (m, 1H) 3.47 (s, 2H) 2.43 (s, 3H) 1.50-1.62 (m, 4H) 1.06-1.20 (m, 3H) 0.92-1.05 (m, 2H) 0.84 (d, 3H)

HPLC-MS: m/z=512 (M+1)

Example 61

{2[-3-(3-Cyclohexyl-propyl)-3-(trans-4-methyl-cyclohexyl)-ureido]-thiazol-5-ylsulfanyl}-acetic acid

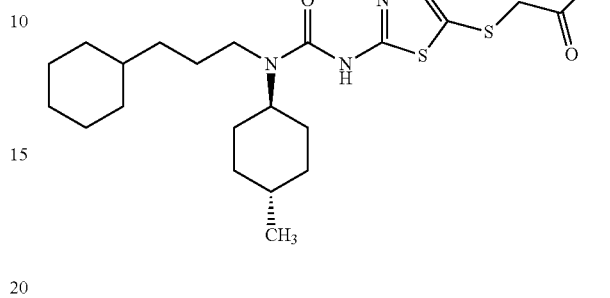

The compound was prepared following an analogous procedure to the one described for the synthesis of {2[-3-[3-(3-chloro-phenyl)-propyl]-3-(trans-4-methyl-cyclohexyl)-ureido]-thiazol-5-ylsulfanyl}-acetic acid using 3-cyclohexyl-propionic acid and (2-aminothiazol-5-ylsulfanyl)acetic acid ethyl ester.

1H NMR (300 MHz, DMSO-$d_6$) (ppm) 11.78 (br. s, 1H), 7.40 (s, 1H), 4.01-3.88 (m, 1H), 3.48 (s, 2H), 3.22-3.08 (m, 2H), 1.75-0.74 (m, 26H), 0.87 (d, 3H)

HPLC-MS: m/z=454 (M+1)

Example 62

(2-{-3-(trans-4-Methyl-cyclohexyl)-3-[3-(3-trifluoromethyl-phenyl)-propyl]-ureido}-thiazol-5-ylsulfanyl)-acetic acid

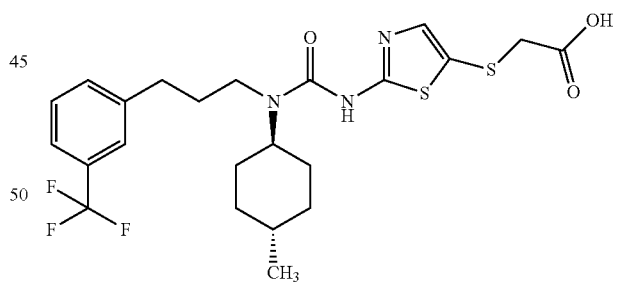

The compound was prepared following an analogous procedure to the one described for the synthesis of {2[-3-[3-(3-Chloro-phenyl)-propyl]-3-(trans-4-methyl-cyclohexyl)-ureido]-thiazol-5-ylsulfanyl}-acetic acid using 3-(3-trifluoromethyl-phenyl)-propionic acid and (2-aminothiazol-5-ylsulfanyl)acetic acid ethyl ester.

$^1$H NMR (300 MHz, DMSO-$d_6$) (ppm) 12.02 (br. s, 1H), 7.61-7.48 (m, 4H), 7.42 (s, 1H), 4.01-3.88 (m, 1H), 3.48 (s, 2H), 3.28-3.12 (m, 2H), 2.58 (t, 2H), 1.90-1.15 (m, 10H), 1.12-0.95 (m, 2H), 0.85 (d, 3H)

HPLC-MS: m/z=516 (M+1)

Example 63

{2[-3-[3-(4-Chloro-phenyl)-propyl]-3-(trans-4-methyl-cyclohexyl)-ureido]-thiazol-5-ylsulfanyl}-acetic acid

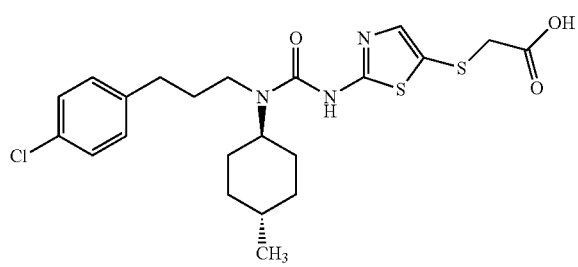 [SMILES: C[C@H]1CC[C@H](N(CCCc2ccc(Cl)cc2)C(=O)Nc2ncc(SCC(=O)O)s2)CC1]

The compound was prepared following an analogous procedure to the one described for the synthesis of {2[-3-[3-(3-Chloro-phenyl)-propyl]-3-(trans-4-methyl-cyclohexyl)-ureido]-thiazol-5-ylsulfanyl}-acetic acid using 3-(4-chloro-phenyl)-propionic acid and (2-aminothiazol-5-ylsulfanyl) acetic acid ethyl ester.

$^1$H NMR (300 MHz, DMSO-$d_6$) (ppm) 12.02 (br. s, 1H), 7.42 (s, 1H), 7.33 (d, 2H), 7.23 (d, 2H), 4.02-3.88 (m, 1H), 3.48 (s, 2H), 3.30-3.17 (m, 2H), 2.58 (t, 2H), 1.90-1.15 (m, 10H), 1.11-0.94 (m, 2H), 0.85 (d, 3H)

HPLC-MS: m/z=482 (M+1)

Example 64

{2[-3-[3-(3-Chloro-phenyl)-propyl]-3-(trans-4-methyl-cyclohexyl)-ureido]-thiazol-5-ylsulfanyl}-acetic acid

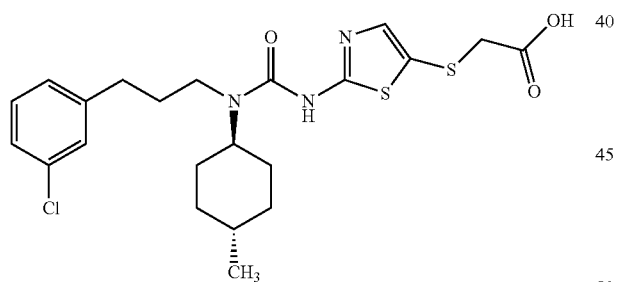

Amine Preparation:

To solution of 4-trans-methyl-cyclohexylamine hydrochloride (500 mg, 3.3 mmol) and 3-(3-chlorophenyl)propionic acid (609 mg, 3.30 mmol) in DCM (25 mL) was added HOBt (445 mg, 3.3 mmol) and EDAC (633 mg, 3.3 mmol). The mixture was stirred for 10 min at room temperature before the addition of DIPEA (1.13 mL, 6.6 mmol) and the resulting solution was stirred for a further 16 h at room temperature. DCM (25 mL) was added and the organics were washed with water (2×15 mL), 1N NaOH (10 mL), dried (MgSO$_4$), filtered and concentrated in vacuo to yield 900 mg of 3-(3-Chloro-phenyl)-N-(trans-4-methyl-cyclohexyl)-propionamide.

1M Lithium aluminium hydride (5 mL, 5 mmol) and dry THF (5 mL) was cooled to 0° C. where upon 98% sulphuric acid (133 µL, 2.5 mmol) was added over a period of 10 min. The resulting solution was stirred for 10 min at 0° C. and then allowed to warm to room temperature over 30 min. 3-(3-Chloro-phenyl)-N-(trans-4-methyl-cyclohexyl)-propionamide (900 mg, 3.2 mmol) in THF (6 mL) was added and the solution stirred for 16 h at room temperature. The reaction was quenched by the sequential addition of water (190 µL), 4N NaOH (190 µL) and water (190 µL). Dilution with THF (25 mL) followed by the addition of MgSO$_4$ (5 g), filtration and concentration in vacuo yielded 700 mg of [3-(3-Chloro-phenyl)-propyl]-(trans-4-methyl-cyclohexyl)-amine.

Urea Formation and Ester Hydrolysis:

To a solution of [3-(3-chloro-phenyl)-propyl]-(4-methyl-cyclohexyl)-amine (266 mg, 1 mmol) in THF (10 mL) was added 3-(2-Amino-thiazol-5-ylsulfanyl)-acetic acid ethyl ester (218 mg, 1 mmol), CDI (486 mg, 3 mmol), DMAP (6 mg, 0.05 mmol) and the resulting mixture was stirred for 16 h. The reaction mixture was purified by column chromatography (Kiselgel 60 heptane:EtOAc, 6:4) and the combined product fractions evaporated in vacuo to give 350 mg of {2-[3-[3-(3-Chloro-phenyl)-propyl]-3-(trans-4-methyl-cyclohexyl)-ureido]-thiazol-5-ylsulfanyl}-acetic acid ethyl ester.

This was dissolved in ethanol (15 mL) followed by the addition of 4N NaOH (1 mL) and the resulting solution stirred for 1.5 h. 1N HCl (6 mL) was added followed by water (20 mL) and the resulting precipitate was filtered, washed with water and dried in vacuo to yield 260 mg of {2[-3-[3-(3-Chloro-phenyl)-propyl]-3-(trans-4-methyl-cyclohexyl)-ureido]-thiazol-5-ylsulfanyl}-acetic acid.

$^1$H NMR (300 MHz, DMSO-$d_6$) ppm 12.02 (br. s, 1H), 7.42 (s, 1H), 7.35-7.10 (m, 4H), 4.02-3.88 (m, 1H), 3.48 (s, 2H), 3.30-3.15 (m, 2H), 2.58 (t, 2H), 1.90-1.15 (m, 10H), 1.12-0.93 (m, 2H), 0.85 (d, 3H)

HPLC-MS: m/z=482 (M+1)

Example 65

{2-[3-[4-(4-Methoxy-phenyl)-butyl]-3-(4-methyl-cyclohexyl)-ureido]-thiazol-5-ylsulfanyl}-acetic acid

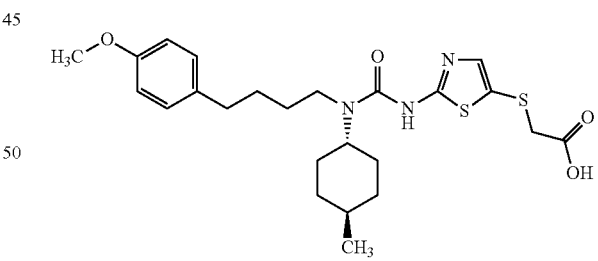

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 4-(4-methoxyphenyl)-butyric-acid and (2-aminothiazol-5-ylsulfanyl) acetic acid ethyl ester.

$^1$H NMR (400 MHz, DMSO-$d_6$) (ppm) 7.41 (s, 1H), 7.11 (d, 2H), 6.83 (d, 2H), 3.97-3.88 (m, 1H), 3.71 (s, 3H), 3.48 (s, 2H), 3.24-3.17 (m, 2H), 1.71-1.63 (m, 2H), 1.58-1.42 (m, 8H), 1.36-1.25 (m, 1H), 1.10-0.97 (m, 2H), 0.86 (d, 3H)

HPLC-MS: m/z=492 (M+1)

Example 66

{2-[3-(4-Methyl-cyclohexyl)-3-(4-p-tolyl-butyl)-ureido]-thiazol-5-ylsulfanyl}-acetic acid

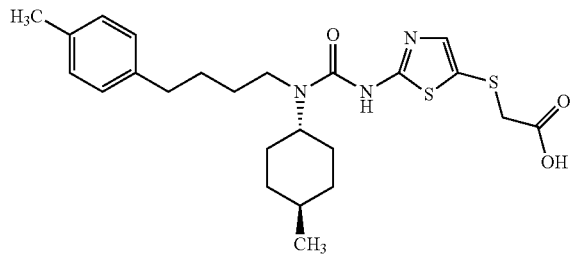 [SMILES: Cc1ccc(CCCCN(C(=O)Nc2ncc(SCC(=O)O)s2)[C@H]2CC[C@H](C)CC2)cc1]

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 4-(4-methyl-phenyl)-butyric-acid and (2-aminothiazol-5-ylsulfanyl) acetic acid ethyl ester.

$^1$H NMR (400 MHz, DMSO-$d_6$) (ppm) 7.41 (s, 1H), 7.07 (s, 4H), 3.98-3.86 (m, 1H), 3.47 (s, 2H), 3.25-3.16 (m, 2H), 2.57-2.53 (m, 2H), 2.25 (s, 3H), 1.71-1.63 (m, 2H), 1.59-1.41 (m, 8H), 1.36-1.23 (m, 1H), 1.10-0.96 (m, 2H), 0.86 (d, 3H)

HPLC-MS: m/z=476 (M+1)

Example 67

{2[-3-[3-(4-Fluoro-phenyl)-propyl]-3-(trans-4-methyl-cyclohexyl)-ureido]-thiazol-5-ylsulfanyl}-acetic acid

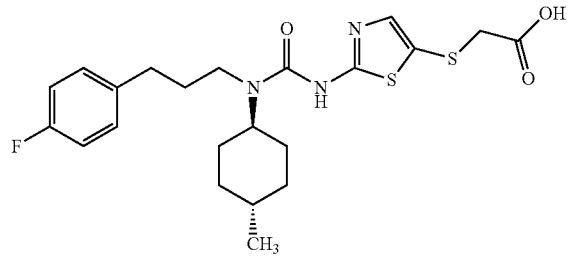 [SMILES: C[C@H]1CC[C@H](N(CCCc2ccc(F)cc2)C(=O)Nc2ncc(SCC(=O)O)s2)CC1]

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 3-(4-fluoro-phenyl)-propanoic-acid and (2-aminothiazol-5-ylsulfanyl) acetic acid ethyl ester.

$^1$H NMR (300 MHz, DMSO-$d_6$) (ppm) 12.02 (br. s, 1H), 7.42 (s, 1H), 7.30-7.18 (m, 2H), 7.15-7.10 (m, 2H), 4.02-3.88 (m, 1H), 3.48 (s, 2H), 3.30-3.17 (m, 2H), 2.58 (t, 2H), 1.90-1.15 (m, 10H), 1.13-0.94 (m, 2H), 0.85 (d, 3H)

HPLC-MS: m/z=466 (M+1)

Example 68

{2-[3-[3-(5-Chloro-benzofuran-3-yl)-propyl]-3-(trans-4-methyl-cyclohexyl)-ureido]-thiazol-5-ylsulfanyl}-acetic acid

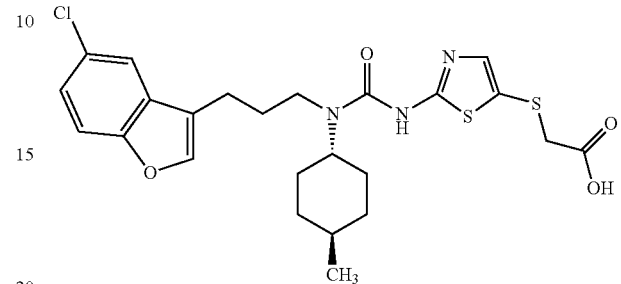

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 3-(5-chloro-benzofuran-3-yl)-propionic acid and (2-aminothiazol-5-ylsulfanyl)acetic acid ethyl ester.

$^1$H NMR (400 MHz, DMSO-$d_6$) (ppm) 7.91 (s, 1H), 7.75 (s, 1H), 7.59 (d, 1H), 7.43 (s, 1H), 7.33 (d, 1H), 4.04-3.88 (m, 1H), 3.48 (s, 2H), 3.36-3.26 (m, 2H), 2.72-2.59 (m, 2H), 1.92-1.76 (m, 2H), 1.73-1.40 (m, 6H), 1.34-1.19 (m, 1H), 1.12-0.95 (m, 2H), 0.86 (d, 3H)

HPLC-MS: m/z=522 (M+1)

Example 69

{2-[3-[4-(4-Chloro-phenyl)-butyl]-3-(trans-4-methyl-cyclohexyl)-ureido]-thiazol-5-ylsulfanyl}-acetic acid

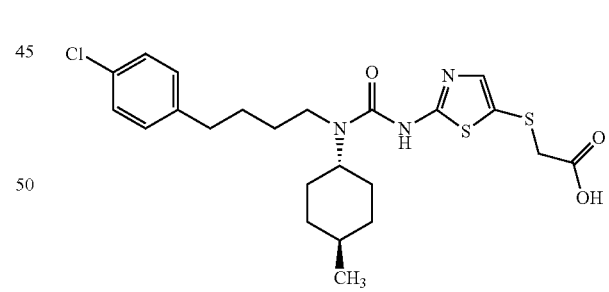

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 4-(4-chloro-phenyl)-butyric acid and (2-aminothiazol-5-ylsulfanyl)acetic acid ethyl ester.

$^1$H NMR (400 MHz, DMSO-$d_6$) (ppm) 7.41 (s, 1H), 7.30 (d, 2H), 7.21 (d, 2H), 3.97-3.85 (m, 1H), 3.48 (s, 2H), 3.26-3.15 (m, 2H), 2.64-2.52 (m, 2H), 1.75-1.39 (m, 10H), 1.38-1.22 (m, 1H), 1.12-0.95 (m, 2H), 0.86 (d, 3H)

HPLC-MS: m/z=496 (M+1)

Example 70

{2-[3-(trans-4-Methyl-cyclohexyl)-3-(3-pyridin-3-yl-propyl)-ureido]-thiazol-5-ylsulfanyl}-acetic acid

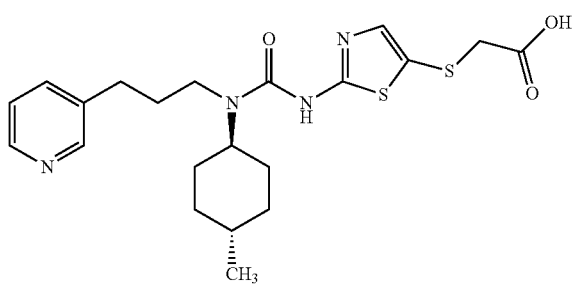 [SMILES: C[C@H]1CC[C@H](N(CCCc2cccnc2)C(=O)Nc2ncc(SCC(=O)O)s2)CC1]

To solution of 3(3-pyidyl)-1-propanol (1.37 g, 10 mmol) in ethyl acetate (25 mL) cooled to 0° C. was added DIPEA (1.71 mL, 10 mmol) followed by methane sulphonyl chloride (0.77 mL, 10 mmol) and the resulting reaction mixture stirred for 15 min at 0° C. and 3 h at room temperature. Water (25 mL) was added and the organics were separated, dried (MgSO$_4$), filtered and concentrated in vacuo to yield the corresponding mesylate. This was dissolved in acetone (10 mL) followed by the addition of potassium carbonate (3 g, 21 mmol), potassium iodide (1 g, 6 mmol) and 4-trans-methyl-cyclohexylamine hydrochloride (1.75 g, 11.6 mmol). The mixture was stirred for 60 h at room temperature then filtered and the solvents removed by evaporation. The resulting solid was slurried with ethyl acetate (20 mL), filtered and the organics were dried (MgSO$_4$), filtered and concentrated in vacuo to yield the crude (trans-4-methyl-cyclohexyl)-(3-pyridin-3-yl-propyl)amine which was used without further purification.

The amine was coupled and the resulting ester hydrolyzed as previously described for {2[-3-[3-(3-chloro-phenyl)-propyl]-3-(trans-4-methyl-cyclohexyl)-ureido]-thiazol-5-ylsulfanyl}-acetic acid $^1$H NMR (300 MHz, DMSO-d$_6$) (ppm) 8.89 (s, 1H), 8.80 (d, 1H), 8.55 (d, 1H), 8.04 (t, 1H), 7.45 (s, 1H), 4.05-3.90 (m, 1H), 3.50 (s, 2H), 3.29 (t, 2H), 2.84 (t, 2H), 2.51-2.48 (m, 3H), 1.94-1.78 (m, 2H), 1.75-1.43 (m, 6H), 1.41-0.98 (m, 4H), 0.87 (d, 3H)

HPLC-MS: m/z=449 (M+1)

Example 71

{2[-3-(trans-4-Methyl-cyclohexyl)-3-(trans-2-phenyl-cyclopropylmethyl)-ureido]-thiazol-5-ylsulfanyl}-acetic acid

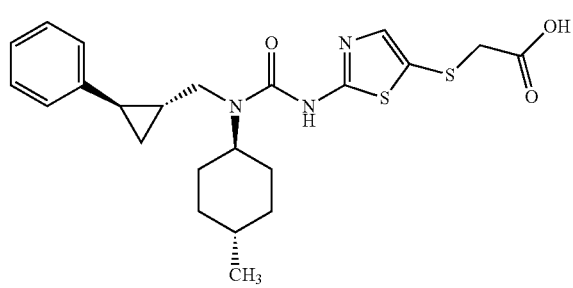 [SMILES: C[C@H]1CC[C@H](N(C[C@@H]2C[C@H]2c2ccccc2)C(=O)Nc2ncc(SCC(=O)O)s2)CC1]

The compound was prepared following an analogous procedure to the one described for the synthesis of {2-[-3-[3-(3-chloro-phenyl)-propyl]-3-(trans-4-methyl-cyclohexy)-ureido]-thiazol-5-ylsulfanyl}-acetic acid using trans-2-phenylcyclopropanecarboxylic acid and (2-aminothiazol-5-ylsulfanyl)acetic acid ethyl ester.

$^1$H NMR (300 MHz, DMSO-d$_6$) (ppm) 11.58 (br. s, 1H), 7.41 (s, 1H), 7.24-7.15 (m, 2H), 7.11-7.05 (m, 1H), 7.03-6.95 (m, 2H), 3.98-3.87 (m, 1H), 3.48 (s, 2H), 1.99-1.88 (m, 1H), 1.75-0.90 (m, 14H), 0.87 (d, 3H)

HPLC-MS: m/z=460 (M+1)

Example 72

{2-[3-(2-Methanesulfonyl-ethyl)-3-(trans-4-methyl-cyclohexyl)-ureido]-thiazol-5-ylsulfanyl}-acetic acid

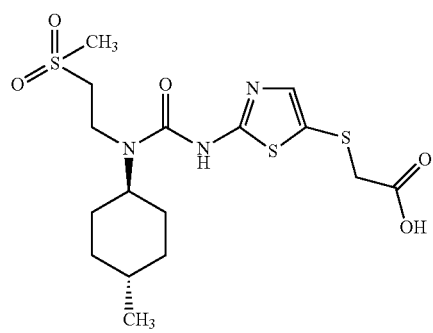 [SMILES: CS(=O)(=O)CCN(C(=O)Nc1ncc(SCC(=O)O)s1)[C@H]1CC[C@H](C)CC1]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 1-chloro-2-methanesulfonyl-ethane (Prepared as described in Chem. Ber. 1894, 27, 3048) and (2-aminothiazol-5-ylsulfanyl)acetic acid ethyl ester.

$^1$H NMR (400 MHz, DMSO-d$_6$) (ppm) 12.15 (br.s, 1H) 7.42 (s, 1H) 3.97-4.08 (m, 1H) 3.61 (t, 2H) 3.49 (s, 2H) 3.06 (s, 3 □H) 1.60-1.74 (m, 4H) 1.47-1.59 (m, 2H) 1.30-1.37 (m, 1H) 1.01-1.14 (m, 2H) 0.87 (d, 3H)

HPLC-MS: m/z=436 (M+1)

Example 73

{2-[3-Benzo[1,3]dioxol-5-ylmethyl-3-(trans-4-methyl-cyclohexyl)-ureido]-thiazol-5-ylsulfanyl}-acetic acid

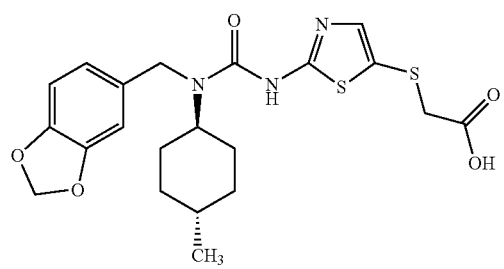 [SMILES: C[C@H]1CC[C@H](N(Cc2ccc3c(c2)OCO3)C(=O)Nc2ncc(SCC(=O)O)s2)CC1]

The compound was prepared using the procedure previously described for 2,2-dimethyl-3-{2-[3-(3-methyl-butyl)-

3-(4-trans-methyl-cyclohexyl)-ureido]-thiazol-5-ylsulfanyl}-propionic acid using benzo[1,3]dioxole-5-carbaldehyde and (2-aminothiazol-5-ylsulfanyl)acetic acid ethyl ester.

$^1$H NMR (400 MHz, DMSO-$d_6$) (ppm) 7.40 (s, 1H) 6.84 (d, 1H) 6.77 (s, 1H) 6.69 (d, 1H) 5.98 (s, 2H) 4.49 (s, 2H) 4.05-4.17 (m, 1H) 3.49 (s, 2H) 1.60-1.68 (m, 2H) 1.40-1.57 (m, 4H) 1.21-1.31 (m, 1H) 0.97-1.08 (m, 2H) 0.84 (d, 3H)

HPLC-MS: m/z=464 (M+1)

Example 74

{2-[3-[4-(1H-Indol-3-yl)-butyl]-3-(trans-4-methyl-cyclohexyl)-ureido]-thiazol-5-ylsulfanyl}-acetic acid

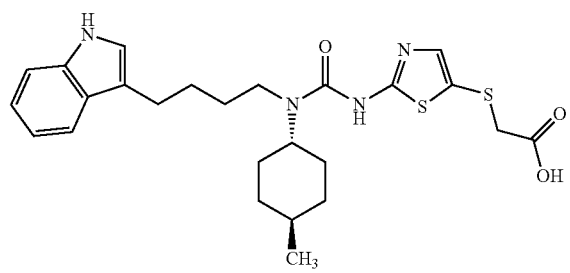 [SMILES: C[C@H]1CC[C@H](N(CCCCc2c[nH]c3ccccc23)C(=O)Nc2ncc(SCC(=O)O)s2)CC1]

The compound was prepared following an analogous procedure to the one described for the synthesis of {2-[-3-[3-(3-chloro-phenyl)-propyl]-3-(trans-4-methyl-cyclohexy)-ureido]-thiazol-5-ylsulfanyl}-acetic acid using 4-(1H-indol-3-yl)-butyric acid and (2-aminothiazol-5-ylsulfanyl)acetic acid ethyl ester.

$^1$H NMR (400 MHz, DMSO-$d_6$) (ppm) 10.74 (s, 1H), 7.51 (d, 1H), 7.41 (s, 1H), 7.31 (d, 1H), 7.11 (s, 1H), 7.04 (t, 1H), 6.95 (t, 1H), 3.98-3.86 (m, 1H), 3.47 (s, 2H), 3.28-3.19 (m, 2H), 2.75-2.65 (m, 2H), 1.73-1.40 (m, 10H), 1.36-1.21 (m, 1H), 1.10-0.95 (m, 2H), 0.85 (d, 3H)

HPLC-MS: m/z=501 (M+1)

Example 75

{2-[3-(4-Cyclohexyl-butyl)-3-(trans-4-methyl-cyclohexyl)-ureido]-thiazol-5-ylsulfanyl}-acetic acid

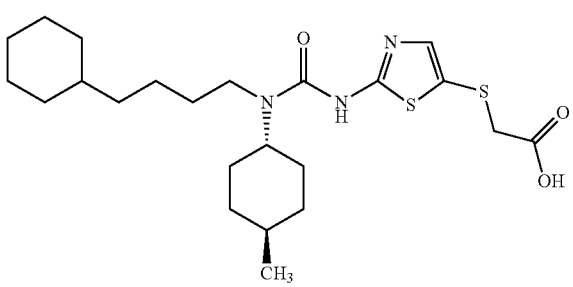 [SMILES: C[C@H]1CC[C@H](N(CCCCC2CCCCC2)C(=O)Nc2ncc(SCC(=O)O)s2)CC1]

The compound was prepared following an analogous procedure to the one described for the synthesis of {2[-3-[3-(3-chloro-phenyl)-propyl]-3-(trans-4-methyl-cyclohexyl)-ureido]-thiazol-5-ylsulfanyl}-acetic acid using 4-cyclohexyl-butyric acid and (2-aminothiazol-5-ylsulfanyl)acetic acid ethyl ester.

$^1$H NMR (400 MHz, DMSO-$d_6$) (ppm) 7.41 (s, 1H) 4.01-3.88 (m, 1H), 3.47 (s, 2H), 3.25-3.12 (m, 2H), 1.77-0.95 (m, 24H), 0.94-0.73 (m, 5H)

HPLC-MS: m/z=468 (M+1)

Example 76

{2-[3-[4-(4-Fluoro-phenyl)-4-hydroxy-butyl]-3-(trans-4-methyl-cyclohexyl)-ureido]-thiazol-5-ylsulfanyl}-acetic acid

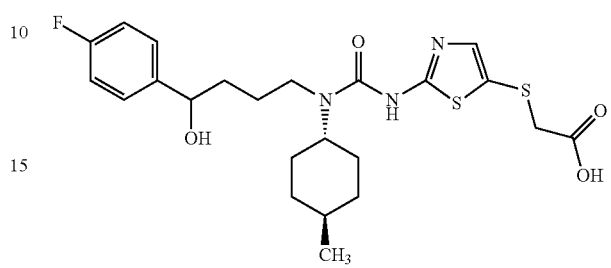

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 4-(4-fluoro-phenyl)-4-oxo-butyric acid and (2-aminothiazol-5-ylsulfanyl)acetic acid ethyl ester.

$^1$H NMR (400 MHz, DMSO-$d_6$) (ppm) 7.46-7.29 (m, 3H), 7.18-7.03 (m, 2H), 4.61-4.48 (m, 1H), 4.00-3.82 (m, 1H), 3.47 (s, 2H), 3.25-3.12 (m, 2H), 1.74-1.20 (m, 11H), 1.11-0.95 (m, 2H), 0.87 (d, 3H)

HPLC-MS: m/z=496 (M+1)

Example 77

{2-[3-[4-(3-Fluoro-4-methoxy-phenyl)-4-hydroxy-butyl]-3-(trans-4-methyl-cyclohexyl)-ureido]-thiazol-5-ylsulfanyl}-acetic acid

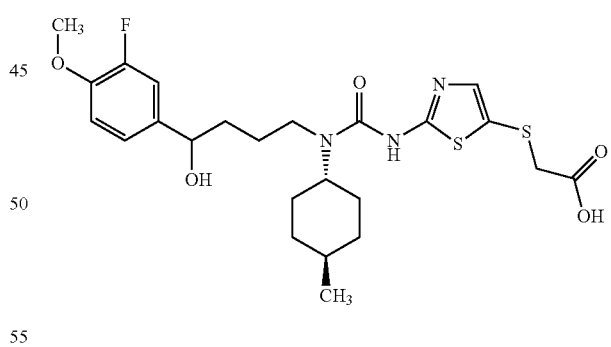

The compound was prepared following an analogous procedure to the one described for the synthesis of {2[-3-[3-(3-chloro-phenyl)-propyl]-3-(trans-4-methyl-cyclohexyl)-ureido]-thiazol-5-ylsulfanyl}-acetic acid using 4-(3-fluoro-4-methoxy-phenyl)-4-oxo-butyric acid and (2-aminothiazol-5-ylsulfanyl)acetic acid ethyl ester.

HPLC-MS: m/z=526 (M+1)

Example 78

{2-[3-(trans-4-Methyl-cyclohexyl)-3-(1,2,3,4-tetrahydro-naphthalen-2-ylmethyl)-ureido]-thiazol-5-ylsulfanyl}-acetic acid

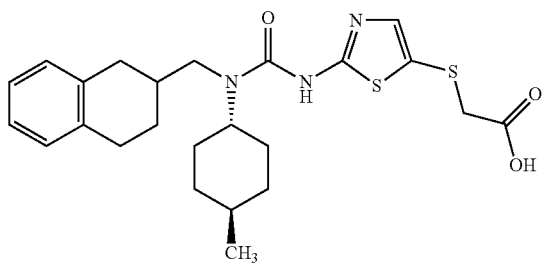 [SMILES: C[C@H]1CC[C@H](N(CC2CCc3ccccc3C2)C(=O)Nc2ncc(SCC(=O)O)s2)CC1]

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 1,2,3,4-tetrahydro-naphthalene-2-carboxylic acid and (2-aminothiazol-5-ylsulfanyl)acetic acid ethyl ester.

$^1$H NMR (400 MHz, DMSO-d$_6$) (ppm) 7.41 (s, 1H), 7.04 (s, 4H), 3.95-3.86 (m, 1H), 3.48 (s, 2H), 2.84-2.62 (m, 3H), 2.48-2.38 (m, 1H), 2.05-1.95 (m, 1H), 1.88-1.81 (m, 1H), 1.76-1.56 (m, 6H), 1.41-1.27 (m, 2H), 1.13-1.00 (m, 2H), 0.86 (d, 3H)

HPLC-MS: m/z=474 (M+1)

Example 79

2-{2-[3-[2-(4-Acetyl-phenyl)-ethyl]-3-(trans-4-methyl-cyclohexyl)-ureido]-thiazol-5-ylsulfanyl}-2-methyl-propionic acid

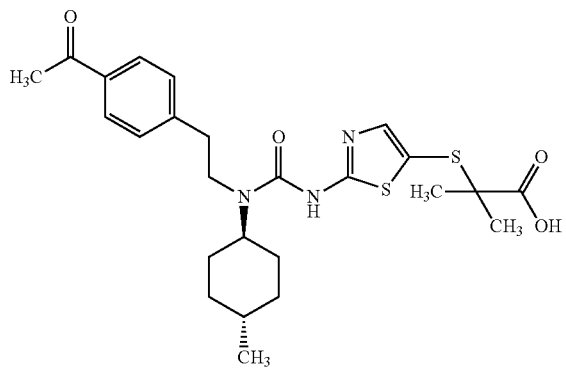 [SMILES: CC(=O)c1ccc(CCN(C(=O)Nc2ncc(SC(C)(C)C(=O)O)s2)[C@H]2CC[C@H](C)CC2)cc1]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 1-[4-(2-chloro-ethyl)-phenyl]-ethanone and (2-aminothiazol-5-ylsulfanyl) acetic acid ethyl ester.

$^1$H NMR (400 MHz, DMSO-d$_6$) (ppm) 7.90 (d, 2H) 7.35-7.52 (m, 3H) 3.92-4.11 (m, 1H) 3.38-3.54 (m, 2H) 2.80-2.97 (m, 2H) 2.56 (s, 3H) 1.64-1.79 (m, 2H) 1.50-1.79 (m, 4H) 1.26-1.48 (m, 7H) 0.97-1.15 (m, 2H) 0.87 (d, 3H)

Example 80

{2-[3-[3-(1H-Indol-3-yl)-propyl]-3-(trans-4-methyl-cyclohexyl)-ureido]-thiazol-5-ylsulfanyl}-acetic acid

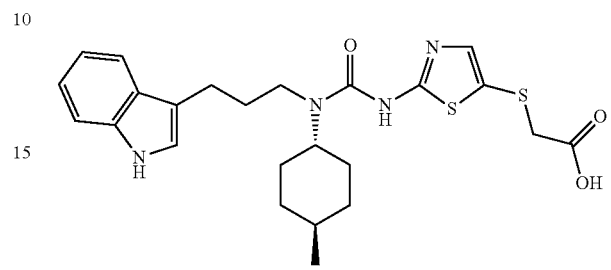

The compound was prepared following an analogous procedure to the one described for the synthesis of {2[-3-[3-(3-chloro-phenyl)-propyl]-3-(trans-4-methyl-cyclohexyl)-ureido]-thiazol-5-ylsulfanyl}-acetic acid using 3-(1H-indol-3-yl)-propionic acid (2-aminothiazol-5-ylsulfanyl)acetic acid ethyl ester.

$^1$H NMR (400 MHz, DMSO-d$_6$) (ppm) 10.76 (s, 1H), 7.51 (d, 1H), 7.42 (s, 1H), 7.32 (d, 1H), 7.14 (s, 1H), 7.09-7.02 (m, 1H), 7.00-6.93 (m, 1H), 4.01-3.89 (m, 1H), 3.48 (s, 2H), 2.74-2.65 (m, 2H), 1.92-1.80 (m, 2H), 1.69-1.52 (m, 4H), 1.52-1.37 (m, 2H), 1.29-1.16 (m, 1H), 1.09-0.95 (m, 2H), 0.84 (d, 3H)

HPLC-MS: m/z=487 (M+1)

Example 81

{2-[3-[4-(3,4-Dimethoxy-phenyl)-butyl]-3-(trans-4-methyl-cyclohexyl)-ureido]-thiazol-5-ylsulfanyl}-acetic acid

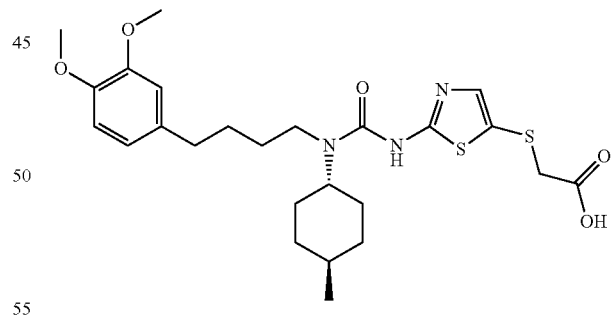

The compound was prepared following an analogous procedure to the one described for the synthesis of {2[-3-[3-(3-chloro-phenyl)-propyl]-3-(trans-4-methyl-cyclohexyl)-ureido]-thiazol-5-ylsulfanyl}-acetic acid using 4-(3,4-dimethoxy-phenyl)-butyric acid and (2-aminothiazol-5-ylsulfanyl)acetic acid ethyl ester.

$^1$H NMR (400 MHz, DMSO-d$_6$) (ppm) 7.41 (s, 1H), 6.83 (d, 1H), 6.80 (s, 1H), 6.70 (d, 1H), 3.99-3.87 (m, 1H), 3.73 (s, 3H), 3.70 (s, 3H), 3.48 (s, 2H), 3.27-3.17 (m, 2H), 1.73-1.42 (m, 10H), 1.37-1.23 (m, 1H), 1.10-0.97 (m, 2H), 0.86 (d, 3H)

HPLC-MS: m/z=523 (M+1)

Example 82

{2-[3-(trans-4-Methyl-cyclohexyl)-3-(2-methyl-2-phenyl-propyl)-ureido]-thiazol-5-ylsulfanyl}-acetic acid

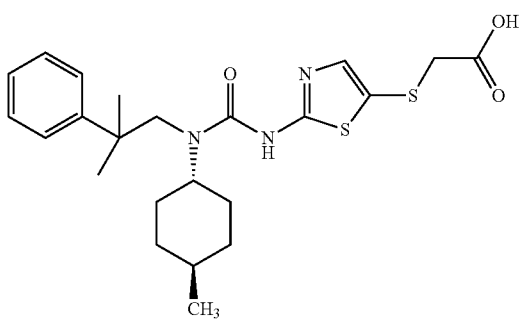 [SMILES: CC(C)(CN(C(=O)Nc1ncc(SCC(=O)O)s1)[C@H]1CC[C@H](C)CC1)c1ccccc1]

To a suspension of LiAlH$_4$ (4.64 g, 123.0 mmol) in dry THF (500 mL) was added 2-methyl-2-phenyl-propionic acid (20.0 g, 123.0 mmol) in dry THF (250 mL) dropwise at 55° C. over 10 min. The mixture was quenched with sodium hydroxide aqueous solution (60 mL, 15%). The mixture was filtered and the filtrate was dried over anhydrous sodium sulfate, filtered and evaporated to yield 2-methyl-2-phenyl-propan-1-ol (13.3 g, 72.7%), which was used to the next step without further purification.

To a solution of 2-methyl-2-phenyl-propan-1-ol (13.3 g, 87.0 mmol) in DMSO (150 mL) was added triethylamine (24.7 mL, 178.0 mmo) at rt, followed by pyridine sulfuric oxide (28.6 g, 180.0 mmol). The mixture was stirred for 2.5 h at rt. Water was added and the resulting mixture was extracted with dichloromethane. The organic layer was dried over anhydrous sodium sulfate and concentrated to obtain the crude product 2-methyl-2-phenyl-propionaldehyde (12.0 mg, 91.6%), which was used to the next step without further purification.

The mixture of 2-methyl-2-phenyl-propionaldehyde (3.3 g, 0.022 mol), 4-methyl-cyclohexylamine (2.5 g, 0.022 mol), NaBH$_3$CN (2.23 g, 0.035 mol) and acetic acid (2.12 g, 0.035 mol) in the mixed solvent of THF and methanol (150 mL, 3:1) was stirred at RT for 6 hs. Water was added and the mixture was extracted with dichloromethane. The organic layer was collected, dried over anhydrous sodium sulfate. The solvent was removed at reduced pressure and the residue was purified by preparative HPLC to give (4-methyl-cyclohexyl)-(2-methyl-2-phenyl-propyl)-amine as TFA salt (1.4 g, 26.0%).

To a mixture of (2-amino-thiazol-5-ylsulfanyl)-acetic acid methyl ester (416 mg, 2.04 mmol) in CH$_2$Cl$_2$ (30 mL) was added CDI (496 mg, 3.06 mmol) and DMAP (25 mg, 0.21 mmol) at room temperature. The reaction mixture was stirred at rt for 1.5 h, then (4-methyl-cyclohexyl)-(2-methyl-2-phenyl-propyl)-amine (500 mg, 2.04 mmol) was added. The mixture was stirred for 16 h at room temperature. The solvent was removed at reduced pressure and the residue was purified by preparative HPLC to give {2-[3-(4-methyl-cyclohexyl)-3-(2-methyl-2-phenyl-propyl)-ureido]-thiazol-5-ylsulfanyl}-acetic acid methyl ester (350 mg).

To a solution of {2-[3-(4-methyl-cyclohexyl)-3-(2-methyl-2-phenyl-propyl)-ureido]-thiazol-5-ylsulfanyl}-acetic acid methyl ester (350 mg, 0.737 mmol) in THF (50 mL) was added LiOH.H$_2$O (186 mg, 4.42 mmol) in water (3 mL) at RT. The mixture was stirred at RT for 16 h. Water was added and the mixture was extracted with dichloromethane. The organic layer was collected, dried over anhydrous sodium sulfate. The solvent was removed at reduced pressure and the residue was purified by preparative HPLC to give {2-[3-(trans-4-Methyl-cyclohexyl)-3-(2-methyl-2-phenyl-propyl)-ureido]-thiazol-5-ylsulfanyl}-acetic acid.

H NMR (400 MHz, CDCl$_3$): (ppm) 7.45-7.35 (m, 2H); 7.35-7.27 (m, 2H); 7.25-7.12 (m, 2H); 3.55 (s, 2H); 3.35 (s, 2H); 2.62-2.51 (m, 1H); 2.02-1.86 (m, 2H); 1.62-1.50 (m, 2H); 1.50-1.35 (m, 8H); 1.35-1.12 (m, 1H); 0.78 (d, 3H); 0.55 (q, 2H).

Example 83

{2-[3-(2,2-Difluoro-2-phenyl-ethyl)-3-(trans-4-methyl-cyclohexyl)-ureido]-thiazol-5-ylsulfanyl}-acetic acid FA (15 mM)=2.1 (0) EC$_{50}$ (15 mM)=0.289 (0)

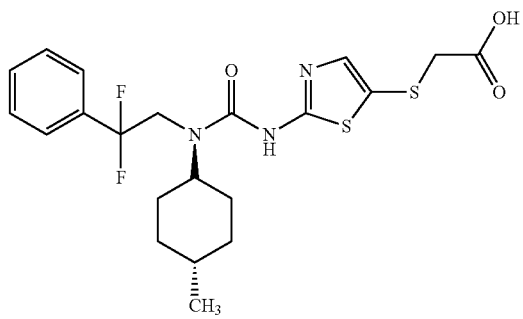

To a solution of difluoro-phenyl-acetic acid ethyl ester (5.0 g, 25.0 mmol) in ethanol (150 mL) was added sodium borohydride (1.37 g, 36 mmol) at rt. The mixture was stirred for 2.5 h at room temperature. HCl aqueous (1N) was added and the resulting mixture was extracted with dichloromethane. The organic layer was dried over anhydrous sodium sulfate and concentrated to obtain the product 2,2-difluoro-2-phenyl-ethanol (3.4 g, 86.1%), which was used to the next step without further purification.

To a solution of oxalyl chloride (2.66 g, 21.0 mmol) in DCM (300 mL) was added DMSO (2.5 mL, 35.0 mmol) at 60° C. The mixture was stirred for 30 min. Then 2,2-difluoro-2-phenyl-ethanol (28.1 g, 18.0 mmol) was added at the same temperature. The mixture was stirred for another 30 min. Triethylamine (11.1 mL, 80.0 mmol) was added and then the mixture was stirred for 2 h at room temperature. Water was added and the organic layer was dried over anhydrous sodium sulfate and concentrated to obtain the crude product difluoro-phenyl-acetaldehyde (828 mg, 30%), which was used to the next step without further purification.

The mixture of difluoro-phenyl-acetaldehyde (828 mg, 5.31 mmol), 4-methyl-cyclohexylamine (600 mg, 5.31 mmol), NaBH$_3$CN (535 mg, 8.50 mmol) and acetic acid (510 mg, 8.50 mmol) in the mixed solvent of THF and methanol (150 mL, 3:1) was stirred at RT for 6 h. Water was added and the mixture was extracted with dichloromethane. The organic layer was collected, dried over anhydrous sodium sulfate. The solvent was removed at reduced pressure and the residue was purified by preparative HPLC to give (2,2-difluoro-2-phenyl-ethyl)-(4-methyl-cyclohexyl)-amine as a TFA salt.

To a mixture of (2-amino-thiazol-5-ylsulfanyl)-acetic acid methyl ester (403 mg, 1.98 mmol) in CH$_2$Cl$_2$ (100 mL) was added CDI (480.2 mg, 2.96 mmol) and DMAP (25 mg, 0.20 mmol) at room temperature. The reaction mixture was stirred at room temperature for 1.5 h, and then (2,2-difluoro-2-phenyl-ethyl)-(4-methyl-cyclohexyl)-amine (500 mg, 1.98 mmol) was added. The mixture was stirred for 16 h at room temperature. The solvent was removed at reduced pressure and the residue was purified by preparative HPLC to give {2-[3-(2,2-difluoro-2-phenyl-ethyl)-3-(4-methyl-cyclohexyl)-ureido]-thiazol-5-ylsulfanyl}-acetic acid methyl ester.

To a solution of {2-[3-(2,2-difluoro-2-phenyl-ethyl)-3-(4-methyl-cyclohexyl)-ureido]-thiazol-5-ylsulfanyl}-acetic acid methyl ester (350 mg, 0.725 mmol) in THF (50 mL) was added LiOH.H₂O (183 mg, 4.35 mmol) in water (3 mL) at RT. The mixture was stirred at RT for 16 h. Water was added and the mixture was extracted with dichloromethane. The organic layer was collected, dried over anhydrous sodium sulfate. The solvent was removed at reduced pressure and the residue was purified by preparative HPLC to give {2-[3-(2,2-difluoro-2-phenyl-ethyl)-3-(trans-4-methyl-cyclohexyl)-ureido]-thiazol-5-ylsulfanyl}-acetic acid $^1$H NMR (400 MHz, CDCl₃): (ppm) 10.05 (s, 2H); 7.65 (s, 1H); 7.50 (s, 2H); 7.40 (s, 3H); 4.05 (t, 2H); 3.90-3.80 (m, 1H); 3.50 (s, 2H); 1.90-1.40 (m, 6H); 1.45-1.25 (m, 1H); 1.25-1.05 (m, 2H); 0.90 (d, 3H).

Example 84

{2-[3-(But-3-ynyl)-3-(trans-4-methyl-cyclohexyl)-ureido]-thiazol-5-ylsulfanyl}-acetic acid

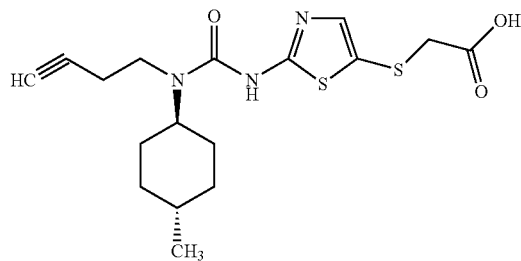 [SMILES: C#CCCN(C(=O)Nc1ncc(SCC(=O)O)s1)[C@H]1CC[C@H](C)CC1]

The compound was prepared following an analogous procedure to the one described for the synthesis of 2-methyl-2-{2-[3-(trans-4-methyl-cyclohexyl)-3-(4-phenyl-butyl)-ureido]-thiazol-5-ylsulfanyl}-propionic acid using 3-butyn-1-ol and (2-amino-thiazol-5-ylsulfanyl)-propionic acid ethyl ester.

$^1$H NMR (300 MHz, DMSO-d₆) ppm 12.02 (br. s, 1H), 7.42 (s, 1H), 3.96 (m, 1H), 3.48 (s, 2H), 3.42-3.31 (m, 2H), 2.89 (s, 1H), 2.48 (t, 2H), 1.72-1.45 (m, 6H), 1.42-1.18 (m, 2H), 1.12-0.98 (m, 2H), 0.85 (d, 3H)

HPLC-MS: m/z=382 (M+1)

Example 85

{2-[3-(Trans-4-methoxy-cyclohexyl)-3-phenethyl-ureido]-thiazol-5-ylsulfanyl}-acetic acid

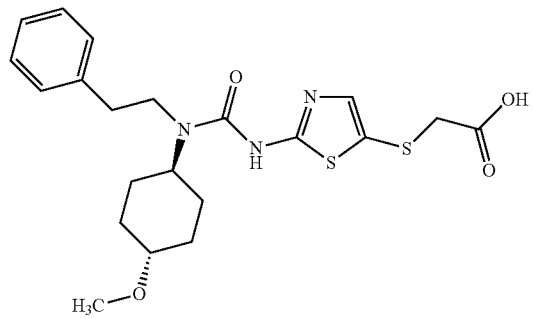 [SMILES: CO[C@H]1CC[C@H](N(CCc2ccccc2)C(=O)Nc2ncc(SCC(=O)O)s2)CC1]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using trans-4-methoxy-cyclohexylamine (prepared as described in J. Med. Chem. 1977, 20, 279-290), 2-phenylethylbromide and 2-aminothiazol-5-ylsulfanyl)acetic acid ethyl ester.

$^1$H NMR (300 MHz, CDCl₃) (ppm) 7.17-7.38 (m, 6H) 4.03 (br. s., 1H) 3.40-3.57 (m, 2H) 3.36 (s, 3H) 3.32 (s, 2H) 3.01-3.20 (m, 1H) 2.81-2.99 (m, 2H) 2.05-2.23 (m, 2H) 1.75-1.93 (m, 2H) 1.50-1.72 (m, 2H) 1.28-1.50 (m, 2H)

HPLC-MS: m/z=450 (M+1)

Example 86

{2-[3-(2-Benzyloxy-ethyl)-3-(trans-4-methoxy-cyclohexyl)-ureido]-thiazol-5-ylsulfanyl}-acetic acid

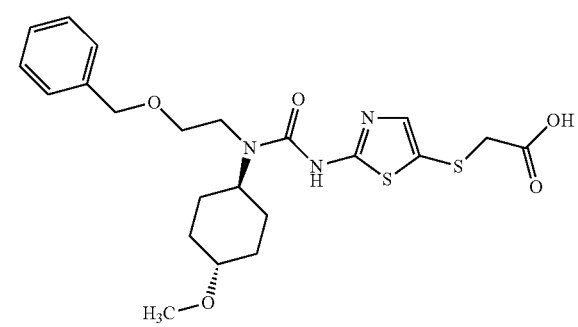 [SMILES: CO[C@H]1CC[C@H](N(CCOCc2ccccc2)C(=O)Nc2ncc(SCC(=O)O)s2)CC1]

The compound was prepared following an analogous procedure to the one described for the synthesis of 2-Methyl-2-{2-[3-(trans-4-methyl-cyclohexyl)-3-(4-phenyl-butyl)-ureido]-thiazol-5-ylsulfanyl}-propionic acid using trans-4-methoxy-cyclohexylamine, 2-benzyloxy-ethanol and 2-aminothiazol-5-ylsulfanyl)acetic acid ethyl ester.

$^1$H NMR (300 MHz, CDCl₃) (ppm) 10.50 (br. s., 1H) 7.11-7.47 (m, 6H) 4.57 (s, 2H) 4.02 (br. s., 1H) 3.55-3.66 (m, 2H) 3.45-3.55 (m, 2H) 3.35 (s, 2H) 3.33 (s, 3H) 2.99-3.14 (m, 1H) 2.10 (d, 2H) 1.79 (d, 2H) 1.44-1.66 (m, 2H) 1.24-1.44 (m, 2H)

HPLC-MS: m/z=480 (M+1)

Example 87

2-{2-[3-[2-(3-Chloro-phenyl)-ethyl]-3-(trans-4-methyl-cyclohexyl)-ureido]-thiazol-5-ylsulfanyl}-2-methyl-propionic acid

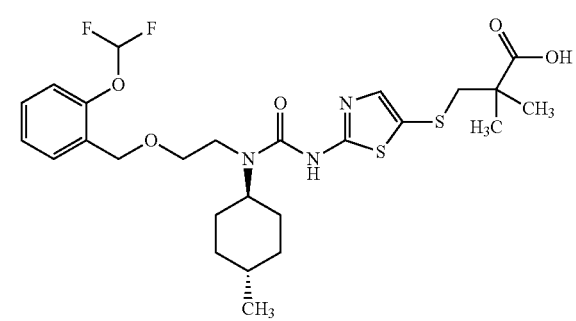 [SMILES: CC(C)(CSc1cnc(NC(=O)N(CCOCc2ccccc2OC(F)F)[C@H]2CC[C@H](C)CC2)s1)C(=O)O]

The compound was prepared following an analogous procedure to the one described for the synthesis of 3-{2-[3-[2-(2-Chloro-benzyloxy)-ethyl]-3-(trans-4-methyl-cyclohexyl)-ureido]-thiazol-5-ylsulfanyl}-2,2-dimethyl-propionic acid using 1-bromomethyl-2-difluoromethoxy-benzene and 3-(2-Amino-thiazol-5-ylsulfanyl)-2,2-dimethyl-propionic acid ethyl ester.

1H NMR (400 MHz, DMSO-d$_6$) (ppm) 7.48 (d, 1H) 7.29-7.40 (m, 2H) 7.12-7.27 (m, 2H) 4.55 (s, 2H) 3.82-4.00 (m, 1H) 3.42-3.63 (m, 5H) 2.95 (s, 2H) 1.63-1.76 (m, 2H) 1.45-1.61 (m, 4H) 1.23-1.40 (m, 1H) 1.17 (s, 6H) 0.95-1.09 (m, 2H) 0.86 (d, 3H)

HPLC-MS: m/z=572 (M+1)

Example 88

2-{2-[3-[2-(3-Chloro-phenyl)-ethyl]-3-(trans-4-methyl-cyclohexyl)-ureido]-thiazol-5-ylsulfanyl}-2-methyl-propionic acid

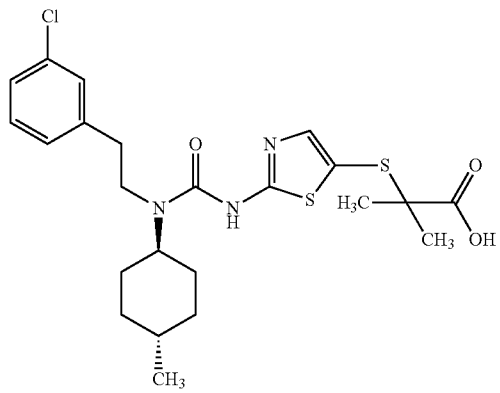 [SMILES: CC(C)(Sc1cnc(NC(=O)N(CCc2cccc(Cl)c2)[C@H]2CC[C@H](C)CC2)s1)C(=O)O]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 1-(2-bromo-ethyl)-3-chloro-benzene and 2-(2-amino-thiazol-5-ylsulfanyl)-2-methyl-propionic acid ethyl ester.

$^1$H NMR (400 MHz, DMSO-d$_6$) (ppm) 7.19-7.48 (m, 5H) 3.89-4.08 (m, 1H) 3.36-3.53 (m, 2H) 2.72-2.87 (m, 2H) 1.69 (d, 2H) 1.50-1.63 (m, 4H) 1.27-1.48 (m, 7H) 0.95-1.15 (m, 1H) 0.87 (d, 3H)

HPLC-MS: m/z=496 (M+1)

Example 89

2-{2-[3-[2-(3-Methoxy-phenyl)-ethyl]-3-(trans-4-methyl-cyclohexyl)-ureido]-thiazol-5-ylsulfanyl}-2-methyl-propionic acid

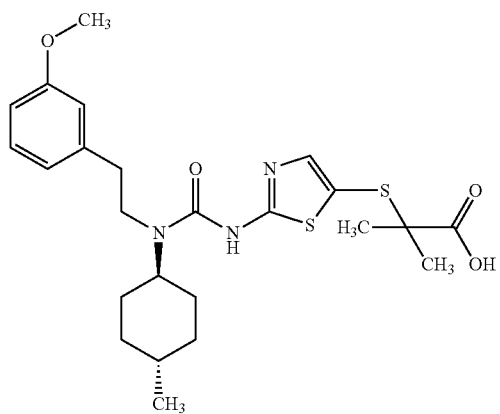 [SMILES: COc1cccc(CCN(C(=O)Nc2ncc(SC(C)(C)C(=O)O)s2)[C@H]2CC[C@H](C)CC2)c1]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 1-(2-bromo-ethyl)-3-methoxy-benzene and 2-(2-amino-thiazol-5-ylsulfanyl)-2-methyl-propionic acid ethyl ester.

$^1$H NMR (400 MHz, DMSO-d$_6$) (ppm) 7.41 (s, 1H) 7.22 (t, 1H) 6.72-6.93 (m, 3H) 3.91-4.06 (m, 1H) 3.75 (s, 3H) 3.36-3.48 (m, 2H) 2.70-2.82 (m, 2H) 1.69 (d, 2H) 1.49-1.63 (m, 4H) 1.26-1.47 (m, 7H) 0.98-1.14 (m, 2H) 0.87 (d, 3H)

Example 90

2-{2-[3-[2-(3,4-Dimethoxy-phenyl)-ethyl]-3-(trans-4-methyl-cyclohexyl)-ureido]-thiazol-5-ylsulfanyl}-2-methyl-propionic acid

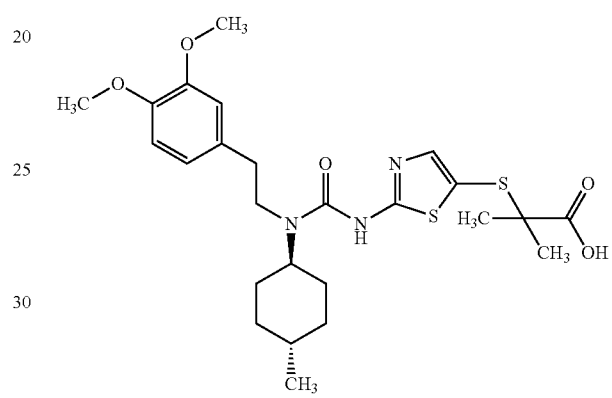

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 1-(2-bromo-ethyl)-3,4-dimethoxy-benzene and 2-(2-amino-thiazol-5-ylsulfanyl)-2-methyl-propionic acid ethyl ester.

$^1$H NMR (400 MHz, DMSO-d$_6$) (ppm) 7.41 (s, 1H) 6.82-6.91 (m, 2H) 6.74-6.82 (m, 1H) 3.91-4.06 (m, 1H) 3.76 (s, 3H) 3.71 (s, 3H) 3.34-3.53 (m, 2H) 2.66-2.77 (m, 2H) 1.69 (d, 2H) 1.50-1.64 (m, 4H) 1.24-1.47 (m, 7H) 0.98-1.14 (m, 2H) 0.87 (d, 3H)

Example 91

{2-[3-(2-Cyano-ethyl)-3-(trans-4-methyl-cyclohexyl)-ureido]-thiazol-5-ylsulfanyl}-acetic acid

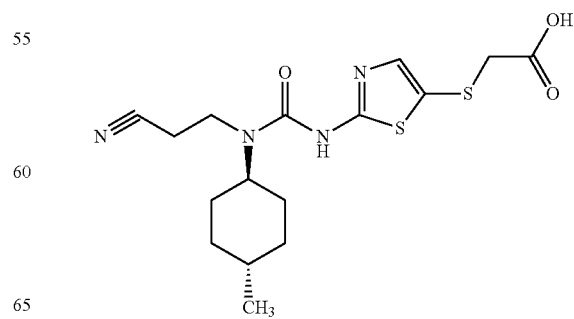

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 3-bromopropionitrile and 2-aminothiazol-5-ylsulfanyl)acetic acid ethyl ester.

$^1$H NMR (400 MHz, DMSO-d$_6$) (ppm) 11.99 (br. s, 1H) 7.41 (s, 1H) 4.15-3.89 (m, 1H) 3.61-3.40 (m, 5H) 2.70 (t, 2H) 1.80-1.47 (m, 6H) 1.42-1.20 (m, 1H) 1.14-0.93 (m, 2H) 0.85 (d, 3H)

HPLC-MS: m/z=383 (M+1)

Example 92

{2-[3-(trans-4-Methyl-cyclohexyl)-3-pyridin-4-ylmethyl-ureido]-thiazol-5-ylsulfanyl}-acetic acid

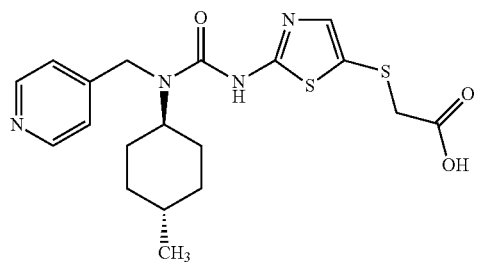 [SMILES: C[C@H]1CC[C@H](N(Cc2ccncc2)C(=O)Nc2ncc(SCC(=O)O)s2)CC1]

A mixture of 4-formylpyridine (0.88 g, 8.25 mmol), trans-4-methyl-cyclohexylamine hydrochloride (0.93 g, 8.25 mmol) and NaBH$_3$CN (1.3 g, 20.6 mmol) in MeOH (50 mL) and AcOH (1.5 mL) was refluxed for 1.5 h. The heating was discontinued and the reaction mixture was left at rt for 2 days. The volatiles were removed in vacuo and the residue was divided between aqueous NaHCO$_3$ and DCM. The DCM phase was concentrated in vacuo. Purification on preparative HPLC gave the TFA salt of (4-methyl-cyclohexyl)-pyridin-4-ylmethyl-amine. The amine was coupled and hydrolyses using the procedure described in the procedure for the preparation of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 2-aminothiazol-5-ylsulfanyl)acetic acid ethyl ester $^1$H NMR (400 MHz, DMSO-d$_6$) (ppm) 8.47 (d, 2H) 7.40 (s, 1H) 7.20 (d, 2H) 4.59 (s, 4.13-4.25 (m, 1H) 3.48 (s, 2H) 1.52-1.69 (m, 4H) 1.34-1.49 (m, 2H) 1.20-1.33 (m, 1H) 0.97-1.12 (m, 2H) 0.84 (d, 3H)

HPLC-MS: m/z=421 (M+1)

Example 93

{2-[3-(trans-4-Methyl-cyclohexyl)-3-pyridin-2-ylmethyl-ureido]-thiazol-5-ylsulfanyl}-acetic acid

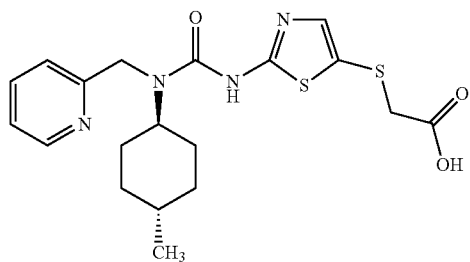 [SMILES: C[C@H]1CC[C@H](N(Cc2ccccn2)C(=O)Nc2ncc(SCC(=O)O)s2)CC1]

The compound was prepared following an analogous procedure to the one described for the synthesis of {2-[3-(trans-4-methyl-cyclohexyl)-3-pyridin-4-ylmethyl-ureido]-thiazol-5-ylsulfanyl}-acetic acid using 2-formyl-pyridine.

$^1$H NMR (400 MHz, CDCl$_3$) (ppm) 8.60 (d, 1H) 7.70 (dd, 1H) 7.40 (s, 1H) 7.30 (d, 1H) 7.24 (dd, 1H) 4.58 (br. s., 2H) 4.09-4.21 (m, 1H) 3.33 (s, 2H) 1.67-1.76 (m, 4H) 1.41-1.54 (m, 2H) 1.26-1.37 (m, 1H) 1.06-1.18 (m, 2H) 0.88 (d, 3H)

HPLC-MS: m/z=421 (M+1

Example 94

{2-[3-(trans-4-Methyl-cyclohexyl)-3-pyridin-3-ylmethyl-ureido]-thiazol-5-ylsulfanyl}-acetic acid

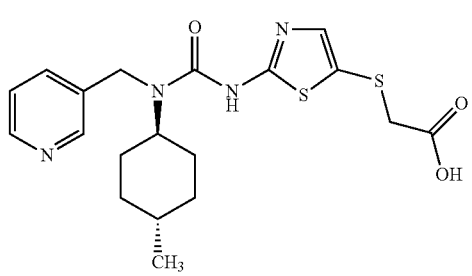 [SMILES: C[C@H]1CC[C@H](N(Cc2cccnc2)C(=O)Nc2ncc(SCC(=O)O)s2)CC1]

The compound was prepared following an analogous procedure to the one described for the synthesis of {2-[3-(trans-4-Methyl-cyclohexyl)-3-pyridin-4-ylmethyl-ureido]-thiazol-5-ylsulfanyl}-acetic acid using 3-formyl-pyridine.

$^1$H NMR (400 MHz, DMSO-d$_6$) (ppm) 8.46 (d, 1H) 8.41 (dd, 1 □H) 7.59 (d, 1H) 7.39 (s, 1H) 7.32 (dd, 1H) 4.60 (s., 2H) 4.11-4.19 (m, 1H) 3.48 (s, 2H) 1.61-1.68 (m, 2H) 1.40-1.57□ (m, 4H) 1.23-1.33 (m, 1H) 0.99-1.10 (m, 2H) 0.84 (d, 3H)

HPLC-MS: m/z=421 (M+1)

Example 95

{2-[3-[4-(4-Methanesulfonyl-phenyl)-but-3-ynyl]-3-(trans-4-methyl-cyclohexyl)-ureido]-thiazol-5-ylsulfanyl}-acetic acid

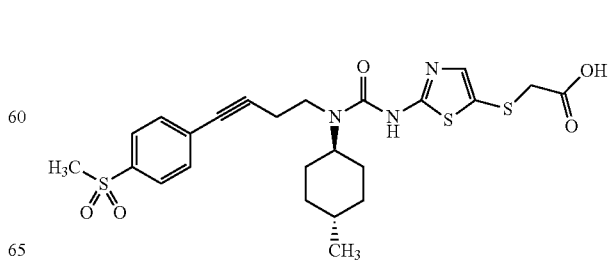

To solution of but-3-ynol (3.57 g, 51 mmol) in DCM (260 mL) cooled to −10° C. was added TEA (11.1 mL, 80 mmol) followed by methane sulphonyl chloride (6.41 g, 56 mmol) and the resulting reaction mixture stirred for 15 min at 0° C. and 1 h at room temperature. Water (30 mL) was added and the organics were separated, washed with 1N HCl (30 mL), saturated NaHCO₃ (30 mL), brine (30 mL) dried (MgSO₄), filtered and concentrated in vacuo to yield the corresponding mesylate as an oil. This was dissolved in DMSO (40 mL) followed by the addition of sodium iodide (200 mg) and 4-trans-methyl-cyclohexylamine (7.63 g, 51 mmol). The mixture was stirred at 50° C. for 5 h then poured onto 1% NaOH solution (200 mL). The organics were extracted with diethyl ether (3×100 mL) and the combined solvents were dried (MgSO₄), filtered and concentrated in vacuo. The oily residue was dissolved in ethyl acetate (20 mL) followed by the addition of ethyl acetate saturated with HCl (5 mL). The resulting precipitate was filtered and washed with ethyl acetate and dried in vacuo to yield the crude but-3-ynyl-(trans-4-methyl-cyclohexyl)-amine hydrochloride which was used without further purification.

To a portion of the above but-3-ynyl-(trans-4-methyl-cyclohexyl)-amine hydrochloride (500 mg, 2.48 mmol) dissolved in pyrrolidine (2.5 mL) was added 1-bromo-4-methanesulfonyl-benzene (583 mg, 2.48 mmol) and the solution was degassed by bubbling nitrogen through for 10 min. Tetrakis(triphenylphosphine)palladium(0) (28 mg, 0.025 mmol) was added and the mixture was heated at 50° C. for 16 h before the volatiles were removed by evaporation and the residue purified by HPLC to yield the intermediate [4-(4-methanesulfonyl-phenyl)-but-3-ynyl]-(trans-4-methyl-cyclohexyl)-amine.

The amine was coupled and the resulting ester hydrolyzed as previously described for the synthesis of {2-[3-[3-(3-Chloro-phenyl)-propyl]-3-(trans-4-methyl-cyclohexyl)-ureido]-thiazol-5-ylsulfanyl}-acetic acid.

¹H NMR (300 MHz, DMSO-d₆) (ppm) 7.88 (d, 2H), 7.69 (d, 2H), 7.40 (s, 1H), 4.05-3.91 (m, 1H), 3.60-3.28 (m, 5H), 3.23 (s, 3H), 2.77-2.65 (m, 2H), 1.77-1.53 (m, 6H), 1.44-1.28 (m, 1H), 1.18-0.98 (m, 2H), 0.87 (d, 3H)

HPLC-MS: m/z=536 (M+1)

Example 96

{2-[3-(trans-4-Methyl-cyclohexyl)-3-(4-phenyl-but-3-ynyl)-ureido]-thiazol-5-ylsulfanyl}-acetic acid

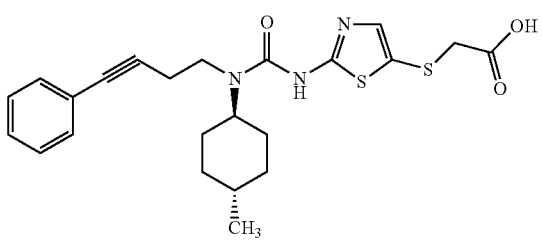 [SMILES: C[C@H]1CC[C@H](N(CCC#Cc2ccccc2)C(=O)Nc2ncc(SCC(=O)O)s2)CC1]

The compound was prepared following an analogous procedure to the one described for the synthesis of {2-[3-[4-(4-Methanesulfonyl-phenyl)-but-3-ynyl]-3-(trans-4-methyl-cyclohexyl)-ureido]-thiazol-5-ylsulfanyl}-acetic acid using bromobenzene.

¹H NMR (300 MHz, DMSO-d₆) (ppm) 7.46-7.31 (m, 6H), 4.07-3.90 (m, 1H), 3.59-3.42 (m, 4H), 2.69-2.59 (m, 2H), 1.78-1.51 (m, 6H), 1.44-1.28 (m, 1H), 1.14-0.96 (m, 2H), 0.87 (d, 3H)

HPLC-MS: m/z=458 (M+1)

Example 97

1-{2-[3-[2-(2-Chloro-benzyloxy)-ethyl]-3-(trans-4-methyl-cyclohexyl)-ureido]-thiazol-5-ylsulfanyl}-cyclobutanecarboxylic acid

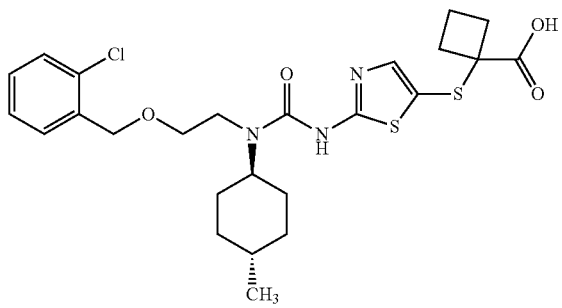 [SMILES: C[C@H]1CC[C@H](N(CCOCc2ccccc2Cl)C(=O)Nc2ncc(SC3(C(=O)O)CCC3)s2)CC1]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 1-(2-amino-thiazol-5-ylsulfanyl)-cyclobutanecarboxylic acid prepared using the procedure for the preparation of 2-(2-amino-thiazol-5-ylsulfanyl)-2-methyl-propionic acid ethyl ester.

¹H NMR (400 MHz, DMSO-d₆) (ppm) 7.47-7.58 (m, 1H) 7.38-7.46 (m, 2H) 7.22-7.37 (m, 2H) 4.60 (s, 2H) 3.83-4.01 (m, 1H) 3.61 (t, 2H) 3.43-3.57 (m, 2H) 1.94-2.17 (m, 3H) 1.73-1.85 (m, 1H) 1.63-1.72 (m, 2H) 1.44-1.61 (m, 4H) 1.24-1.39 (m, 1H) 0.94-1.12 (m, 2H) 0.86 (d, 3H)

HPLC-MS: m/z=538 (M+1)

Example 98

1-{2-[3-[2-(2-Chloro-benzyloxy)-ethyl]-3-(trans-4-methyl-cyclohexyl)-ureido]-thiazol-5-ylsulfanyl}-cyclohexanecarboxylic acid

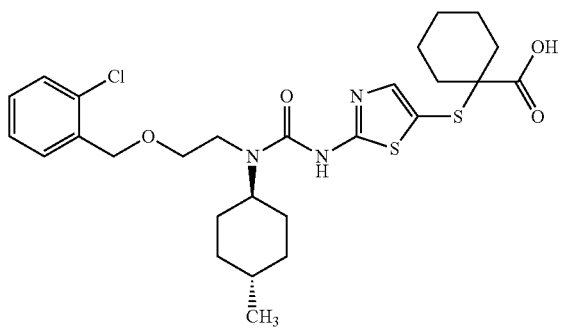 [SMILES: C[C@H]1CC[C@H](N(CCOCc2ccccc2Cl)C(=O)Nc2ncc(SC3(C(=O)O)CCCCC3)s2)CC1]

The compound was prepared following an analogous procedure to the one described for the synthesis of 3-{2-[3-[2-(2-Chloro-benzyloxy)-ethyl]-3-(trans-4-methyl-cyclohexyl)-ureido]-thiazol-5-ylsulfanyl}-2,2-dimethyl-propionic acid using 1-(2-Amino-thiazol-5-ylsulfanyl)-cyclohexanecarboxylic acid prepared using the procedure for the preparation of 2-(2-amino-thiazol-5-ylsulfanyl)-2-methyl-propionic acid ethyl ester.

¹H NMR (400 MHz, DMSO-d₆) (ppm) 7.47-7.56 (m, 1H) 7.38-7.47 (m, 1H) 7.21-7.36 (m, 3H) 4.60 (s, 2H) 3.85-4.02 (m, 1H) 3.56-3.66 (m, 2H) 3.47-3.55 (m, 2H) 1.92-2.11 (m, 2H) 1.62-1.76 (m, 4H) 1.40-1.61 (m, 7H) 1.19-1.35 (m, 4H) 0.94-1.11 (m, 2H) 0.86 (d, 3H)

HPLC-MS: m/z=566 (M+1)

Example 99

1-{2-[3-(trans-4-Methyl-cyclohexyl)-3-(4-phenyl-butyl)-ureido]-thiazol-5-ylsulfanyl}-cyclobutanecarboxylic acid

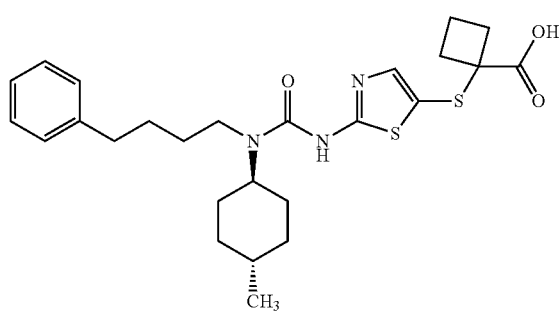 [SMILES: C[C@H]1CC[C@H](N(CCCCc2ccccc2)C(=O)Nc2ncc(SC3(C(=O)O)CCC3)s2)CC1]

The compound was prepared following an analogous procedure to the one described for the synthesis of 2-Methyl-2-{2-[3-(trans-4-methyl-cyclohexyl)-3-(4-phenyl-butyl)-ureido]-thiazol-5-ylsulfanyl}-propionic acid using 1-(2-amino-thiazol-5-ylsulfanyl)cyclobutanecarboxylic acid ethyl ester prepared using the procedure for the preparation of 2-(2-amino-thiazol-5-ylsulfanyl)-2-methyl-propionic acid ethyl ester.

¹H NMR (400 MHz, DMSO-d₆) (ppm) 7.45 (s, 1H) 7.23-7.33 (m, 2H) 7.08-7.23 (m, 3H) 3.84-4.00 (m, 1H) 3.13-3.27 (m, 2H) 2.59 (t, 2H) 1.95-2.17 (m, 3H) 1.72-1.86 (m, 1H) 1.62-1.72 (m, 2H) 1.40-1.62 (m, 8H) 1.24-1.39 (m, 1H) 0.92-1.12 (m, 2H) 0.86 (d, 3H)

HPLC-MS: m/z=502 (M+1)

Example 100

1-{2-[3-(trans-4-Methyl-cyclohexyl)-3-(4-phenyl-butyl)-ureido]-thiazol-5-ylsulfanyl}-cyclohexanecarboxylic acid

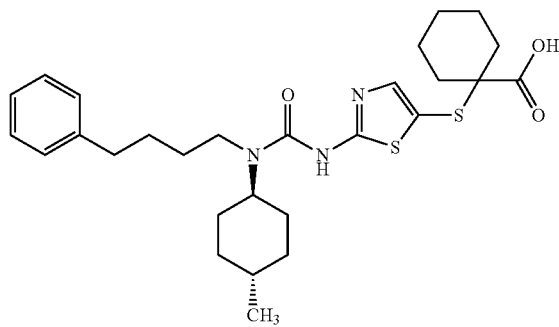 [SMILES: C[C@H]1CC[C@H](N(CCCCc2ccccc2)C(=O)Nc2ncc(SC3(C(=O)O)CCCCC3)s2)CC1]

The compound was prepared following an analogous procedure to the one described for the synthesis of 2-Methyl-2-{2-[3-(trans-4-methyl-cyclohexyl)-3-(4-phenyl-butyl)-ureido]-thiazol-5-ylsulfanyl}-propionic acid using 1-(2-amino-thiazol-5-ylsulfanyl)-cyclohexanecarboxylic acid methyl ester prepared using the procedure for the preparation of 2-(2-amino-thiazol-5-ylsulfanyl)-2-methyl-propionic acid ethyl ester.

¹H NMR (400 MHz, DMSO-d₆) (ppm) 7.35 (s, 1H) 7.23-7.30 (m, 2H) 7.06-7.24 (m, 3H) 3.75-4.10 (m, 1H) 3.11-3.28 (m, 2H) 2.59 (t, 2H) 1.88-2.10 (m, 2H) 1.62-1.76 (m, 4H) 1.39-1.62 (m, 11H) 1.17-1.37 (m, 4H) 1.04 (q, 2H) 0.86 (d, 3H)

HPLC-MS: m/z=530 (M+1)

Example 101

1-{2-[3-[2-(trans-4-Methoxy-phenyl)-ethyl]-3-(4-methyl-cyclohexyl)-ureido]-thiazol-5-ylsulfanyl}-cyclobutanecarboxylic acid

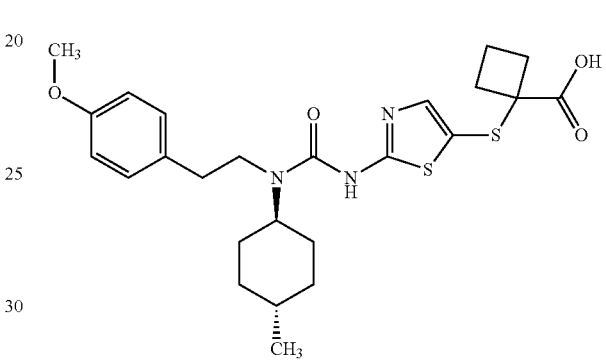

The compound was prepared following an analogous procedure to the one described for the synthesis of 2-methyl-2-{2-[3-(trans-4-methyl-cyclohexyl)-3-(4-phenyl-butyl)-ureido]-thiazol-5-ylsulfanyl}-propionic acid using 2-(4-methoxyphenyl)-ethanol and 1-(2-amino-thiazol-5-ylsulfanyl)-cyclobutanecarboxylic acid ethyl ester prepared using the procedure for the preparation of 2-(2-amino-thiazol-5-ylsulfanyl)-2-methyl-propionic acid ethyl ester.

¹H NMR (400 MHz, DMSO-d₆) (ppm) 7.47 (s, 1H) 7.20 (d, 2H) 6.87 (d, 2H) 3.81-4.14 (m, 1H) 3.72 (s, 3H) 2.58-2.88 (m, 2H) 1.93-2.18 (m, 3H) 1.74-1.89 (m, 1H) 1.69 (d, 2H) 1.45-1.63 (m, 4H) 1.25-1.41 (m, 1H) 0.96-1.14 (m, 2H) 0.87 (d, 3H)

HPLC-MS: m/z=504 (M+1)

Example 102

1-{2-[3-[2-(4-Methoxy-phenyl)-ethyl]-3-(trans-4-methyl-cyclohexyl)-ureido]-thiazol-5-ylsulfanyl}-cyclohexanecarboxylic acid

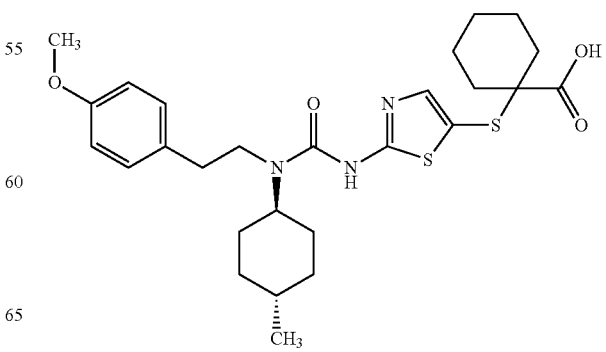

The compound was prepared following an analogous procedure to the one described for the synthesis of 2-methyl-2-{2-[3-(trans-4-methyl-cyclohexyl)-3-(4-phenyl-butyl)-ureido]-thiazol-5-ylsulfanyl}-propionic acid using 2-(4-methoxyphenyl)-ethanol and 1-(2-amino-thiazol-5-ylsulfanyl)-cyclohexanecarboxylic acid methyl ester prepared using the procedure for the preparation of 2-(2-amino-thiazol-5-ylsulfanyl)-2-methyl-propionic acid ethyl ester.

$^1$H NMR (400 MHz, DMSO-d$_6$) (ppm) 7.36 (s, 1H) 7.20 (d, 2H) 6.87 (d, 2H) 3.83-4.12 (m, 1H) 3.72 (s, 3H) 2.60-2.83 (m, 2H) 1.88-2.13 (m, 2H) 1.63-1.79 (m, 4H) 1.41-1.62 (m, 7H) 1.18-1.39 (m, 4H) 0.96-1.15 (m, 2H) 0.87 (d, 3H)
HPLC-MS: m/z=532 (M+1)

Example 103

2-{2-[3-[2-(4-Fluoro-phenyl)-ethyl]-3-(trans-4-methyl-cyclohexyl)-ureido]-thiazol-5-ylsulfanyl}-2-methyl-propionic acid

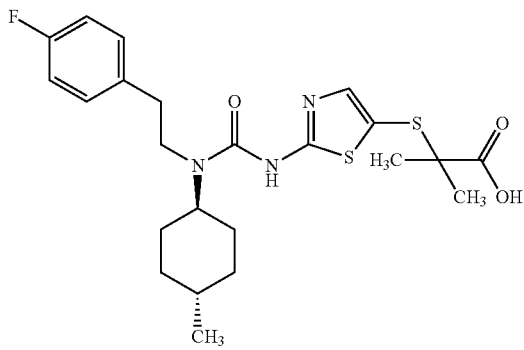 [SMILES: CC(C)(Sc1cnc(NC(=O)N(CCc2ccc(F)cc2)[C@H]2CC[C@H](C)CC2)s1)C(=O)O]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 2-(4-fluorophenyl)ethylbromide and 2-(2-amino-thiazol-5-ylsulfanyl)-2-methyl-propionic acid ethyl ester.

$^1$H NMR (400 MHz, DMSO-d$_6$) (ppm) 7.41 (s, 1H) 7.32 (t, 2H) 7.12 (t, 2H) 3.91-4.07 (m, 1H) 3.34-3.49 (m, 2H) 2.78 (t, 2H) 1.69 (d, 2H) 1.49-1.63 (m, 4H) 1.27-1.46 (m, 7H) 0.98-1.14 (m, 2H) 0.87 (d, 3H)
HPLC-MS: m/z=480

Example 104

2-{2-[3-[2-(2,3-Dihydro-benzofuran-6-yl)-ethyl]-3-(trans-4-methyl-cyclohexyl)-ureido]-thiazol-5-ylsulfanyl}-2-methyl-propionic acid

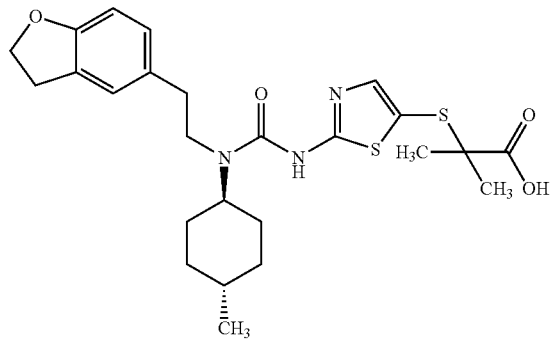 [SMILES: CC(C)(Sc1cnc(NC(=O)N(CCc2ccc3c(c2)CCO3)[C@H]2CC[C@H](C)CC2)s1)C(=O)O]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 5-(2-bromo-ethyl)-2,3-dihydro-benzofuran and 2-(2-amino-thiazol-5-ylsulfanyl)-2-methyl-propionic acid ethyl ester.

$^1$H NMR (400 MHz, DMSO-d$_6$) (ppm) 7.41 (s, 1H) 7.16 (s, 1H) 6.98 (d, 1H) 6.69 (d, 1H) 4.48 (t, 2H) 3.86-4.10 (m, 1H) 3.14 (t, 2H) 2.62-2.74 (m, 2H) 1.64-1.73 (m, 2H) 1.49-1.64 (m, 4H) 1.26-1.48 (m, 7H) 0.97-1.16 (m, 2H) 0.87 (d, 3H)
HPLC-MS: m/z=504 (M+1)

Example 105

2-{2-[3-[2-(3-Fluoro-phenyl)-ethyl]-3-(trans-4-methyl-cyclohexyl)-ureido]-thiazol-5-ylsulfanyl}-2-methyl-propionic acid

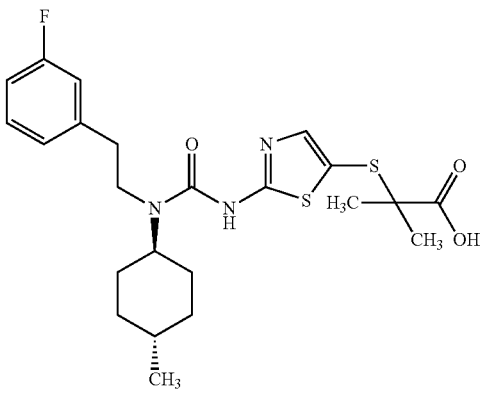 [SMILES: CC(C)(Sc1cnc(NC(=O)N(CCc2cccc(F)c2)[C@H]2CC[C@H](C)CC2)s1)C(=O)O]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 2-(3-fluorophenyl)ethylbromide and 2-(2-amino-thiazol-5-ylsulfanyl)-2-methyl-propionic acid ethyl ester.

$^1$H NMR (400 MHz, DMSO-d$_6$) (ppm) 7.41 (s, 1H) 7.34 (q, 1H) 7.09-7.20 (m, 2H) 6.99-7.09 (m, 1H) 3.90-4.06 (m, 1H) 3.39-3.50 (m, 2H) 2.75-2.86 (m, 2H) 1.62-1.75 (m, 2H) 1.52-1.63 (m, 4H) 1.28-1.45 (m, 7H) 0.96-1.13 (m, 2H) 0.87 (d, 3H)H) 0.97-1.16 (m, 2H) 0.87 (d, 3H)
HPLC-MS: m/z=480 (M+1)

Example 106

2-{2-[3-(2-1,3-Benzodioxol-5-yl-ethyl)-3-(trans-4-methyl-cyclohexyl)-ureido]-thiazol-5-ylsulfanyl}-2-methyl-propionic acid

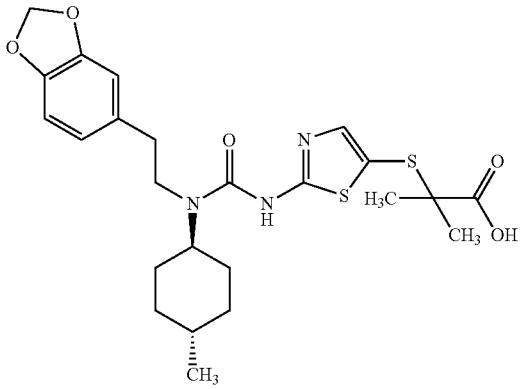 [SMILES: CC(C)(Sc1cnc(NC(=O)N(CCc2ccc3c(c2)OCO3)[C@H]2CC[C@H](C)CC2)s1)C(=O)O]

The compound was prepared following an analogous procedure to the one described for the synthesis of 2-methyl-2-{2-[3-(trans-4-methyl-cyclohexyl)-3-phenethyl-ureido]-thiazol-5-ylsulfanyl}-propionic acid using 5-(2-bromoethyl)benzo[1,3]dioxole and 2-(2-amino-thiazol-5-ylsulfanyl)-2-methyl-propionic acid ethyl ester.

$^1$H NMR (400 MHz, DMSO-d$_6$) (ppm) 7.41 (s, 1H) 6.91 (br. s., 1H) 6.79-6.86 (m, 1H) 6.73 (d, 1H) 5.97 (s, 2H) 3.91-4.05 (m, 1H) 2.62-2.76 (m, 2H) 1.69 (d, 2H) 1.52-1.63 (m, 4H) 1.28-1.45 (m, 7H) 0.99-1.13 (m, 2H) 0.87 (d, 3H)

HPLC-MS: m/z=506 (M+1)

Example 107

(2-{3-(trans-4-Methyl-cyclohexyl)-3-[2-(pyridin-3-ylmethoxy)-ethyl]-ureido}-thiazol-5-ylsulfanyl)-acetic acid

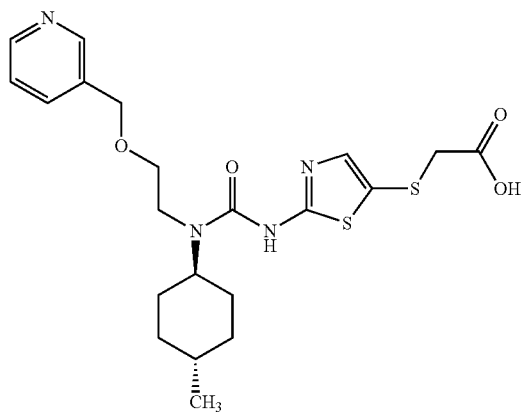 [SMILES: C[C@H]1CC[C@H](N(CCOCc2cccnc2)C(=O)Nc2ncc(SCC(=O)O)s2)CC1]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 3-bromomethylpyridine hydrobromide and (2-amino-thiazol-5-ylsulfanyl)acetic acid ethyl ester.

$^1$H NMR (300 MHz, DMSO-d$_6$) (ppm) 8.91 (s, 1H), 8.87 (d, 1H), 8.55 (d, 1H), 8.05 (dd, 1H), 7.42 (s, 1H), 4.76 (s, 2H), 3.87-4.04 (m, 1H), 3.60-3.71 (m, 2H), 3.46-3.59 (m, 4H), 1.46-1.76 (m, 6H), 1.22-1.41 (m, 1H), 0.96-1.13 (m, 2H), 0.87 (d, 3H)

HPLC-MS: m/z=465 (M+H)

Example 108

(2-{3-(trans-4-Methyl-cyclohexyl)-3-[2-(pyridin-2-ylmethoxy)-ethyl]-ureido}-thiazol-5-ylsulfanyl)-acetic acid

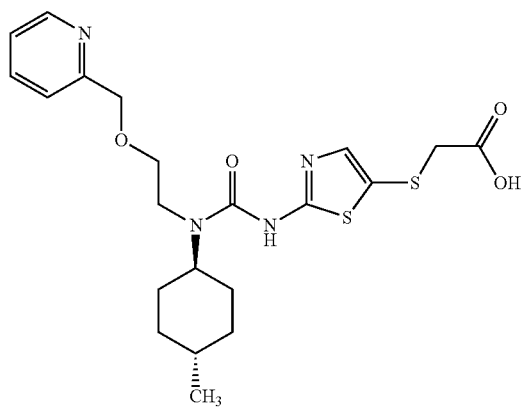 [SMILES: C[C@H]1CC[C@H](N(CCOCc2ccccn2)C(=O)Nc2ncc(SCC(=O)O)s2)CC1]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 2-bromomethylpyridine hydrobromide and (2-amino-thiazol-5-ylsulfanyl)acetic acid ethyl ester.

$^1$H NMR (300 MHz, DMSO-d$_6$) (ppm) 8.82 (d, 1H), 8.47 (t, 1H), 7.97 (d, 1H), 7.90 (t, 1H), 7.40 (s, 1H), 4.91 (s, 2H), 3.89-4.04 (m, 1H), 3.63-3.73 (m, 2H), 3.52-3.61 (m, 2H), 3.49 (s, 2H), 1.44-1.77 (m, 6H), 1.20-1.42 (m, 1H), 0.93-1.15 (m, 2H), 0.87 (d, 3H)

HPLC-MS: m/z=465 (M+H)

Example 109

(2-{3-(trans-4-Methyl-cyclohexyl)-3-[2-(pyridin-4-ylmethoxy)-ethyl]-ureido}-thiazol-5-ylsulfanyl)-acetic acid

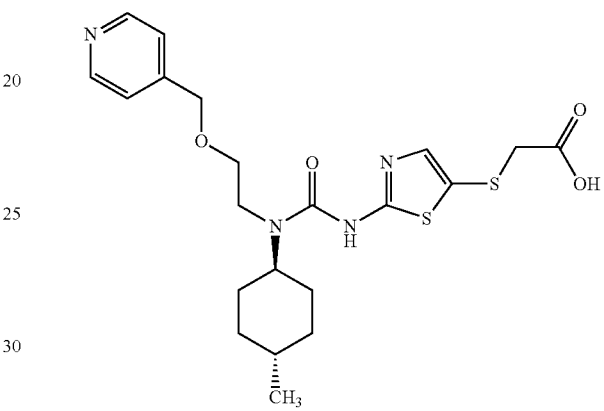

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 4-bromomethylpyridine hydrobromide and (2-amino-thiazol-5-ylsulfanyl)acetic acid ethyl ester.

$^1$H NMR (300 MHz, DMSO-d$_6$) (ppm) 8.51 (d, 2H), 7.41 (s, 1H), 7.33 (d, 2H), 4.58 (s, 2H), 3.87-4.02 (m, 1H), 3.55 (m, 4H), 3.49 (s, 2H), 1.45-1.77 (m, 6H), 1.21-1.41 (m, 1H), 0.94-1.14 (m, 2H), 0.86 (d, 3H)

HPLC-MS: m/z=465 (M+H)

Example 110

{2-[3-(2-Cyclopropylmethoxy-ethyl)-3-(trans-4-methyl-cyclohexyl)-ureido]-thiazol-5-ylsulfanyl}-acetic acid

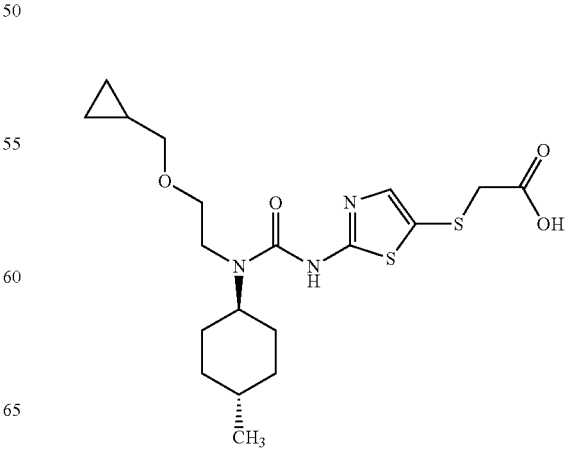

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using bromomethyl-cyclopropane and (2-aminothiazol-5-ylsulfanyl)acetic acid ethyl ester.

$^1$H NMR (300 MHz, DMSO-d$_6$) (ppm) 7.40 (s, 1H), 3.84-4.01 (m, 1H), 3.47-3.57 (m, 2H), 3.32-3.46 (m, 4H), 3.29 (d, 2H), 1.45-1.79 (m, 6H), 1.21-1.43 (m, 1H), 0.93-1.14 (m, 3H), 0.87 (d, 3H), 0.38-0.50 (m, 2H), 0.12-0.21 (m, 2H)

HPLC-MS: m/z=428 (M+H)

Example 111

{2-[3-[2-(5-Chloro-benzo[b]thiophen-3-ylmethoxy)-ethyl]-3-(trans-4-methyl-cyclohexyl)-ureido]-thiazol-5-ylsulfanyl}-acetic acid

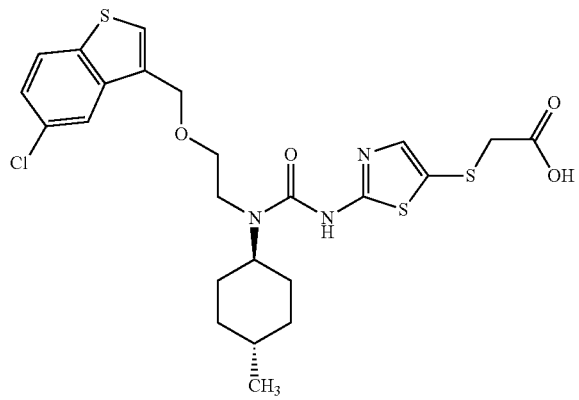 [SMILES: C[C@H]1CC[C@H](N(CCOCc2csc3ccc(Cl)cc23)C(=O)Nc2ncc(SCC(=O)O)s2)CC1]

The compound was prepared following an analogous procedure to the one described for the synthesis of 3-{2-[3-[2-(2-chloro-benzyloxy)-ethyl]-3-(trans-4-methyl-cyclohexyl)-ureido]-thiazol-5-ylsulfanyl}-2,2-dimethyl-propionic acid using 3-bromomethyl-5-chloro-benzo[b]thiophene and (2-aminothiazol-5-ylsulfanyl)acetic acid ethyl ester.

$^1$H NMR (300 MHz, DMSO-d$_6$) (ppm) 7.99-8.08 (m, 1H), 7.89 (d, 1H), 7.82 (s, 1H), 7.34-7.45 (m, 2H), 4.77 (s, 2H), 3.81-3.98 (m, 1H), 3.58 (t, 2H), 3.43-3.51 (m, 4H), 1.37-1.70 (m, 6H), 1.16-1.34 (m, 1H), 0.90-1.09 (m, 2H), 0.84 (d, 3H)

HPLC-MS: m/z=554 (M+H)

Example 112

{2-[3-(trans-4-Methyl-cyclohexyl)-3-(5-phenyl-pentyl)-ureido]-thiazol-5-ylsulfanyl}-acetic acid

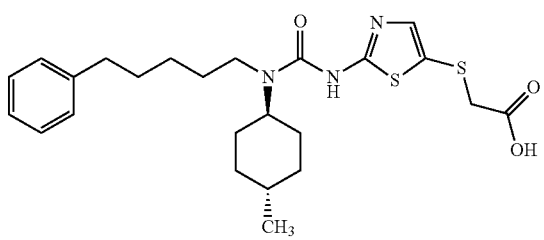 [SMILES: C[C@H]1CC[C@H](N(CCCCCc2ccccc2)C(=O)Nc2ncc(SCC(=O)O)s2)CC1]

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 5-phenyl-pentanoic acid and (2-aminothiazol-5-ylsulfanyl)acetic acid ethyl ester.

$^1$H NMR (400 MHz, DMSO-d$_6$) (ppm) 7.40 (s, 1H) 7.23-7.29 (m, 2H) 7.13-7.21 (m, 3H) 3.89-3.99 (m, 1H) 3.47 (s, 2H) 3.18 (t, 2H) 2.57 (t, 2H) 1.68 (d, 2H) 1.43-1.62 (m, 8H) 1.22-1.36 (m, 3H) 0.98-1.11 (m, 2H) 0.86 (d, 3H)

Example 113

2-{2-[3-[3-(3-Methoxy-phenyl)-propyl]-3-(trans-4-methyl-cyclohexyl)-ureido]-thiazol-5-ylsulfanyl}-2-methyl-propionic acid

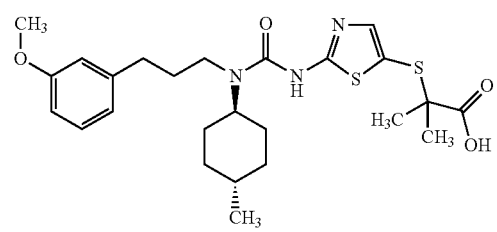 [SMILES: COc1cccc(CCCN(C(=O)Nc2ncc(SC(C)(C)C(=O)O)s2)[C@H]2CC[C@H](C)CC2)c1]

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 3-(3-methoxy-phenyl)-propionic acid and 2-(2-amino-thiazol-5-ylsulfanyl)-2-methyl-propionic acid ethyl ester.

HPLC-MS: m/z=476 (M+H)

$^1$H NMR (400 MHz, DMSO-d6) (ppm) 7.36 (s, 1H) 7.15 (t, 1H) 6.64-6.79 (m, 3H) 3.84-4.00 (m, 1H) 3.69 (s, 3H) 3.14-3.25 (m, 2H) 2.48-2.58 (m, 2H) 1.67-1.79 (m, 2H) 1.63 (d, 2H) 1.49-1.59 (m, 2H) 1.29-1.49 (m, 8H) 1.14-1.30 (m, 1H) 0.91-1.07 (m, 2H) 0.82 (d, 3H)

HPLC-MS: m/z=506 (M+H)

Example 114

2-{2-[3-[3-(3-Chloro-phenyl)-propyl]-3-(trans-4-methyl-cyclohexyl)-ureido]-thiazol-5-ylsulfanyl}-2-methyl-propionic acid

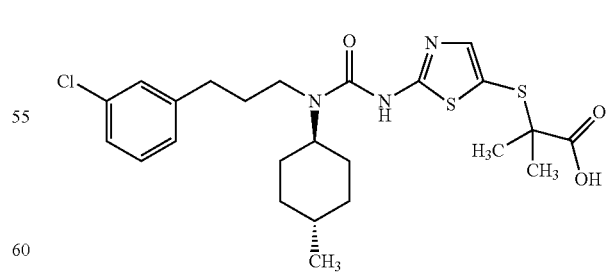

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 2-(2-amino-thiazol-5-ylsulfanyl)-2-methyl-propionic acid ethyl ester.

¹H NMR (300 MHz, DMSO-d₆) (ppm) 12.02 (br.s., 1H), 7.42 (s, 1H), 7.35-7.10 (m, 4H), 3.96 (br.s., 1H), 3.48 (s, 2H), 3.24 (br.s., 2H), 2.58 (t, 2H), 1.90-1.15 (m, 10H), 1.06 (br.s., 2H), 0.85 (d, 3H)

HPLC-MS: m/z=482 (M+H)

Example 115

2-{2-[3-[3-(4-Fluoro-phenyl)-propyl]-3-(trans-4-methyl-cyclohexyl)-ureido]-thiazol-5-ylsulfanyl}-2-methyl-propionic acid

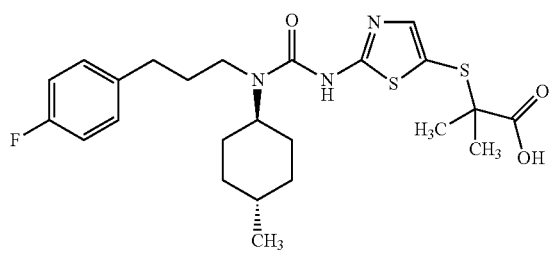 [SMILES: CC(C)(Sc1cnc(NC(=O)N(CCCc2ccc(F)cc2)[C@H]2CC[C@H](C)CC2)s1)C(=O)O]

The compound was prepared following an analogous procedure to the one described for the synthesis of {2[-3-[3-(3-chloro-phenyl)-propyl]-3-(trans-4-methyl-cyclohexyl)-ureido]-thiazol-5-ylsulfanyl}-acetic acid using 3-(4-fluoro-phenyl)-propanoic-acid and 2-(2-amino-thiazol-5-ylsulfanyl)-2-methyl-propionic acid ethyl ester.

¹H NMR (400 MHz, DMSO-d₆) (ppm) 7.40 (s, 1H) 7.25 (t, 2H) 7.10 (t, 2H) 3.87-4.03 (m, 1H) 3.17-3.30 (m, 2H) 2.58 (t, 2H) 1.62-1.82 (m, 4H) 1.52-1.62 (m, 2H) 1.33-1.52 (m, 8H) 1.19-1.33 (m, 1H) 0.96-1.11 (m, 2H) 0.86 (d, 3H)

HPLC-MS: m/z=494 (M+H)

Example 116

2-Methyl-2-{2-[3-(trans-4-methyl-cyclohexyl)-3-(4-p-tolyl-butyl)-ureido]-thiazol-5-ylsulfanyl}-propionic acid

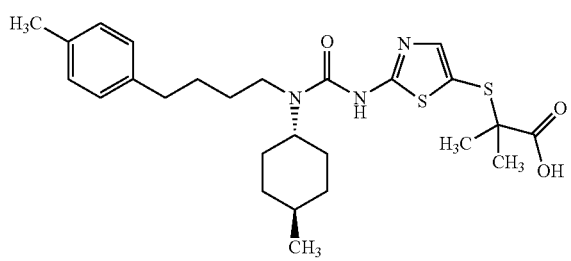 [SMILES: Cc1ccc(CCCCN(C(=O)Nc2ncc(SC(C)(C)C(=O)O)s2)[C@H]2CC[C@H](C)CC2)cc1]

The compound was prepared following an analogous procedure to the one described for the synthesis of {2[-3-[3-(3-chloro-phenyl)-propyl]-3-(trans-4-methyl-cyclohexyl)-ureido]-thiazol-5-ylsulfanyl}-acetic acid using 4-(4-methyl-phenyl)-butyric-acid and 2-(2-amino-thiazol-5-ylsulfanyl)-2-methyl-propionic acid ethyl ester.

¹H NMR (400 MHz, DMSO-d₆) (ppm) 7.39 (s, 1H) 7.00-7.14 (m, 4H) 3.83-4.00 (m, 1H) 3.21 (t, 2H) 2.54 (t, 2H) 2.25 (s, 3H) 1.67 (d, 2H) 1.41-1.61 (m, 8H) 1.23-1.42 (m, 7H) 0.94-1.14 (m, 2H) 0.86 (d, 3H)

HPLC-MS: m/z=504 (M+H)

Example 117

2-{2-[3-[4-(4-Methoxy-phenyl)-butyl]-3-(trans-4-methyl-cyclohexyl)-ureido]-thiazol-5-ylsulfanyl}-2-methyl-propionic acid

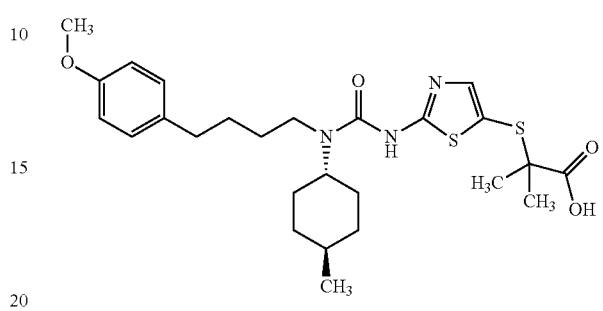

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using 4-(4-methoxy-phenyl)-butyric-acid and 2-(2-amino-thiazol-5-ylsulfanyl)-2-methyl-propionic acid ethyl ester.

¹H NMR (400 MHz, DMSO-d₆) (ppm) 7.39 (s, 1H) 7.11 (d, 2H) 6.83 (d, 2H) 3.84-4.01 (m, 1H) 3.71 (s, 3H) 3.15-3.27 (m, 2H) 2.45-2.60 (m, 2H) 1.67 (d, 2H) 1.41-1.60 (m, 8H) 1.23-1.42 (m, 7H) 0.95-1.11 (m, 2H) 0.86 (d, 3H)

HPLC-MS: m/z=520 (M+H)

Example 118

2-{2-[3-[4-(4-Methoxy-phenyl)-butyl]-3-(trans-4-methyl-cyclohexyl)-ureido]-thiazol-5-ylsulfanyl}-2-methyl-propionic acid

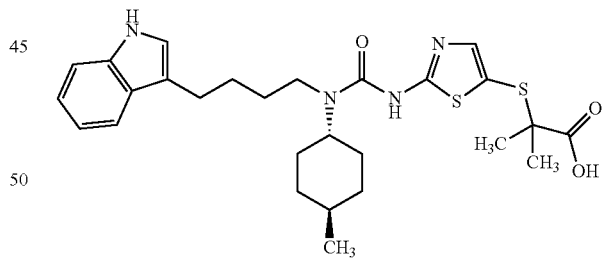

The compound was prepared following an analogous procedure to the one described for the synthesis of {2[-3-[3-(3-chloro-phenyl)-propyl]-3-(trans-4-methyl-cyclohexyl)-ureido]-thiazol-5-ylsulfanyl}-acetic acid using 4-(1H-indol-3-yl)-butyric acid and 2-(2-amino-thiazol-5-ylsulfanyl)-2-methyl-propionic acid ethyl ester.

¹H NMR (400 MHz, DMSO-d₆) (ppm) 10.74 (br. s., 1H) 7.52 (d, 1H) 7.39 (s, 1H) 7.32 (d, 1H) 7.11 (s, 1H) 7.05 (t, 1H) 6.95 (t, 1H) 3.84-4.01 (m, 1H) 3.18-3.29 (m, 2H) 2.70 (t, 2H) 1.42-1.72 (m, 10H) 1.19-1.43 (m, 7H) 0.93-1.12 (m, 2H) 0.86 (d, 3H)

HPLC-MS: m/z=529 (M+H)

Example 119

{2-[3-(trans-4-Methoxy-cyclohexyl)-3-(3-phenyl-propyl)-ureido]-thiazol-5-ylsulfanyl}-acetic acid

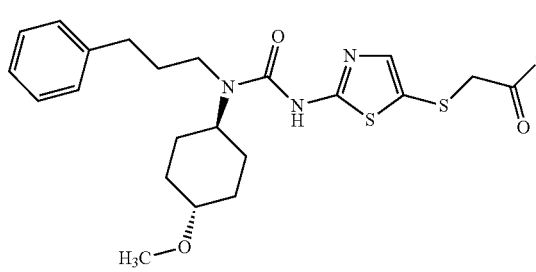

The compound was prepared following an analogous procedure to the one described for the synthesis of {2-[-3-[3-(3-chloro-phenyl)-propyl]-3-(trans-4-methyl-cyclohexyl)-ureido]-thiazol-5-ylsulfanyl}-acetic acid using trans-4-methoxy-cyclohexylamine, 3-phenylpropionic acid and (2-aminothiazol-5-ylsulfanyl) acetic acid ethyl ester.

$^1$H NMR (400 MHz, CDCl$_3$) (ppm) 7.24-7.33 (m, 2H) 7.16-7.24 (m, 4H) 4.04 (br. s., 1H) 3.23-3.38 (m, 7H) 2.99-3.10 (m, 1H) 2.69 (t, 2H) 2.04-2.16 (m, 2H) 1.86-1.99 (m, 2H) 1.75-1.86 (m, 2H) 1.42-1.57 (m, 2H) 1.27-1.43 (m, 2H)

HPLC-MS: m/z=464 (M+1)

Example 120

{2-[3-(Trans-4-methoxy-cyclohexyl)-3-(4-phenyl-butyl)-ureido]-thiazol-5-ylsulfanyl}-acetic acid The compound was prepared following an analogous procedure to the one described for the synthesis of {2[-3-[3-(3-chloro-phenyl)-propyl]-3-(trans-4-methyl-cyclohexyl)-ureido]-thiazol-5-ylsulfanyl}-acetic acid using trans-4-methoxy-cyclohexylamine, 4-phenyl-butyric acid and (2-aminothiazol-5-ylsulfanyl)acetic acid ethyl ester.

$^1$H NMR (400 MHz, CDCl$_3$) (ppm) 7.24-7.32 (m, 2H) 7.13-7.24 (m, 4H) 4.02 (br. s., 1H) 3.35 (s, 3H) 3.30 (s, 2H) 3.18-3.27 (m, 2H) 3.03-3.15 (m, 1H) 2.64 (t, 2H) 2.06-2.16 (m, 2H) 1.74-1.85 (m, 2H) 1.45-1.74 (m, 6H) 1.28-1.45 (m, 2H)

HPLC-MS: m/z=478 (M+1)

Example 121

The compounds in Table 1 are prepared according to synthetic methods as shown in Example 64. The relevant amine and other starting materials are purchased as commercial reagents.

TABLE 1

| Iupac name | Structure |
|---|---|
| 2-{2-[3-[4-(4-Chloro-phenyl)-butyl]-3-(trans-4-methyl-cyclohexyl)-ureido]-thiazol-5-ylsulfanyl}-2-methyl-propionic acid | 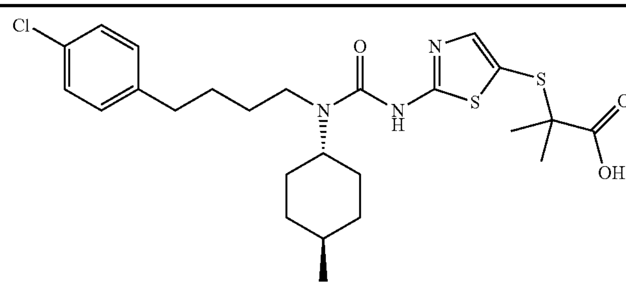 |
| 2-Methyl-2-{2-[3-(trans-4-methyl-cyclohexyl)-3-(3-pyridin-3-yl-propyl)-ureido]-thiazol-5-ylsulfanyl}-propionic acid | 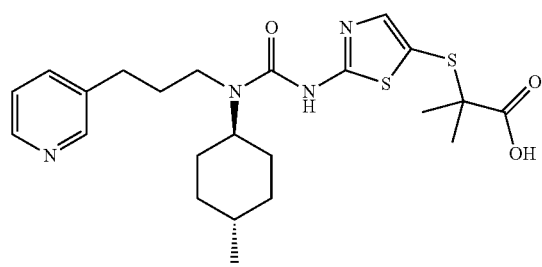 [SMILES: CC(C)(Sc1cnc(NC(=O)N(CCCc2cccnc2)[C@H]2CC[C@H](C)CC2)s1)C(=O)O] |

TABLE 1-continued

| Iupac name | Structure |
|---|---|
| 2-{2-[3-[3-(1H-Indol-3-yl)-propyl]-3-(trans-4-methyl-cyclohexyl)-ureido]-thiazol-5-ylsulfanyl}-2-methyl-propionic acid | 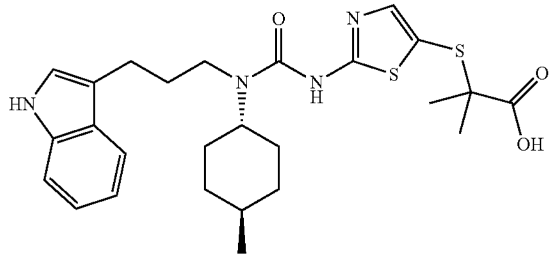 [SMILES: CC(C)(Sc1cnc(NC(=O)N(CCCc2c[nH]c3ccccc23)[C@H]2CC[C@H](C)CC2)s1)C(=O)O] |
| 2-{2-[3-[4-(3,4-Dimethoxy-phenyl)-butyl]-3-(trans-4-methyl-cyclohexyl)-ureido]-thiazol-5-ylsulfanyl}-2-methyl-propionic acid | 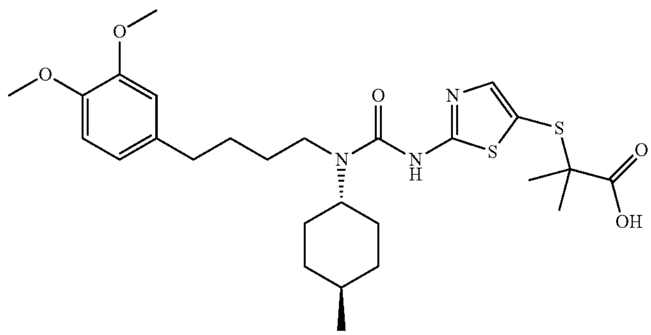 [SMILES: COc1ccc(CCCCN(C(=O)Nc2ncc(SC(C)(C)C(=O)O)s2)[C@H]2CC[C@H](C)CC2)cc1OC] |
| 2-Methyl-2-(2-{3-(4-methyl-cyclohexyl)-3-[2-(trans-4-methylsulfanyl-phenyl)-ethyl]-ureido}-thiazol-5-ylsulfanyl)-propionic acid | 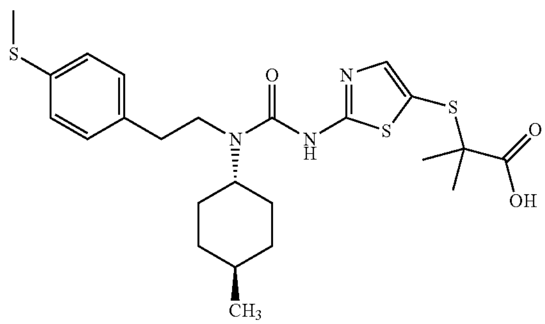 [SMILES: CSc1ccc(CCN(C(=O)Nc2ncc(SC(C)(C)C(=O)O)s2)[C@H]2CC[C@H](C)CC2)cc1] |
| 2-{2-[3-[2-(4-Isopropyl-phenyl)-ethyl]-3-(trans-4-methyl-cyclohexyl)-ureido]-thiazol-5-ylsulfanyl}-2-methyl-propionic acid | 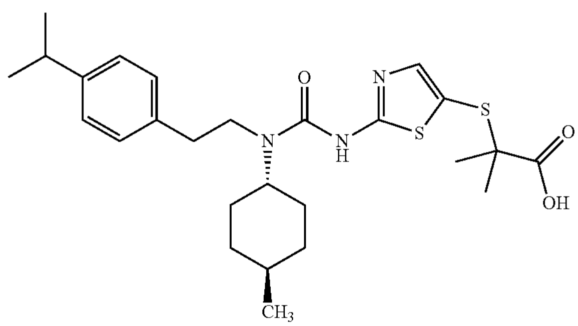 [SMILES: CC(C)c1ccc(CCN(C(=O)Nc2ncc(SC(C)(C)C(=O)O)s2)[C@H]2CC[C@H](C)CC2)cc1] |
| 2-Methyl-2-(2-{3-(trans-4-methyl-cyclohexyl)-3-[2-(3,4,5-trifluoro-phenyl)-ethyl]-ureido}-thiazol-5-ylsulfanyl)-propionic acid | 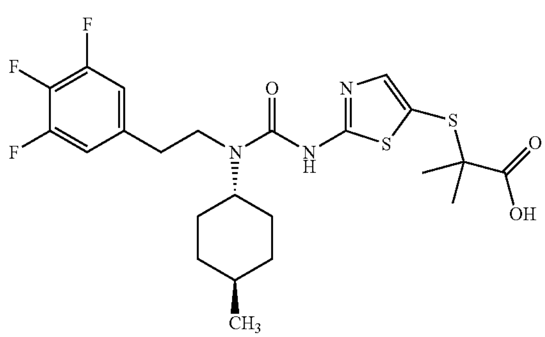 [SMILES: CC(C)(Sc1cnc(NC(=O)N(CCc2cc(F)c(F)c(F)c2)[C@H]2CC[C@H](C)CC2)s1)C(=O)O] |

TABLE 1-continued

| Iupac name | Structure |
|---|---|
| 2-Methyl-2-(2-{3-(trans-4-methyl-cyclohexyl)-3-[2-(2,3,4-trifluoro-phenyl)-ethyl]-ureido}-thiazol-5-ylsulfanyl)-propionic acid | 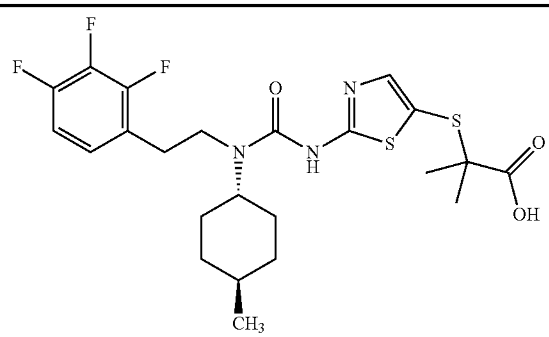 |
| 2-{2-[3-[2-(2-Fluoro-4-methoxy-phenyl)-ethyl]-3-(trans-4-methyl-cyclohexyl)-ureido]-thiazol-5-ylsulfanyl}-2-methyl-propionic acid | 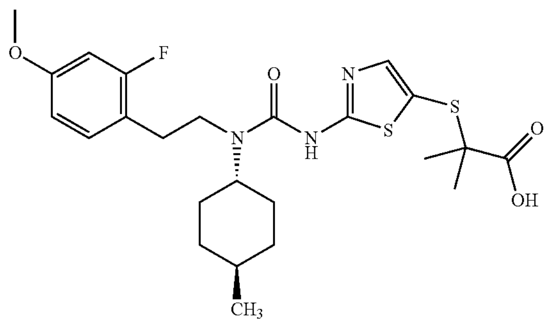 [SMILES: COc1ccc(CCN(C(=O)Nc2ncc(SC(C)(C)C(=O)O)s2)[C@H]2CC[C@H](C)CC2)c(F)c1] |
| 2-{2-[3-[2-(3-Fluoro-4-trifluoromethoxy-phenyl)-ethyl]-3-(trans-4-methyl-cyclohexyl)-ureido]-thiazol-5-ylsulfanyl}-2-methyl-propionic acid | 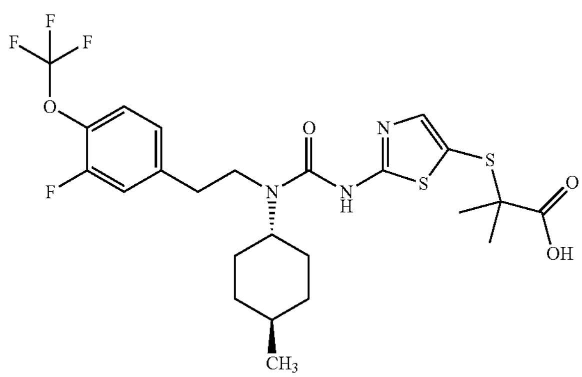 [SMILES: CC(C)(Sc1cnc(NC(=O)N(CCc2ccc(OC(F)(F)F)c(F)c2)[C@H]2CC[C@H](C)CC2)s1)C(=O)O] |
| 2-{2-[3-[2-(3,5-Difluoro-4-methoxy-phenyl)-ethyl]-3-(trans-4-methyl-cyclohexyl)-ureido]-thiazol-5-ylsulfanyl}-2-methyl-propionic acid | 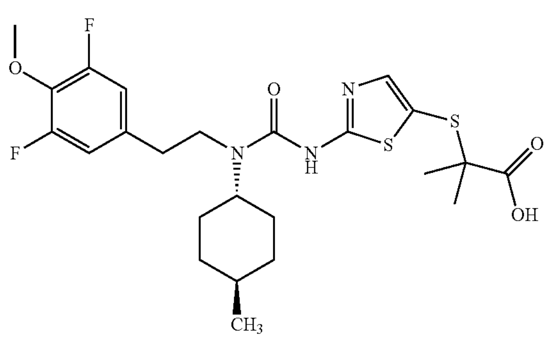 [SMILES: COc1c(F)cc(CCN(C(=O)Nc2ncc(SC(C)(C)C(=O)O)s2)[C@H]2CC[C@H](C)CC2)cc1F] |

TABLE 1-continued

| Iupac name | Structure |
|---|---|
| 2-{2-[3-[2-(4-Methoxy-3-methyl-phenyl)-ethyl]-3-(trans-4-methyl-cyclohexyl)-ureido]-thiazol-5-ylsulfanyl}-2-methyl-propionic acid | 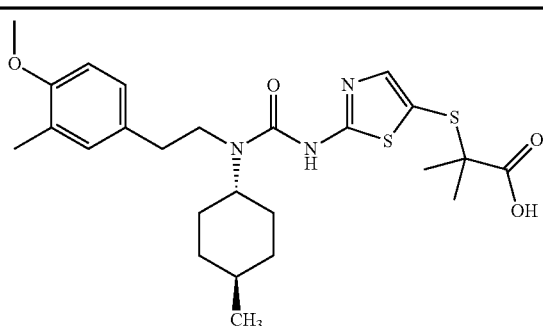 |
| 2-{2-[3-[2-(2,3-Difluoro-4-methoxy-phenyl)-ethyl]-3-(trans-4-methyl-cyclohexyl)-ureido]-thiazol-5-ylsulfanyl}-2-methyl-propionic acid | 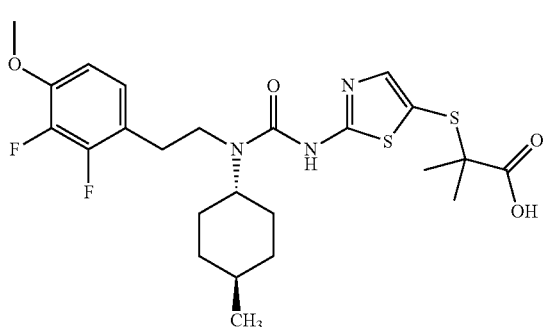 |

The invention claimed is:

1. 2-{2-[3-[2-(4-Methoxy-phenyl)-ethyl]-3-(trans-4-methyl-cyclohexyl)-ureido]-thiazol-5-ylsulfanyl}-2-methyl-propionic acid or a pharmaceutically acceptable salt thereof.

2. A pharmaceutical composition comprising a compound according to claim 1 and a pharmaceutically acceptable carrier.

3. 2-{2-[3-[2-(3-Fluoro-4-methoxy-phenyl)-ethyl]-3-(trans-4-methyl-cyclohexyl)-ureido]-thiazol-5-ylsulfanyl}-2-methyl-propionic acid or a pharmaceutically acceptable salt thereof.

4. A pharmaceutical composition comprising a compound according to claim 3 and a pharmaceutically acceptable carrier.

* * * * *